United States Patent
Wang et al.

(10) Patent No.: US 11,591,294 B2
(45) Date of Patent: Feb. 28, 2023

(54) FLUORENONE/FLUORENOL DERIVATIVES FOR AQUEOUS REDOX FLOW BATTERIES

(71) Applicant: Battelle Memorial Institute, Richland, WA (US)

(72) Inventors: Wei Wang, Kennewick, WA (US); Ruozhu Feng, Richland, WA (US); Xin Zhang, Richland, WA (US); Aaron M. Hollas, Pasco, WA (US); Vijay Murugesan, Richland, WA (US); Nadeesha P. Nambukara Wellala, Richland, WA (US); Yuyan Shao, Richland, WA (US); Zimin Nie, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 17/097,715

(22) Filed: Nov. 13, 2020

(65) Prior Publication Data

US 2021/0147347 A1     May 20, 2021

Related U.S. Application Data

(60) Provisional application No. 63/088,737, filed on Oct. 7, 2020, provisional application No. 62/935,560, filed on Nov. 14, 2019.

(51) Int. Cl.
*H01M 8/18* (2006.01)
*H01M 8/083* (2016.01)
(Continued)

(52) U.S. Cl.
CPC .......... *C07C 309/38* (2013.01); *C07D 241/38* (2013.01); *H01M 8/083* (2013.01);
(Continued)

(58) Field of Classification Search
CPC ........ H01M 2300/0014; H01M 8/188; H01M 8/083; C07C 2603/66; C07D 241/38
See application file for complete search history.

(56) References Cited

U.S. PATENT DOCUMENTS

2015/0307659 A1* 10/2015 Hong ............... H01M 8/20 429/492
2017/0187059 A1*  6/2017 Potash ............... H01M 8/188

OTHER PUBLICATIONS

Rodriguez et. al. ECS Transactions, 89 (1) 49-59 (2019) (Year: 2019).*

(Continued)

*Primary Examiner* — Alexander Usyatinsky
(74) *Attorney, Agent, or Firm* — Klarquist Sparkman, LLP

(57) ABSTRACT

Aqueous electrolytes comprising fluorenone/fluorenol derivatives are disclosed. The electrolyte may be an anolyte for an aqueous redox flow battery. In some embodiments, the compound, or salt thereof, has a structure according to any one of formulas I-III (Continued)

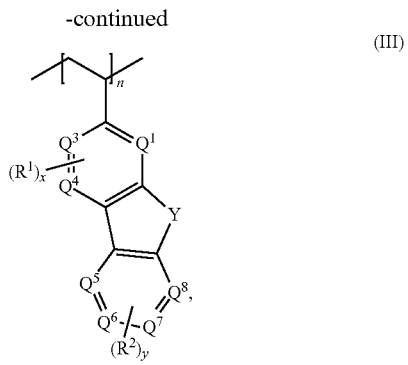

(III)

where $Q^1$-$Q^4$ independently are CH, C($R^1$) or N, wherein 0, 1, or 2 of $Q^1$-$Q^4$ are N; $Q^5$-$Q^8$ independently are CH, C($R^2$), or N, wherein 0, 1, or 2 of $Q^5$-$Q^8$ are N; Y is C=O or C(H)OH; $R^1$ and $R^2$ independently are an electron withdrawing group; n is an integer >1; and x and y independently are 0, 1, 2, 3, or 4, where at least one of x and y is not 0.

21 Claims, 30 Drawing Sheets

(51) Int. Cl.
 *C07C 309/38* (2006.01)
 *C07D 241/38* (2006.01)
(52) U.S. Cl.
 CPC ......... *H01M 8/188* (2013.01); *C07C 2603/66* (2017.05); *H01M 2300/0014* (2013.01)

(56) References Cited

OTHER PUBLICATIONS

Perepichka et. al. J. Org. Chem. 1998, 63, 6484-6493 (Year: 1998).*
By Warner et. al. J.Chem Research (S)1998, p. 814 (Year: 1998).*
Commercial sources for 2,6,-fluorenone carboxylic acid. (Year: NA).*
Hollas et al., "A biomimetic high-capacity phenazine-based anolyte for aqueous organic redox flow batteries," *Nature Energy* 2018, 3:508-514.
Kato et al., "A ketone/alcohol polymer for cycle of electrolytic hydrogen-fixing with water and releasing under mild conditions"; *Nature Communications*; 7:13032 | DOI: 10.1038/ncomms13032; Sep. 30, 2016; 7 pages.
Lin et al., "Alkaline quinone flow battery," *Science* 2015, 349(6255):1529-1532.
Monte et al., "Experimental and Computational Study of the Thermodynamic Properties of 9-Fluorenone and 9-Fluorenol," *J Chem & Eng Data* 2012, 57:2486-2496.
Rodriguez Jr. et al.; "Fluorenone Based Anolyte for an Aqueous Organic Redox-Flow Battery;" *ECS Transactions* 2019, 89(1):49-59.
Zhang et al., "Aerobic Oxidation of 9H-Fluorenes to 9-Fluorenones using Mono-/Multilayer Graphene-Supported Alkaline Catalyst," *ChemPlusChem* 2013, 78:703-711.
9H-Fluorene-4-carboxylic acid, 5-nitro-9-oxo-; PubChem; create date Aug. 9, 2005, modified Dec. 14, 2019, https://pubchem.ncbi.nlm.nih.gov/compound/179635.
7-Amino-9-oxo-9h-fluorene-2-carboxylic acid; PubChem; create date Mar. 26, 2005; modified Dec. 14, 2019; https://pubchem.ncbi.nlm.nih.gov/compound/7-Amino-9-oxo-9h-fluorene-2-carboxylic-acid.
7-Nitro-9-oxo-9H-fluorene-2-carboxylic acid; PubChem; create date Mar. 26, 2005; modified Dec. 14, 2019; https://pubchem.ncbi.nlm.nih.gov/compound/270694.
7-Amino-9-oxofluorene-1-carboxylic acid; PubChem; create date Mar. 26, 2005; modified Dec. 14, 2019; https://pubchem.ncbi.nlm.nih.gov/compound/276234.
7-Formamido-9-oxofluorene-2-carboxylic acid; PubChem; create date Dec. 3, 2011; modified Dec. 14, 2019; https://pubchem.ncbi.nlm.nih.gov/compound/53674143.
7-Nitro-9-oxo-4-fluorenecarboxylic acid; PubChem; create date Mar. 26, 2005, modified Dec. 14, 2019, https://pubchem.ncbi.nlm.nih.gov/compound/97345.

* cited by examiner

FLUORENONE/FLUORENOL DERIVATIVES FOR AQUEOUS REDOX FLOW BATTERIES

CROSS REFERENCE TO RELATED APPLICATIONS

This application claims the benefit of the earlier filing date of U.S. Provisional application No. 63/088,737, filed Oct. 7, 2020, and U.S. Provisional Application No. 62/935,560, filed Nov. 14, 2019, each of which is incorporated by reference in its entirety herein.

ACKNOWLEDGMENT OF GOVERNMENT SUPPORT

This invention was made with Government support under Contract DE-AC05-76RL01830 awarded by the U.S. Department of Energy. The Government has certain rights in the invention.

FIELD

This invention concerns fluorenone/fluorenol derivatives, as well as electrolytes and aqueous redox flow batteries including the fluorenone/fluorenol derivatives.

SUMMARY

Embodiments of an anolyte comprising a fluorenone/fluorenol derivative are disclosed. Aqueous redox flow batteries (ARFBs) including the anolytes also are disclosed. Additionally, embodiments of a method for oxidizing a fluorenol derivative are disclosed.

In some embodiments, an aqueous composition comprises an aqueous anolyte including a compound or a salt thereof having a structure according to any one of formulas I-III, a base; and water.

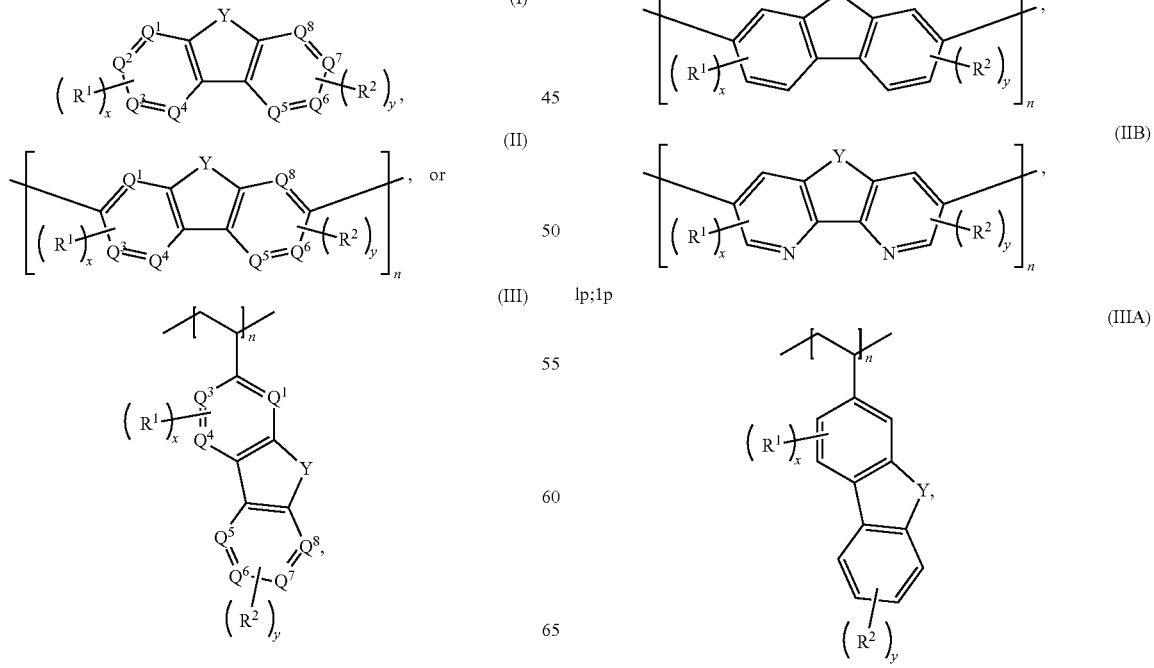

With respect to formulas I-IIII, $Q^1$-$Q^4$ independently are CH, $C(R^1)$ or N, wherein 0, 1, or 2 of $Q^1$-$Q^4$ are N. $Q^5$-$Q^8$ independently are CH, $C(R^2)$, or N, wherein 0, 1, or 2 of $Q^5$-$Q^8$ are N. Y is C=O or C(H)OH. $R^1$ and $R^2$ independently are an electron withdrawing group, and x and y independently are 0, 1, 2, 3, or 4, where at least one of x and y is not 0. With respect to formula III, n is an integer >1. In certain embodiments, each $R^1$ and $R^2$ independently is —$SO_3Z$, —$CO_2Z$, —$(CH_2)_mPO_3Z_2$, X, —$NR'_3^+$, —$NO_2$, —$SO_2R'$, —CN, $CX_3$, —COX, —C(H)O, —C(O)R', —C(O)NH_2, —C(O)NHR', —C(O)NR'_2, —N=O, —OR', or —$(CH_2CH_2O)_pR'$, where each R' independently is H, substituted or unsubstituted aliphatic, or substituted or unsubstituted heteroaliphatic, X is halo, each Z independently is a counterion with a +1 charge, and m is an integer from 0 to 10.

In some embodiments, the compound has a structure according to any one of formulas IA-IC, IIA-IIB, or IIIA-IIIC:

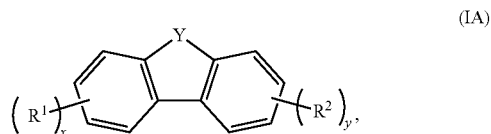

(IA)

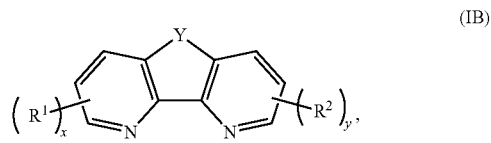

(IB)

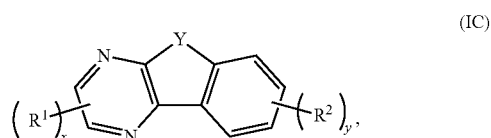

(IC)

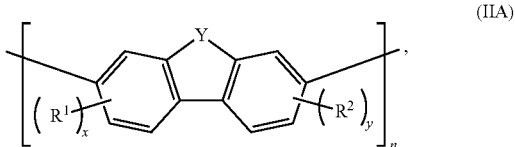

(IIA)

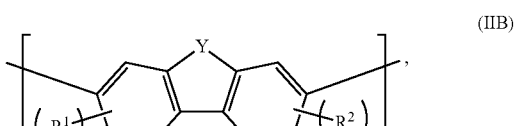

(IIB)

lp;lp

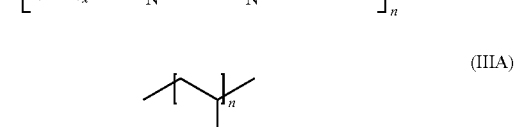

(IIIA)

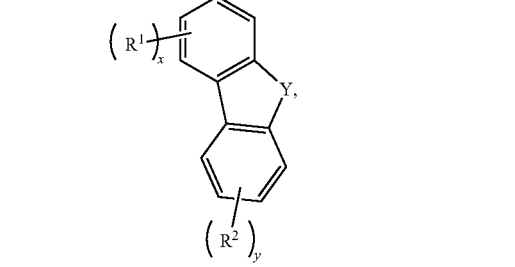

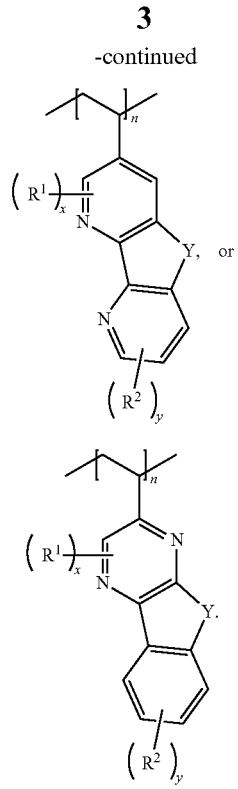

In any of the foregoing or following embodiments, each $R^1$ and $R^2$ independently may be —$SO_3Z$, —$CO_2Z$, —$CF_3$, —$NO_2$, —CN, or —OH. In some embodiments, the compound has a structure according to any one of formulas IA, IIA, or IIIA, and (i) x is 1 or 2, and each $R^1$ independently is —$SO_3Z$ or —$CO_2Z$; or (ii) y is 1, and $R^2$ is —$SO_3Z$; or (iii) both (i) and (ii). In an independent embodiment, each $R^1$ independently is $SO_3Z$ or $CO_2Z$, and each $R^2$ independently is $SO_3Z$ or $CF_3$. In another independent embodiment, the compound has a structure according to formula IC or IIIC, where x is 2 and one $R^1$ is —OH.

In certain examples, the compound comprises

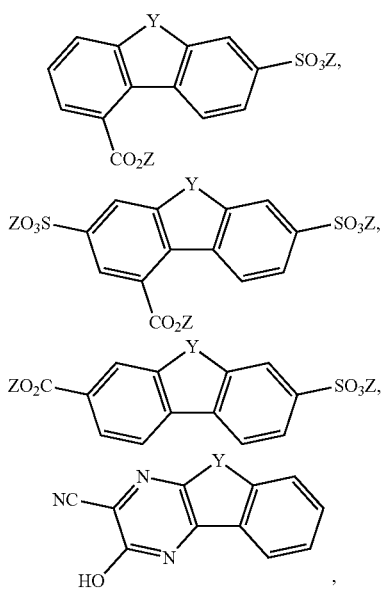

or any combination thereof.

Embodiments of an aqueous electrolyte system for a redox flow battery system include an aqueous anolyte as disclosed herein, and an aqueous catholyte comprising an electrochemically active material. In some embodiments, the aqueous catholyte comprises water and $K_4Fe(CN)_6$, $K_3Fe(CN)_6$, or a combination thereof.

Embodiments of a redox flow battery system include an aqueous electrolyte system as disclosed herein and a separator. In some embodiments, the redox flow battery system further comprises a carbon-based anode and a carbon-based cathode.

Embodiments of a method for oxidizing a fluorenol derivative comprise exposing an aqueous solution comprising a compound as disclosed herein, or a salt thereof, wherein Y is C(H)OH to conditions effective to oxidize the compound to its corresponding ketone where Y is C=O. Advantageously, the method is performed in the absence of a catalyst or oxidizing agent. In some embodiments, the conditions effective to oxidize the compound comprise pairing the aqueous solution against an oxidizing catholyte mixture in an electrochemical cell.

The foregoing and other objects, features, and advantages of the invention will become more apparent from the following detailed description, which proceeds with reference to the accompanying figures.

DETAILED DESCRIPTION

Figure 1:
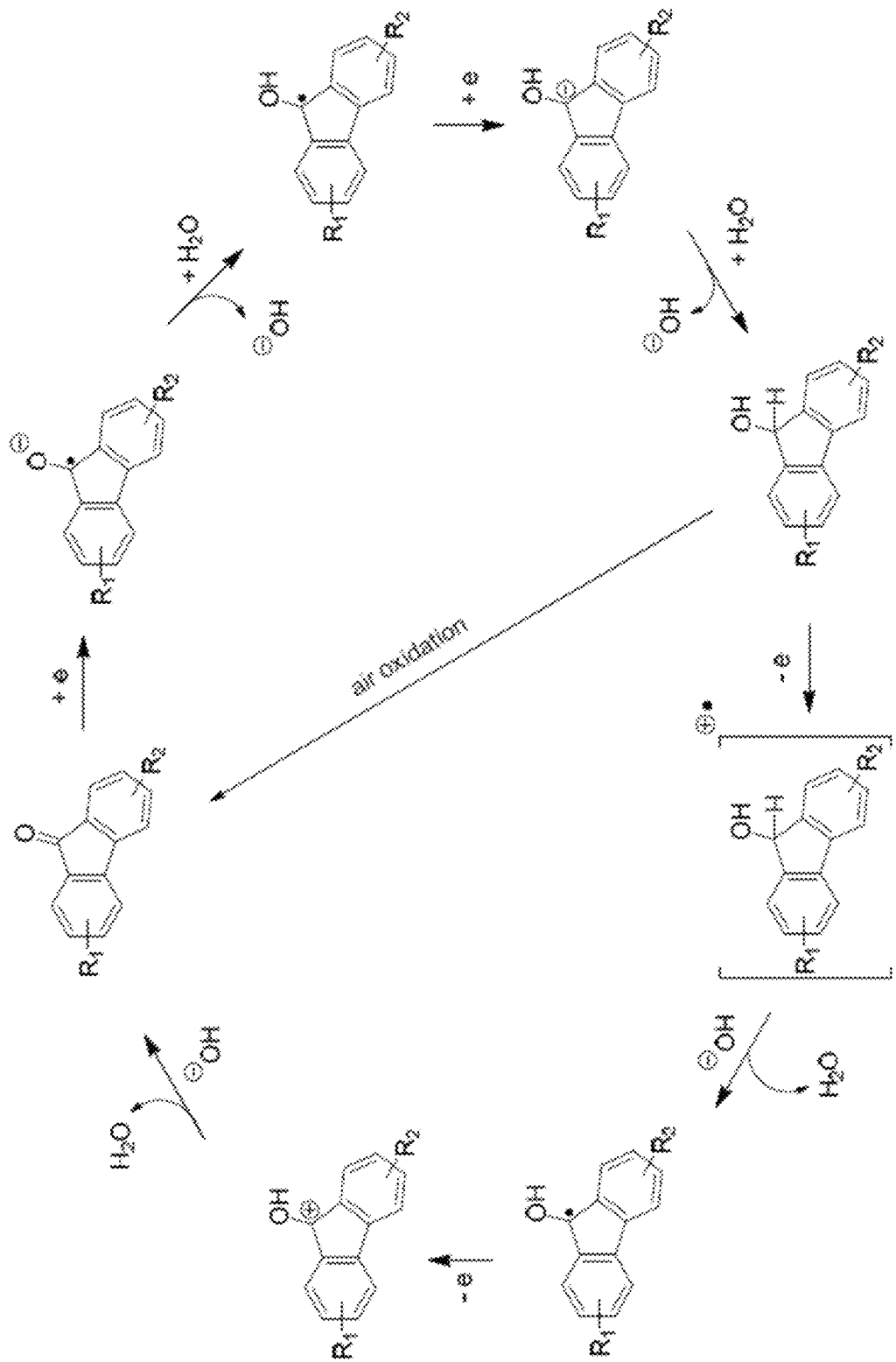
FIG. 1 is a reaction scheme showing a mechanism for redox reversibility of a fluorenone derivative in basic protic media.

Embodiments of fluorenone/fluorenol derivatives are disclosed. Anolytes comprising the compounds and aqueous redox flow batteries (ARFBs) including the anolytes also are disclosed. Advantageously, some embodiments of the disclosed compounds undergo two-electron oxidation-reduction in an ARFB. A catalyst is not required. A method of oxidizing a fluorenol derivative in the absence of a catalyst or oxidizing agent also is disclosed.

I. DEFINITIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly indicates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods, as known to those persons of ordinary skill in the art. When directly and explicitly distinguishing embodiments from discussed prior art, the embodiment numbers are not approximates unless the word "about" is recited.

To facilitate review of the various embodiments of the disclosure, the following explanations of specific terms are provided:

Catalyst: A substance, usually present in small amounts relative to reactants, which increases the rate of a chemical reaction without itself being consumed or undergoing a chemical change. A catalyst also may enable a reaction to proceed under different conditions (e.g., at a lower temperature) than otherwise possible.

Coulombic efficiency (CE): The efficiency with which charges are transferred in a system facilitating an electrochemical reaction. CE may be defined as the amount of charge exiting the battery during the discharge cycle divided by the amount of charge entering the battery during the charging cycle.

Derivative: A compound that is derived from a similar compound or a compound that can be imagined to arise from another compound, for example, if one atom is replaced with another atom or group of atoms. The latter definition is common in organic chemistry.

Electrochemically active component: A component (an element, an ion, or a compound) that is capable of forming redox pairs having different oxidation and reduction states, e.g., ionic species with differing oxidation states, a metal cation and its corresponding neutral metal atom, or a metal cation and its corresponding metal ions at a different oxidation state. In a flow battery, an electrochemically active component refers to the chemical species that participate in the redox reaction during the charge and discharge processes, significantly contributing to the energy conversions that ultimately enable the battery to deliver/store energy. By "significantly contributing" is meant that a redox pair including the electrochemically active component contributes at least 10% of the energy conversions that ultimately enable the battery to deliver/store energy. In some embodiments, the redox pair including the electrochemically active component contributes at least 50%, at least 75%, at least 90%, or at least 95% of the energy conversions in a catholyte or anolyte comprising the electrochemically active component.

Electrolyte: A substance containing free ions and/or radicals that behaves as an ionically conductive medium. In a redox flow battery, some of the free ions and/or radicals are electrochemically active components. An electrolyte in contact with the anode, or negative half-cell, may be referred to as an anolyte, and an electrolyte in contact with the cathode, or positive half-cell, may be referred to as a catholyte. The anolyte and catholyte are often referred to as the negative electrolyte and positive electrolyte, respectively, and these terms can be used interchangeably. As used herein, the terms anolyte and catholyte refer to electrolytes composed of electrochemically active components and an aqueous supporting solution.

Electron withdrawing group: An atom or group capable of drawing electron density from neighboring atoms towards itself, usually by resonance or inductive effects. For a substituent on an aryl ring, an electron withdrawing group typically has an atom bound to the ring with the atom also having several bonds to more electronegative atoms (e.g., O, F, C, N). Exemplary electron withdrawing groups include, but are not limited to, —$SO_3^-$, —$CO_2^-$, —X (X=F, Cl, Br, I), —$NO_2$, —CN, —$NR_3^+$ (R=alkyl or H), —$CF_3$, —$SO_2CF_3$, $SO_2R$, —COX (X=F, Cl, Br, I), —CHO, —C(O)R (R=alkyl), and C(O)$NR_2$ (R=alkyl or H).

Energy efficiency (EE): The product of coulombic efficiency and voltage efficiency. EE=CE×VE.

Oxidizing agent: A substance capable of oxidizing another substance, i.e., capable of accepting electrons from another substance. The oxidizing agent is, in turn, reduced.

Redox pair or redox couple: An electrochemically active component and its corresponding oxidized (or reduced) component. Exemplary redox pairs include, but are not limited to, $[Fe(CN)_6]^{4-}/[Fe(CN)_6]^{3-}$, $Li^+/Li$, etc.

Voltage efficiency (VE): The voltage produced by the battery while discharging divided by the charging voltage.

II. FLUORENONE/FLUORENOL DERIVATIVES AND ELECTROLYTES

Fluorenone for use in nonaqueous flow batteries has been reported with a one-electron transfer process. However, considering the high dehydrogenation energy (62.3-66.1 kJ/mol), a complete two-electron transfer process between the carbonyl-containing fluorenone and hydroxyl-containing fluorenol would double the energy storage capability. Electrochemical oxidation of the hydroxyl moiety of fluorenol generally requires metal catalysis and shows relatively slow kinetics. Both factors impede redox activity reversibility, and render it very difficult to provide stable cycling in a redox flow battery, particularly an aqueous redox flow battery (ARFB), through reversible redox reactions.

Disclosed herein are embodiments of an aqueous anolyte comprising a compound for use in an ARFB. The compound is a fluorenone/fluorenol derivative, wherein the fluorenone derivative and corresponding fluorenol derivative undergo a reversible two-electron transfer process. Advantageously, a catalyst is not required. In some embodiments, the battery can operate at room temperature (e.g., 20-25° C.) and/or at elevated temperatures (e.g., 50° C., or more). In certain embodiments, the disclosed anolyte provides long-term cycling stability, as evidenced by charge/discharge capacity, Coulombic efficiency, energy efficiency voltage efficiency, or any combination thereof that varies by less than 10%, or less ±5% over at least 50 cycles, at least 100 cycles, at least 200 cycles, or even at least 250 cycles after an initial 5-10 cycles.

The compound has a structure according to any one of formulas I-III:

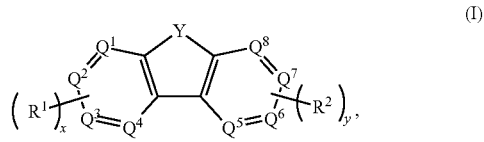

(I)

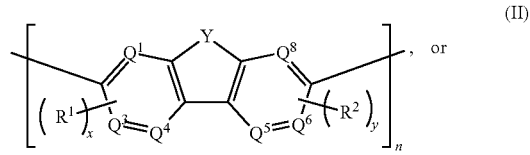

(II), or (III)

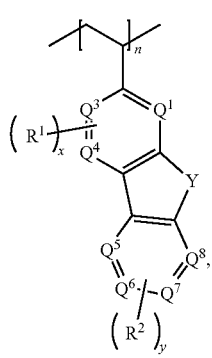

(IIIA)

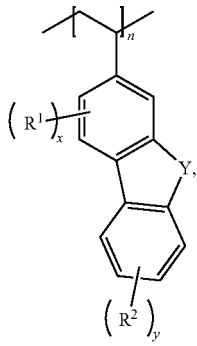

(IIIB)

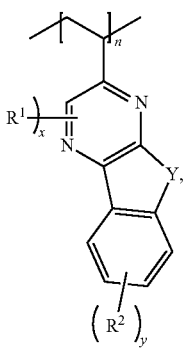

(IIIC)

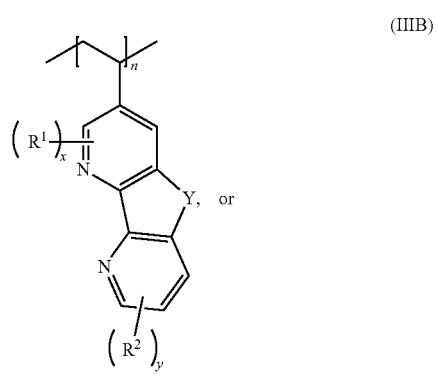

With respect to formulas I-IIII, $Q^1$-$Q^4$ independently are CH, C($R^1$) or N, wherein 0, 1, or 2 of $Q^1$-$Q^4$ are N. $Q^5$-$Q^8$ independently are CH, C($R^2$), or N, wherein 0, 1, or 2 of $Q^5$-$Q^8$ are N. Y is C=O or C(H)OH. Each $R^1$ and $R^2$ independently is an electron withdrawing group. The variables x and y independently are 0, 1, 2, 3, or 4, where if none of $Q^1$-$Q^8$ is N, then x and y are not 0. With respect to formulas II and III, n is an integer >1. In some embodiments, the compound is not 7-nitro-9-oxo-9H-fluorene-2-carboxylic acid, 7-nitro-9-oxo-9H-fluorene-4-carboxylic acid, 5-nitro-9-oxo-9H-fluorene-4-carboxylic acid, 7-amino-9-oxo-9H-fluorene-2-carboxylic acid, 7-amino-9-oxo-9H-fluorene-1-carboxylic acid, or 7-foramido-9-oxo-9H-fluorene-2-carboxylic acid.

In some embodiments, the compounds have a formula according to any one of formulas IA-IC, IIA-IIB, or IIIA-IIIC:

(IA)

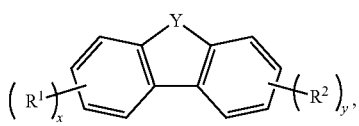

(IB)

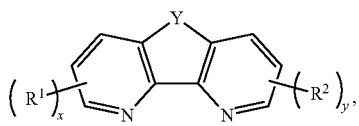

(IC)

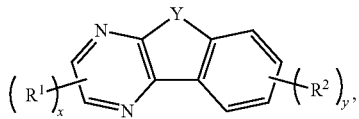

(IIA)

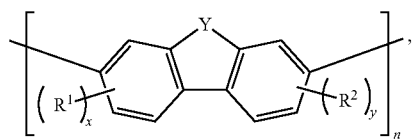

(IIB)

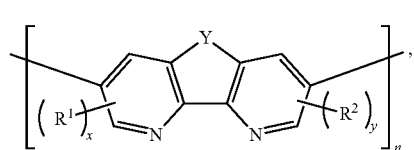

where Y is C=O or C(H)OH, $R^1$, $R^2$, n, x, and y are as previously defined. In some embodiments, the compound has a structure according to formula IA, IB, or IC.

The presence of electron withdrawing groups stabilizes the reversible two-electron reaction and/or may enhance aqueous solubility of the compound. Without wishing to be bound by a particular theory of operation, the inclusion of a sufficient number and type of electron withdrawing groups on the ring system can activate the reduced fluorenol in aqueous media and enable its re-oxidation at carbon electrodes. With appropriate electron withdrawing groups, the alcohol species has sufficiently low pKa so that it can be deprotonated in strong basic water solution to form an anionic intermediate to initiate reversible oxidation.

An exemplary reaction with a fluorenone derivative according to formula I in basic protic media is shown below where • represents a radical:

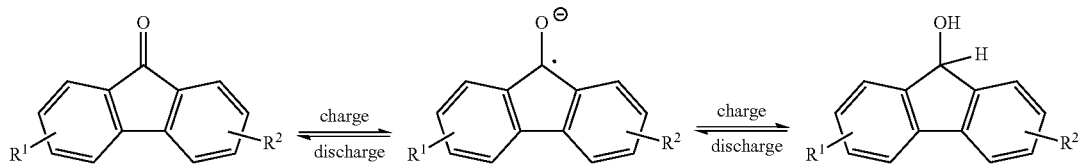

Figure 2:
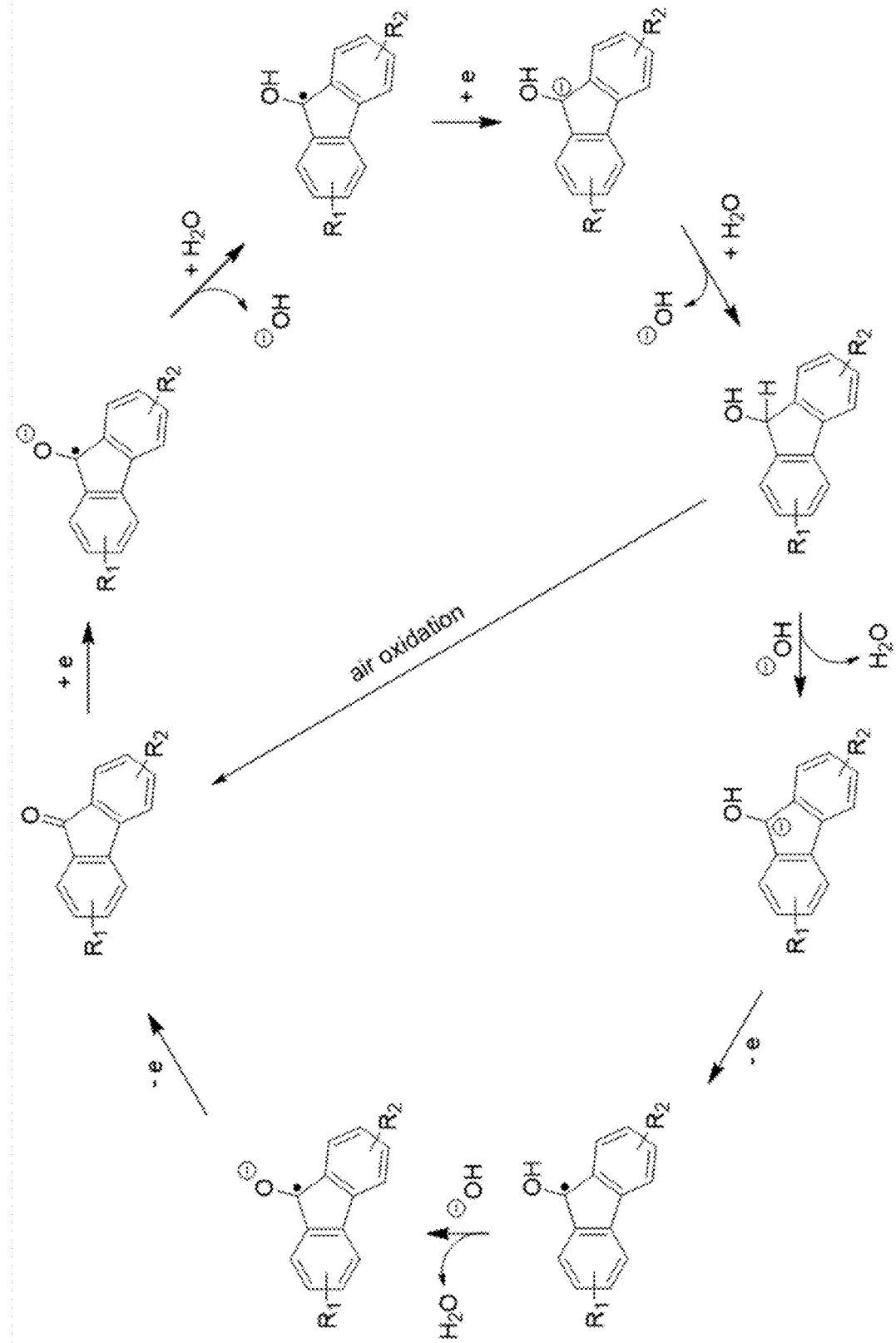
FIG. 2 is a reaction scheme showing an alternative mechanism for redox reversibility of a fluorenone derivative in basic protic media.

The exemplary schemes in FIGS. 1-2 show details of reaction mechanisms for the two-electron reaction of fluorenone and fluorenone derivatives. Without wishing to be bound by a particular theory of operation, some embodiments of the disclosed compounds exhibit a low potential, without a catalyst, for conversion of the radical anion 2 and dianion 3 as shown in the exemplary reaction below. In certain embodiments, the compounds are useful in AFRBs with carbon-based anodes.

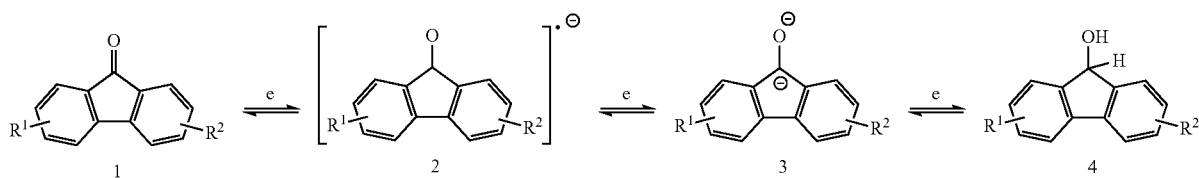

In any of the foregoing or following embodiments, each $R^1$ and $R^2$ independently may be —$SO_3Z$, —$CO_2Z$, —$(CH_2)_mPO_3Z_2$, X, —$NR'_3{}^+$, —$NO_2$, —$SO_2R'$, —CN, $CX_3$, —COX, —C(H)O, —C(O)R', —C(O)NH$_2$, —C(O)NHR', —C(O)NR'$_2$, —N=O, —OR', or —$(CH_2CH_2O)_pR'$. Each R' independently is H, substituted or unsubstituted aliphatic, or substituted or unsubstituted heteroaliphatic. Each X independently is halo (F, Cl, Br, I), each Z independently is a counterion with a +1 charge, m is an integer from 0 to 10, and p is an integer from 1 to 10. Exemplary counterions with a +1 charge include, but are not limited to, $H^+$, $Na^+$, $K^+$, and $NH_4{}^+$. In some embodiments, each electron withdrawing group independently is —$SO_3Z$, —$CO_2Z$, halo, —CN, or —OH. In certain embodiments, each electron withdrawing group independently is —$SO_3Z$ or —$CO_2Z$. In some examples, Z is $Na^+$ or $K^+$.

In some embodiments, $Q^1$-$Q^4$ independently are CH or C($R^1$), and $Q^5$-$Q^8$ independently are CH or C($R^2$). In independent embodiment, one of $Q^1$-$Q^4$ is N and one of $Q^5$-$Q^8$ is N. In another independent embodiment, two of $Q^1$-$Q^4$ are N, and none of $Q^5$-$Q^8$ is N. in still another independent embodiment, two of $Q^1$-$Q^4$ are N, and two of $Q^5$-$Q^8$ are N. In one example, $Q^1$ and $Q^4$ are N. In another example, $Q^4$ and $Q^5$ are N.

With respect to formulas I and II, x and y independently are 0, 1, 2, 3, or 4, where if none of $Q^1$-$Q^8$ is N, then x and y are not 0. With respect to formula III, x is 0, 1, 2, or 3; y is 0, 1, 2, 3, or 4, where if none of $Q^1$, $Q^3$-$Q^6$, or $Q^8$ is N, then x and y are not 0. In some embodiments, x is 1 or 2, and y is 1 or 2. In one embodiment, x is 1 and y is 1. In an independent embodiment, one of x and y is 2 and the other of x and y is 1. In another independent embodiment, x is 2 and y is 2. Instill another independent embodiment, x is 2 and y is 0. In another independent embodiment, none of $Q^1$-$Q^8$ is N, and x and y independently are 1 or 2; in some examples, x+y=2 or 3. In yet another independent embodiment, one of $Q^1$-$Q^4$ is N, one of $Q^5$-$Q^8$ is N, and x and y independently are 0, 1, or 2. In still another independent embodiment, two of $Q^1$-$Q^4$ are N, none of $Q^5$-$Q^8$ is N, x is 1 or 2, and y is 0, 1, or 2; in some examples, x+y=2 or 3. In one example, $Q^1$ and $Q^4$ are N. x is 2, and y is 0. In another example, $Q^4$ and $Q^5$ are N, and x and y are 0.

In some embodiments, the compound has a structure according to formula IA, IIA, or IIIA, where x is 1 or 2, and each $R^1$ independently is —$SO_3Z$ or —$CO_2Z$. In some embodiments, y is 1 and $R^2$ is —$SO_3Z$. In certain embodiments, x is 1 or 2, and each $R^1$ independently is —$SO_3Z$ or —$CO_2Z$; and y is 1 and $R^2$ is —$SO_3Z$.

In any of the foregoing embodiments, $R^1$ and $R^2$ may be asymmetrically positioned on the compound. In any of the foregoing embodiments, $R^1$ and $R^2$ may be different electron withdrawing groups. In some embodiments, $R^1$ and $R^2$ are different electron withdrawing groups and are asymmetrically positioned on the compound.

Exemplary compounds include, but are not limited to, the compounds in Table 1. In the naming convention used in Table 1, the numbers refer to ring positions, D=di, H=hydroxy, C=carboxylate/carboxylic acid, S=sulfonate or sulfonic acid, and FL=fluorenone. Itis understood that, where sulfonate and carboxylate substituents are shown with a particular cation, compounds with alternative cations, e.g., $H^+$, $K^+$, $Na^+$, or $NH_4{}^+$, are envisioned and included within the scope of this disclosure.

TABLE 1
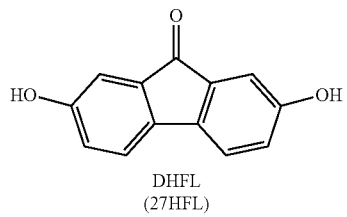 [SMILES: O=C1c2cc(O)ccc2-c2ccc(O)cc21]
DHFL
(27HFL)
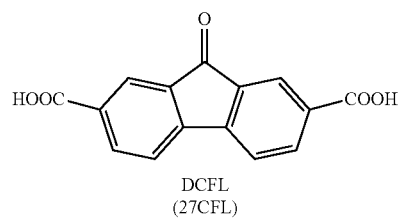 [SMILES: O=C(O)c1ccc2c(c1)C(=O)c1cc(C(=O)O)ccc1-2]
DCFL
(27CFL)
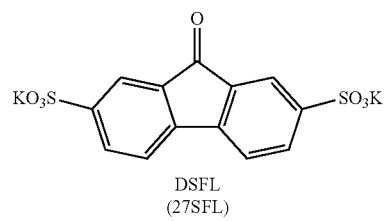
DSFL
(27SFL)
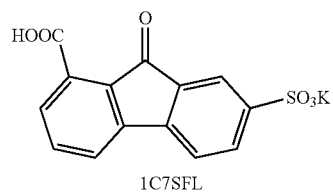
1C7SFL
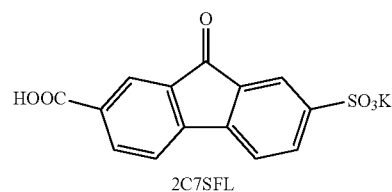
2C7SFL
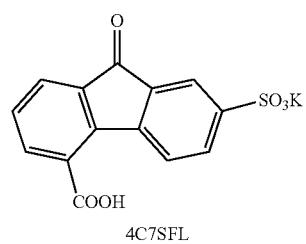
4C7SFL
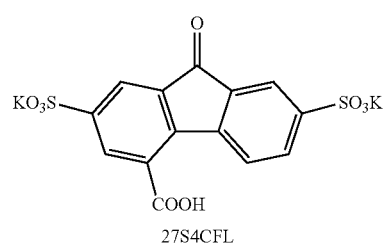
27S4CFL TABLE 1-continued
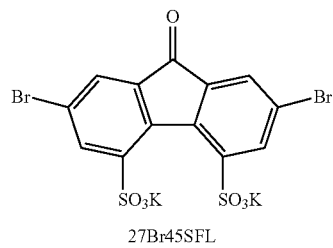
27Br45SFL
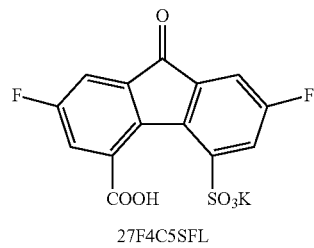
27F4C5SFL
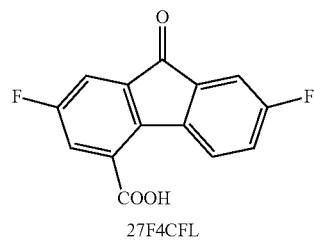 [SMILES: O=C(O)c1cc(F)cc2c1-c1ccc(F)cc1C2=O]
27F4CFL
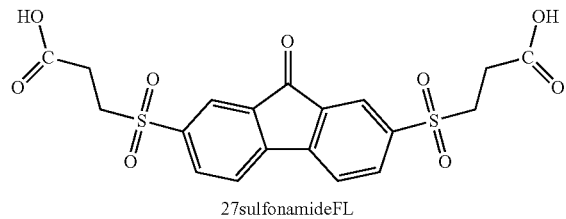 [SMILES: O=C(O)CCS(=O)(=O)c1ccc2c(c1)C(=O)c1cc(S(=O)(=O)CCC(=O)O)ccc1-2]
27sulfonamideFL
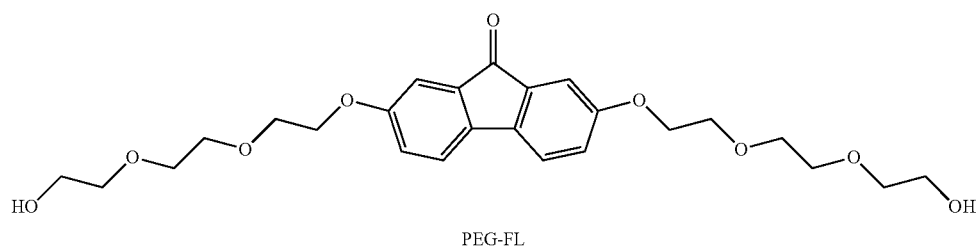 [SMILES: O=C1c2cc(OCCOCCOCCO)ccc2-c2ccc(OCCOCCOCCO)cc21]
PEG-FL
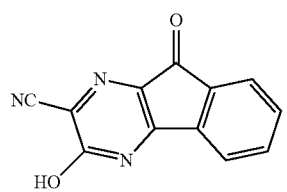
14N2CN3OHFL TABLE 1-continued

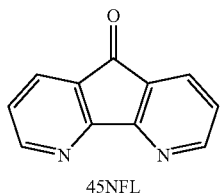 [SMILES: O=C1c2cccnc2-c2ncccc21]

45NFL

In some embodiments, the compound comprises

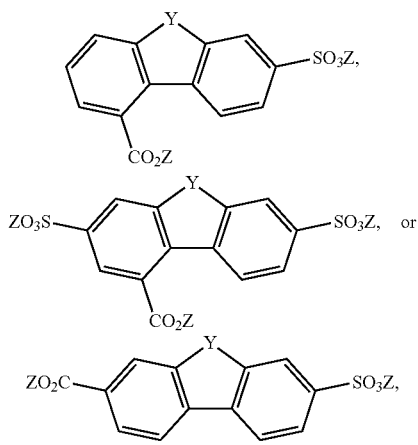

where Z is as previously defined. In certain embodiments, the substituents are —COOH and —SO$_3$K. In an independent embodiment, the compound comprises

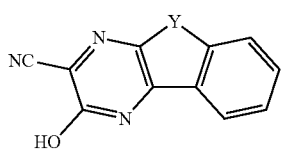

In some embodiments, the disclosed aqueous anolytes comprise a compound as disclosed herein, a base, and water. In certain embodiments, the base is an alkali metal hydroxide. The base may be, for example, sodium hydroxide, potassium hydroxide, or a combination thereof. In certain embodiments, the aqueous anolyte consists essentially of, or consists of, the compound, the base, and water. As used herein, "consists essentially of" means that the anolyte does not include any additional components that may materially affect properties of the anolyte or a battery including the anolyte. For example, the anolyte does not include any electrochemically- or redox-active component (i.e., a component (an element, an ion, or a compound) that is capable of forming redox pairs having different oxidation and reduction states, e.g., ionic species with differing oxidation states or a metal cation and its corresponding neutral metal atom) other than the compound as disclosed herein in an amount sufficient to affect performance of the anolyte, and the anolyte does not include more than a trace amount (e.g., no more than 1 wt %) of a non-aqueous solvent.

In any of the foregoing embodiments, the compound may be present in the anolyte at a concentration within a range of from 0.5 M to 1.5 M. In some embodiments, the compound has a concentration within a range of from 0.5-1.5 M.

Embodiments of an aqueous electrolyte system for a redox flow battery system comprise an aqueous anolyte as disclosed herein, and an aqueous catholyte comprising an electrochemically active material suitable for use in a redox flow battery. In one embodiment, the catholyte comprises a base and the electrochemically active material. In an independent embodiment, the catholyte comprises an acid and the electrochemically active material. The catholyte may consist essentially of, or consist of, water, the base or the acid, and the electrochemically active material. In certain embodiments, the base or acid is the same base acid, respectively, as that of the anolyte, and may have the same concentration as the base or acid in the anolyte. In some examples, the electrochemically active material in the catholyte is potassium ferrocyanide (K$_4$Fe(CN)$_6$). In certain examples, the catholyte is an aqueous solution comprising a base and K$_4$Fe(CN)$_6$. Because the disclosed fluorenone/fluorenol derivatives undergo a 2-electron redox process, the amount (number of moles) of K$_4$Fe(CN)$_6$ in the catholyte in some embodiments is twice the amount of the fluorenone/fluorenol derivative in the anolyte.

III. REDOX FLOW BATTERIES

Figure 3:
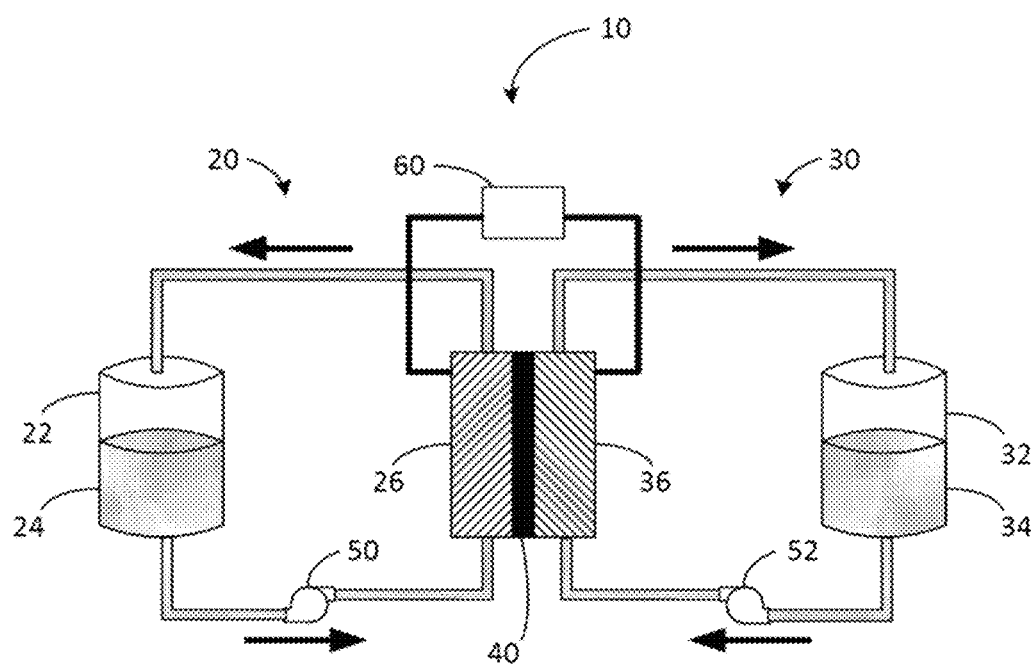
FIG. 3 is a schematic diagram of an exemplary redox flow battery system.

Redox flow batteries (RFBs) can provide electrical energy converted from chemical energy continuously, and are promising systems for energy storage, providing flexibility and resiliency to the power grid. As shown in FIG. 3, some embodiments of an aqueous RFB (ARFB) system 10 comprise a positive half-cell 20 and a negative half-cell 30. The half-cells are separated by a membrane or separator 40, such as an ion-exchange membrane (cation- or anion-exchange membrane), ion conductive membrane (polymer or ceramic) or porous separator. The positive half-cell 20 comprises an electrode tank 22 containing a catholyte 24 and the negative half-cell 30 comprises an electrode tank 32 containing an anolyte 34. The anolyte and catholyte are solutions comprising electrochemically active components in different oxidation states. The electrochemically active components in the catholyte and anolyte couple as redox pairs. In some embodiments, at least one of the catholyte and anolyte redox active materials remains fully soluble during the charging and discharging cycles of the RFB.

The battery may be assembled in ambient atmosphere in a housing that is closed and operated without flowing an inert gas through the housing. In some embodiments, the housing may be sealed such that additional oxygen from the ambient atmosphere is excluded or substantially excluded. Embodiments of the disclosed battery may operate at a lower cost than comparable RFBs that require constant flow of an inert gas.

During charging and discharging of the ARFB, the catholyte and anolyte are continuously circulating via pumps 50, 52 through the positive and negative electrodes 26, 36, respectively, where redox reactions proceed, providing the conversion between chemical energy and electrical energy or vice-versa. To complete the circuit during use, positive and negative electrodes (including a current collector at each side) 26, 36 of the ARFB system 10 are electrically connected through current collectors (not shown) with an external load 60. The electrodes are selected to be stable with the anolyte and catholyte. In some embodiments, the electrodes are carbon-based. Suitable carbon-based materials include, but are not limited to, carbon felt, carbon paper, and woven carbon cloth. Exemplary separators include, but are not limited to, cation-exchange membranes, such as Nafion™ N115, NR-212, and NR-211 membranes (available from Ion Power, Inc., New Castle, Del.).

Figure 4:
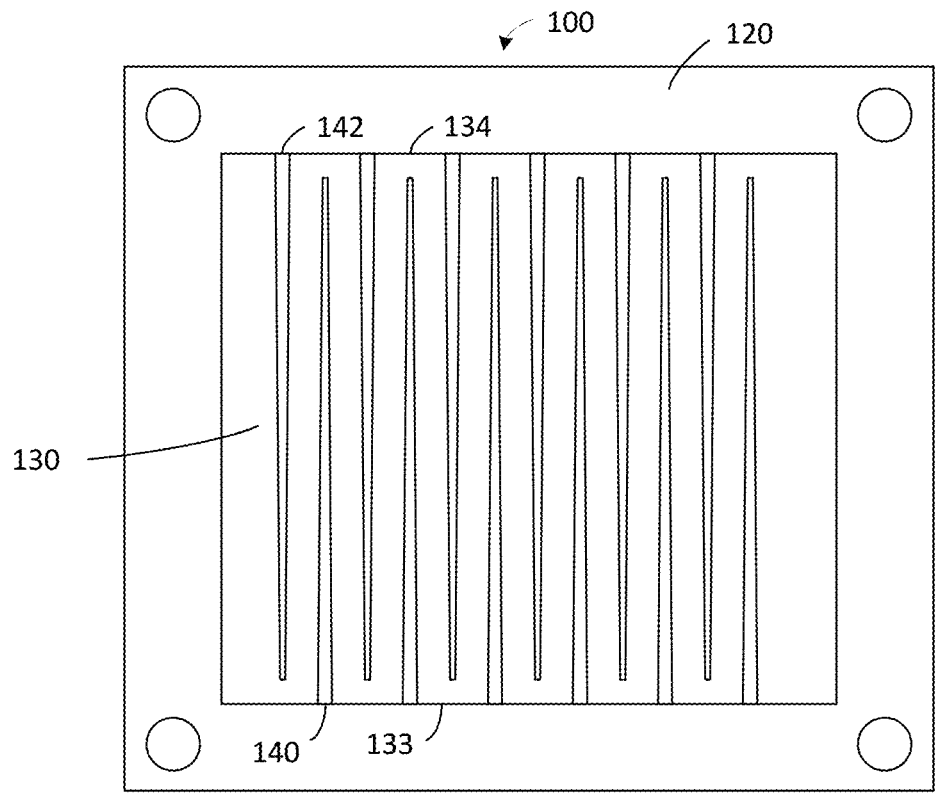
FIG. 4 is a simplified diagram of an exemplary flow half-cell including interdigitated inlet and outlet flow channels.
Figure 5:
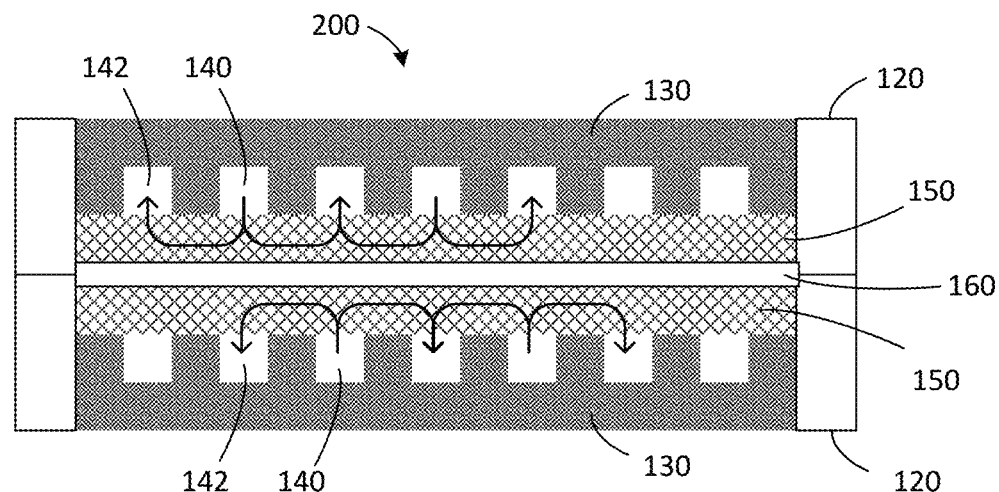
FIG. 5 is a cross-sectional view of an exemplary redox flow battery stack cell with an interdigitated design.

In some embodiments, the ARFB is a flow cell with an interdigitated design of flow channels. FIG. 4 is a simplified diagram of one exemplary half cell 100 comprising a support frame 120 and a bipolar plate 130 with interdigitated inlet and outlet flow channels 140, 142. The inlet flow channels 140 extend inwardly from a first side edge 133 of the bipolar plate 130 and have a closed distal end. The outlet flow channels 142 extend inwardly from the opposing side edge 134 of the bipolar plate and also have a closed distal end. The bipolar plate 130 may also include flow channels on the opposing surface with anolyte circulating through the channels on one side of the plate and catholyte circulating through the flow channels on the opposing side. With reference to the cross-sectional view of FIG. 5, a redox flow battery stack cell 200 comprises two electrodes 150 and an ion-exchange membrane or separator 160. The electrodes 150 are disposed on either side of and in contact with the separator 160. The redox flow battery stack cell 200 further comprises two half cells 100 each half cell comprising a support frame 120 and bipolar plate 130. The half cells are positioned such that a bipolar plate 130 is in contact with each electrode 150. The electrode 150 may be porous so that an electrolyte may flow through the electrode. In some embodiments, the electrode 150 comprises a carbonaceous material, such as carbon felt, carbon paper, and woven carbon cloth. Exemplary separators include those described above. End plates on either side of the cell include a current collector in electrical communication with the cell (not shown). The arrows in FIG. 3 illustrate the direction of electrolyte flow through the redox flow battery stack cell 200. An electrolyte flowing through an inlet flow channel 140 cannot directly exit the inlet flow channel because the distal end of the inlet flow channel is closed (FIG. 4). As shown in FIG. 5, the electrolyte flows from the inlet flow channel 140 into the electrode 150, through the electrode 150 in a direction substantially perpendicular to the inlet flow channel 140, and subsequently into adjacent outlet flow distribution channels 142. Several cells may be assembled into a battery stack (not shown) with an end plate at each end of the stack.

Embodiments of the disclosed aqueous electrolytes comprising a fluorenone/fluorenol derivative as disclosed herein are suitable for use as the anolyte. The catholyte is an aqueous solution comprising an electrochemically active material suitable for use in a redox flow battery. In one embodiment, the catholyte comprises a base and the electrochemically active material. In an independent embodiment, the catholyte comprises an acid and the electrochemically active material. The catholyte may consist essentially of, or consist of, water, the base or the acid, and the electrochemically active material. In certain embodiments, the base is the same base as that of the anolyte, and may have the same concentration as the base in the anolyte. In some examples, the electrochemically active material in the catholyte is potassium ferrocyanide ($K_4Fe(CN)_6$). In certain examples, the catholyte is an aqueous solution comprising a base and $K_4Fe(CN)_6$. Because the disclosed compounds undergo a 2e⁻ redox process, the amount (number of moles) of $K_4Fe(CN)_6$ in the catholyte in some embodiments is twice the amount of the fluorenone/fluorenol derivative in the anolyte.

In some embodiments, an ARFB system as disclosed herein demonstrates excellent capacity retention. In one example, an ARFB with an anolyte comprising 1.4 M 9-oxo-7-sulfo-9H-fluorene-4-carboxylic acid (4C7SFL) in 1 M NaOH and a ferro/ferricyanide catholyte solution exhibited a capacity retention of 97.38% over 120 days of operation. In another example, an ARFB with an anolyte comprising 1 M 4C7SFL and a catholyte with excess potassium ferri/ferrocyanide exhibited an anolyte volumetric capacity of 39.3 Ah/L and a stable discharge over 1V for hundreds of cycles across several weeks at 20 mA/cm². Advantageously, in some embodiments, the disclosed ARFB systems provide long-term stable operation at temperatures up to 50° C. In some embodiments, the battery is operated under an inert (e.g., nitrogen, helium, argon) atmosphere. Certain embodiments of the disclosed ARFB systems may be operable in an air atmosphere, without the need for an inert atmosphere.

IV. OXIDATION OF FLUORENOL DERIVATIVES

Some embodiments of the disclosed fluorenol derivatives (Y is C(H)OH) may be oxidized to the corresponding fluorenone (Y is C=O) in the absence of a catalyst or oxidizing agent. In certain embodiments, the fluorenol derivative has a structure according to any one of formulas I-III as previously disclosed where Y is C(H)OH, each $R^1$ independently is $SO_3Z$ or $CO_2Z$, each $R^2$ independently is $SO_3Z$ or $CF_3$, each Z independently is a counterion with a +1 charge, n is an integer greater than 1, and x and y independently are 1, 2, 3, or 4. Exemplary compounds include, but are not limited to:

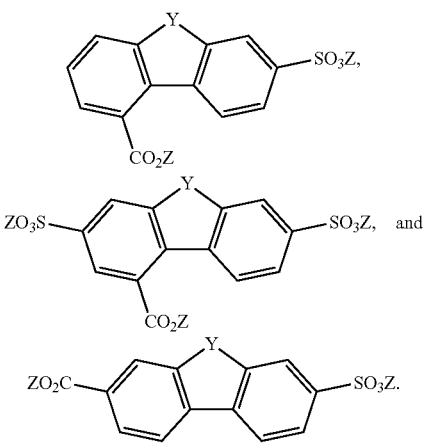

Figure 30:
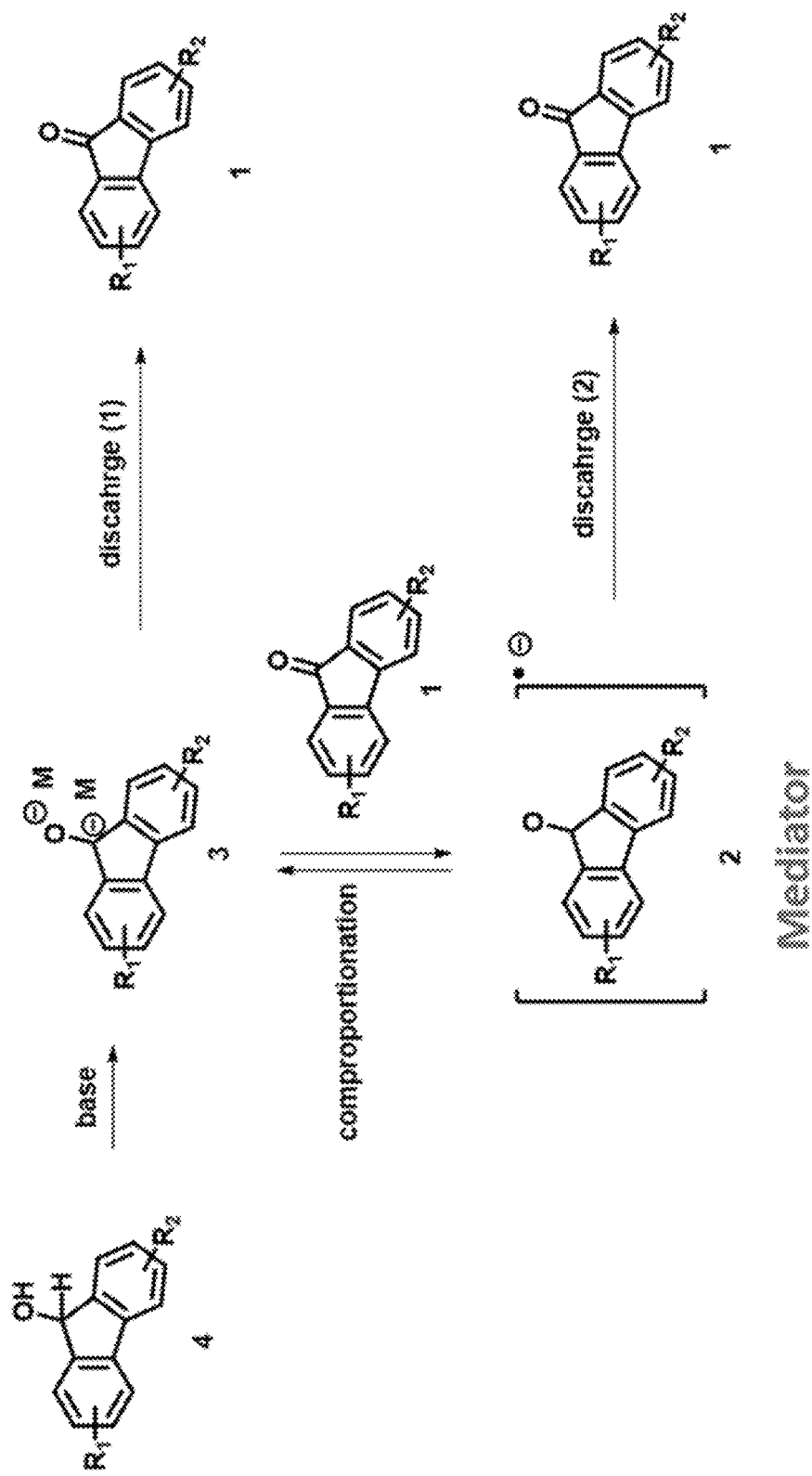
FIG. 30 is a reaction scheme showing a comproportionation reaction of fluorenol to fluorenone.

An aqueous solution comprising the fluorenol derivative, or a salt thereof, is exposed to conditions effective to oxidize the alcohol to the corresponding ketone. The aqueous solution may further comprise a base, such as an alkali metal hydroxide. In some embodiments, the base has a concentration within a range of from 0.1-6 M, such as from 0.1-2 M, 0.5-2M, or 1-2 M. In some embodiments, the conditions effective to oxidize the compound comprise pairing the aqueous solution against an oxidizing catholyte mixture in an electrochemical cell to produce electrical energy, applying a voltage to the aqueous solution, exposing the compound to an oxygen source (e.g., air) or chemical oxidant (e.g., 02), or a combination thereof. An exemplary mechanism for oxidation of a compound according to formula IA is shown in FIG. 30.

V. REPRESENTATIVE EMBODIMENTS

Several representative embodiments are described in the following paragraphs.

An aqueous anolyte, comprising: a fluorenone derivative or a salt thereof having a structure according to any one of formulas I-III:

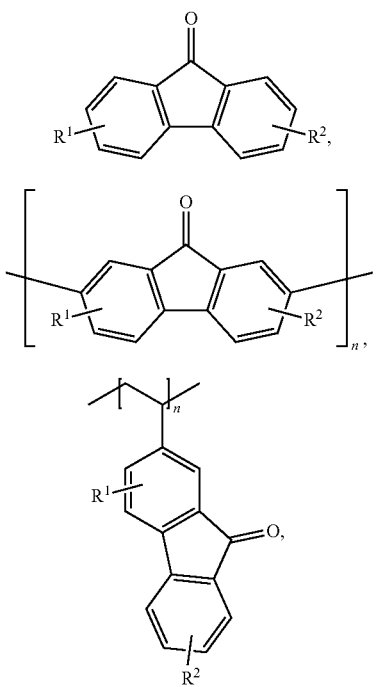

where $R^1$ and $R^2$ independently are an electron withdrawing group, and n is an integer >1; a base; and water. In some embodiments, the compound is not 7-nitro-9-oxo-9H-fluorene-2-carboxylic acid, 7-nitro-9-oxo-9H-fluorene-4-carboxylic acid, or 5-nitro-9-oxo-9H-fluorene-4-carboxylic acid.

The aqueous anolyte of the preceding paragraph, wherein $R^1$ and $R^2$ independently are $SO_3^-$, $CO_2^-$, $CF_3$, or $NO_2$.

The aqueous anolyte of the first paragraph where $R^1$ and $R^2$ independently are $SO_3^-$ or $CO_2^-$.

The aqueous anolyte of any one of the preceding paragraphs, wherein $R^1$ is $SO_3^-$.

The aqueous anolyte of the preceding paragraph, wherein $R^2$ is $SO_3^-$ or $CO_2^-$.

The aqueous anolyte of any one of the preceding paragraphs, wherein the fluorenone derivative is asymmetric.

The aqueous anolyte of the first paragraph, wherein the fluorenone derivative comprises

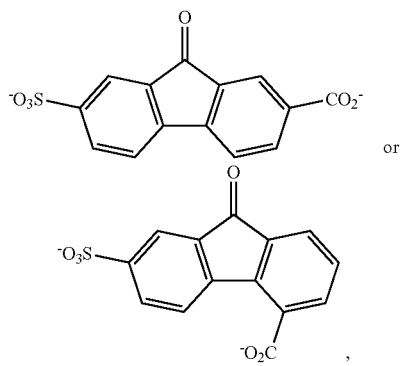

or a salt thereof.

The aqueous anolyte of any one of the preceding paragraphs, wherein the base comprises an alkali metal hydroxide.

The aqueous anolyte of any one of the preceding paragraphs, wherein the fluorenone derivative has a concentration within a range of from 0.5 M to 1.5 M.

The aqueous anolyte of the preceding paragraph, wherein the fluorenone derivative has a concentration within a range of from 1.0 M to 1.5 M.

The aqueous anolyte of any one of the preceding paragraphs, consisting essentially of the base, the fluorenone derivative, and water.

An aqueous electrolyte system for a redox flow battery system, comprising: an aqueous anolyte according to any one of the preceding paragraphs; and an aqueous catholyte comprising an electrochemically active material.

The aqueous electrolyte system of the preceding paragraph, wherein the aqueous catholyte comprises: $K_4Fe(CN)_6$, $K_3Fe(CN)_6$, or a combination thereof; and water.

The aqueous electrolyte system of either of the preceding two paragraphs, wherein the aqueous catholyte further comprises a base or an acid.

The aqueous electrolyte system of any of the preceding three paragraphs, wherein: the aqueous anolyte comprises an alkali metal hydroxide and

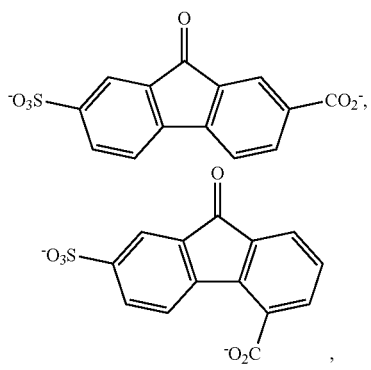

or a combination thereof; and the aqueous catholyte comprises an alkali metal hydroxide and $K_4Fe(CN)_6$, $K_3Fe(CN)_6$, or a combination thereof.

The aqueous electrolyte system of the preceding paragraph, wherein the aqueous anolyte comprises the alkali metal base and

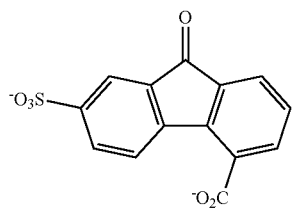

A redox flow battery system, comprising: the aqueous electrolyte system of any one of the preceding five paragraphs; and a separator.

The redox flow battery system of the preceding paragraph, further comprising a carbon-based anode and a carbon-based cathode.

VI. EXAMPLES

Materials and Methods

Chemicals and instruments: All chemicals were purchased from TCI, Sigma-Aldrich, Fisher scientific or AA Blocks, and used as received from commercial suppliers. NMR solvents were purchased from Cambridge Isotopes. Deionized water was used to make the electrolytes and was purged with nitrogen prior to use.

Nuclear magnetic resonance spectroscopy: NMR spectra were either collected on a 500 MHz NMR spectrometer system manufactured by Oxford at 25° C. (The system consists of an Oxford AS500 magnet connected to an Agilent Technologies console), or collected on a 400 MHz NMR spectrometer (Bruker 400 MHz Avance III NMR with NanoBay console, equipped with a SampleCase autosampler using IconNMR automation. Probe: BBFO 5 mm Smart-Probe). Chemical shifts were reported in ppm with the solvent resonance as the internal standard (DMSO, δ=2.50; D2O, δ=4.70).

Mass spectroscopy: MS analysis was performed using a 15 T Fourier transform ion cyclotron resonance mass spectrometer (FTICR-MS) (Bruker SolariX) outfitted with a standard electrospray ionization (ESI) interface.

Electron paramagnetic resonance spectroscopy: All EPR measurements were performed on a Bruker ELEXSYS E580 spectrometer at 298 K. The electrolyte solution sample was pulled into a glass capillary (VitroTubes™, ID 0.8 mm and OD 1 mm) using a Hamilton syringe connected through nanotight fittings from Valco Instruments Co. Inc. The capillary was sealed using Critoseal™ Leica Microsystems capillary tube sealant on both ends and was further placed inside a 4 mm EPR tube with the open end sealed inside a glove box filled with nitrogen. All samples were prepared inside the glove box immediately before EPR experiments to minimize the influence of air and moisture. The typical settings for the spectra were microwave frequency=9.324 GHz, sweep time=41.94 s, time constant=5.12 ms, power=0.02 mW, field modulation amplitude=0.05 G, and sweep width=24 G for dilute solutions in order to capture the detailed hyperfine structures but the sweep width was increased to 50 G for relatively concentrated solutions to incorporate their broader line widths. Absolute spin concentrations of the samples were determined by calibration curves of the spin standard TEMPO (2,2,6,6-tetramethyl-1-piperidinyloxyl) with concentrations varying from 0.01 mM to 100 mM, and another spin standard 4-Hydroxy-TEMPO with concentrations varying from 0.1 M to 1.0 M.

Battery performance: All battery performance tests were performed under $N_2$-atmosphere purge box (PLAS-LABS) except specified condition.

EPR Measurements: All EPR measurements were performed on a Bruker ELEXSYS E580 spectrometer at 298 K. The electrolyte solution sample was pulled into a glass capillary (VitroTubes™, ID 0.8 mm and OD 1 mm) using a Hamilton syringe connected through nanotight fittings from Valco Instruments Co. Inc. The capillary was sealed using Critoseal™ Leica Microsystems capillary tube sealant on both ends and was further placed inside a 4 mm EPR tube with the open end sealed inside a glove box filled with nitrogen. All samples were prepared inside the glove box immediately before EPR experiments to minimize the influence of air and moisture. The typical settings for the spectra were microwave frequency=9.324 GHz, sweep time=41.94 s, time constant=5.12 ms, power=0.02 mW, field modulation amplitude=0.05 G, and sweep width=24 G for dilute solutions in order to capture the detailed hyperfine structures but the sweep width was increased to 50 G for relatively concentrated solutions to incorporate their broader line widths. Absolute spin concentrations of the samples were determined by calibration curves of the spin standard TEMPO (2,2,6,6-tetramethyl-1-piperidinyloxyl) with concentrations varying from 0.01 mM to 100 mM, and another spin standard 4-Hydroxy-TEMPO with concentrations varying from 0.1 M to 1.0 M.

Electrochemical tests: CV measurements in aqueous phase were performed using a three-electrode configuration consisting of a glassy carbon working electrode (3 mm diameter), a glassy carbon counter electrode and an Ag/AgCl reference electrode. The electrolytes of 10 mM redox-active materials in 1.0 M NaOH were used. CV data were collected using a CHI760D potentiostat (CH Instruments) at a scan rate of 100 mV s$^{-1}$ (Hollas et al., Nature Energy 2018, 3:508-514). CV measurements in nonaqueous phase were performed using a three-electrode configuration consisting of a glassy carbon working electrode (3 mm diameter), a glassy carbon counter electrode and an Ag/AgNO$_3$ (10 mM in Acetonitrile) as reference electrode or Ag wire as pseudo reference electrode (Inzelt et al., Handbook of Reference Electrodes, 2013, Springer). Tests were carried out in an argon-filled Mbraun glove box (Stratham, N.H., USA).

Flow cell tests: The flow cell (Hollas et al., Nature Energy 2018, 3:508-514) used an interdigitated design with an active area of 10 cm$^2$ with stacked layers of ELAT (Nuvant) and CP-ESA (SGL) electrodes on each side sandwiching a Nafion membrane (NR212). The NR212 membranes were treated with 1 M NaOH at 25° C. for 8 h to convert to Na$^+$ forms. Alternative carbon paper (FreudenbergH23) was used for 0.5 M flow cell cases. A Masterflex L/S peristaltic pump (Cole-Parmer) was used to circulate the electrolytes through the electrodes at a flow rate of 60 ml min$^{-1}$. The flow cell was galvanostatically charged/discharged at room temperature on an Arbin BT-2000 battery tester (Arbin Instruments) at room temperature between specified voltage limits at specified current. The electrolyte composition concentration was determined by amount of substance of active material at specified ratio. Due to solubility difference of anolyte and catholyte material, there is large volume difference between the two sides. A) For the 0.1 M flow cell, the electrolytes consisted of 1 mmol (0.1 M) anolyte combined with 1 equivalent of NaOH in 10 mL of 1 M NaOH and 3 mmol (0.3 M) K$_4$Fe(CN)$_6$/3 mmol (0.3 M) K$_3$Fe(CN)$_6$ catholyte in 10 mL of 1 M NaOH. Total Na+K cation concentration was 1.2 M on anolyte side and 3.1 M on catholyte side; B) For the 0.5 M flow cell, the anolyte contained 3 mmol (0.5 M) active material combined with 1 equivalent of NaOH in 6 mL of 1 M NaOH and the catholyte used 9 mmol (0.3 M) $K_4Fe(CN)_6$ and 9 mmol (0.3 M) $K_3Fe(CN)_6$ in 30 mL of 1 M NaOH. Total Na+K cation concentration was 2 M on anolyte side and 3.1 M on catholyte side; C) For the 1 M flow cell, the anolyte contained 6 mmol (1 M) active material combined with 1 equivalent of NaOH, dissolved with 2 M NaOH solution (total solution volume of 6 mL) and the catholyte used 22.5 mmol (0.3 M) $K_4Fe(CN)_6$ and 22.5 mmol (0.3 M) $K_3Fe(CN)_6$ in 75 mL of 1 M NaOH. Total Na+K cation concentration was around 4 M on anolyte side and 3.1 M on catholyte side; D) For the 1.36 M flow cell, the anolyte contained 7.5 mmol (1.36 M) active material combined with 1 equivalent of NaOH, dissolved with 1.1 M NaOH solution (total volume of 5.5 mL) and the catholyte used 22.5 mmol (0.3 M) $K_4Fe(CN)_6$ and 22.5 mmol (0.3 M) $K_3Fe(CN)_6$ in 75 mL of 1 M NaOH. Total Na+K cation concentration was around 3.1 M on anolyte side and 3.1 M on catholyte side. Battery demonstrated in FIGS. 15-17 used CP-ESA as electrode; E) For the 0.5 M/low base flow cell, the anolyte contained 3 mmol (0.5 M) active material combined with 1 equivalent of NaOH in 6 mL of 0.1 M NaOH and the catholyte used 9 mmol (0.3 M) $K_4Fe(CN)_6$ and 9 mmol (0.3 M) $K_3Fe(CN)_6$ in 30 mL of 0.1 M NaOH. Total Na+K cation concentration was 1.1 M on anolyte side and 2.2 M on catholyte side; F) For the 1 M/atmospheric environment flow cell, the anolyte contained 6 mmol (1 M) active material combined with 1 equivalent of NaOH, dissolved with 1 M NaOH solution (total solution volume of 6 mL) and the catholyte used 22.5 mmol (0.3 M) $K_4Fe(CN)_6$ and 22.5 mmol (0.3 M) $K_3Fe(CN)_6$ in 75 mL of 1 M NaOH. Total Na+K cation concentration was around 3 M on anolyte side and 3.1 M on catholyte side. The electrolyte solution was prepared with degassed DI water. The battery was assembled in atmosphere without further de-O2 treatment; G) For the 1 M/elevated temperature flow cell, the anolyte contained 6 mmol (1 M) active material combined with 1 equivalent of NaOH, dissolved with 1 M NaOH solution (total solution volume of 6 mL) and the catholyte used 13.2 mmol (0.4 M) $K_4Fe(CN)_6$, 13.2 mmol (0.4 M) $Na_4Fe(CN)_6$, 3.3 mmol (0.1 M) $K_3Fe(CN)_6$ in 33 mL of 0.5 M NaOH and 0.5 M KOH. Total Na+K cation concentration was around 3 M on anolyte side and 4.5 M on catholyte side. Battery demonstrated in FIGS. 18 and 19 used FH23 as electrode. The electrolyte solution was prepared with degassed DI water. The battery was assembled in atmosphere without further deoxygenation treatment. The electrolyte reservoir was sealed with PTFE tape, parafilm, and packing tape. The whole cell was operated inside controlled temperature oven with forced air circulation.

H/D exchange study: The 4C7SFL-OH used for H/D studies was prepared electrochemically in $H_2O$. Two samples were prepared in analogous manners in a nitrogen-filled purge box: 0.1 M and 1 M 4C7SFL-OH solution were prepared using either 1M NaOH in $D_2O$ or pure $D_2O$. After three days, samples of each were analyzed by $^1H$ NMR.

Solubility test: The dissolving solvent was added drop by drop to 1 mmol of testing powder with intermittent agitation with VWR Vertex mixer, until all powder was dissolved. The total mass of the solution was recorded. A glass micro syringe was used to transfer 100 μL of the solution directly to a tared weight glass vial for mass measurement. Specific gravity of the as-obtained solution was calculated, then the total volume of the as-obtained solution was calculated using calculated density and recorded total solution mass. Last, molarity was calculated based on calculated total solution volume (Duan et al., ACS Energy Letters 2017, 2:1156-1161).

Density-functional theory calculation: The DFT calculations were performed at Generalized Gradient Approximation functional with Grimme dispersion corrections (PBE-D3) and all-electron triple-zeta double polarization function basis set (TZ2P) inbuilt of ADF2019 software package. The implicit dielectric continuum (COSMO) model with water as solvent was used for geometry convergence and property calculations. The charge density distributions are based on the Coulombic potential derived from the SCF cycle of optimized geometry. It should be noted that in the COSMO model, an implicit solvation model considers the solvent as a continuous isotropic medium with an underlying assumption that it can sufficiently represent equivalent properties of the realistic solvation effect. Because of the lack of published values for the dielectric properties of 1 M NaOH, we adopted the traditional water-based COSMO model. Nevertheless, as the same assumption was made for all molecules that were tested, the predicted results should reflect the trend. The redox potential was calculated based on change in Gibbs free energy of the respective redox reaction (Leonat et al., *UPB Sci. Bull. Ser. B*2013, 75:111-118). The absolute hydration free energy of the solvated proton and electron were −262.4 and −37.5 kcal mol$^{-1}$, respectively (Tissandier et al., *J Phys Chem A* 1998, 102:7787-7794).

Example 1

DFT Calculations and Cyclic Voltammetry

Figure 6:
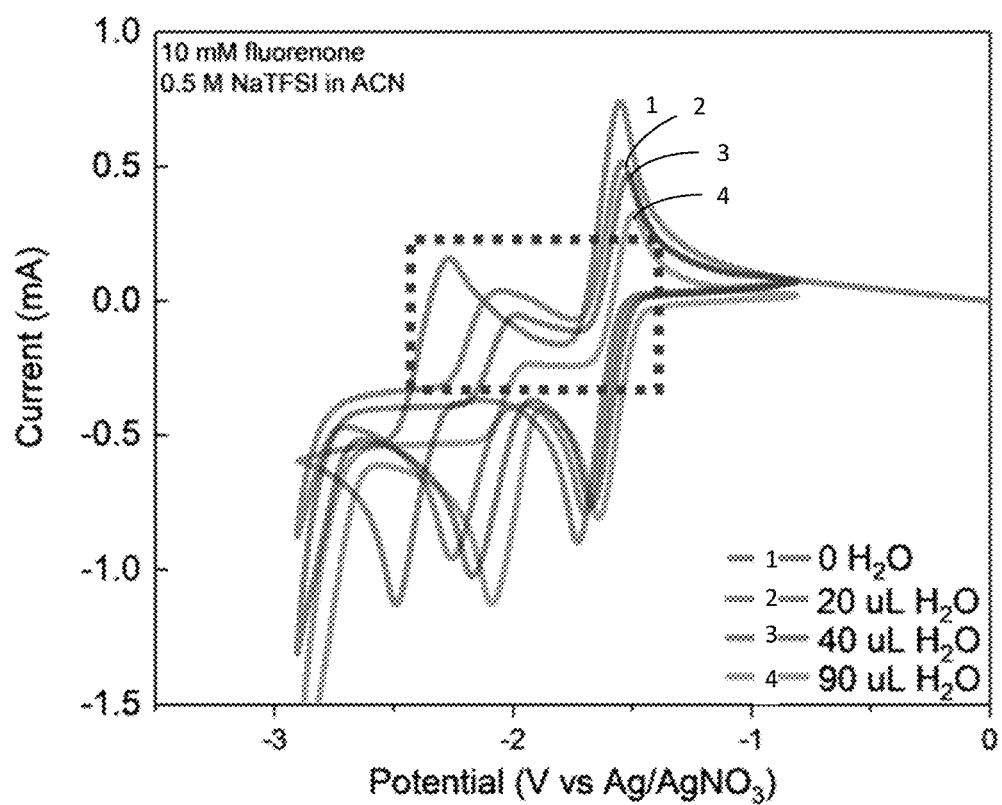
FIG. 6 is a cyclic voltammogram of 10 mM fluorenone and 0.5 M NaTFSI in acetonitrile (ACN) with varying amounts of water at 100 mV/s scan rate.
Figure 7:
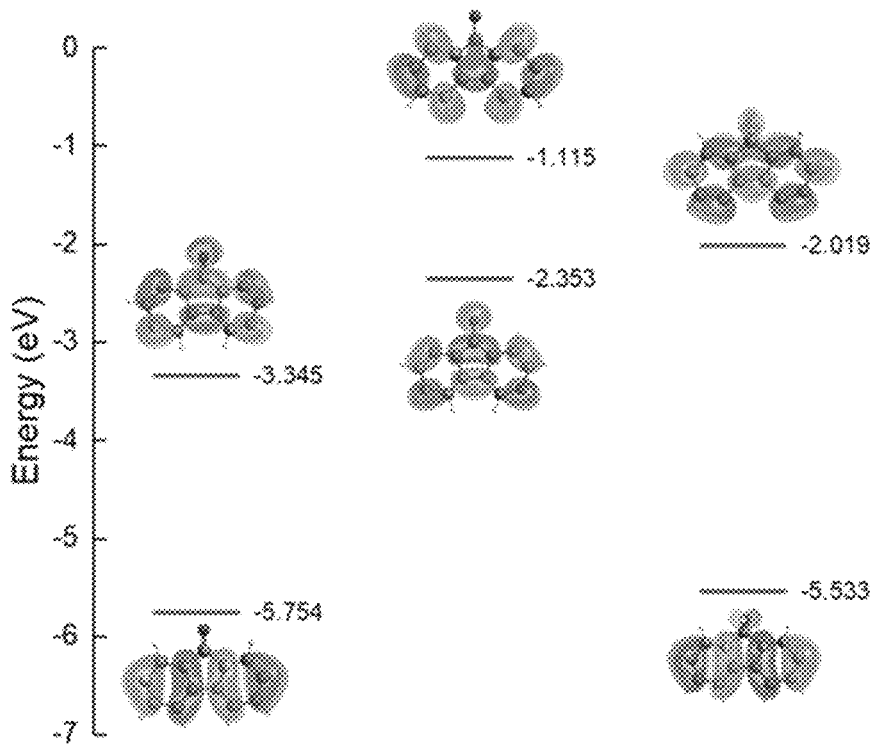
FIG. 7 shows the results of density-functional theory (DFT) calculations on LUMO and HOMO of fluorenone, dianionic fluorenol, and fluorenol.
Figure 8:
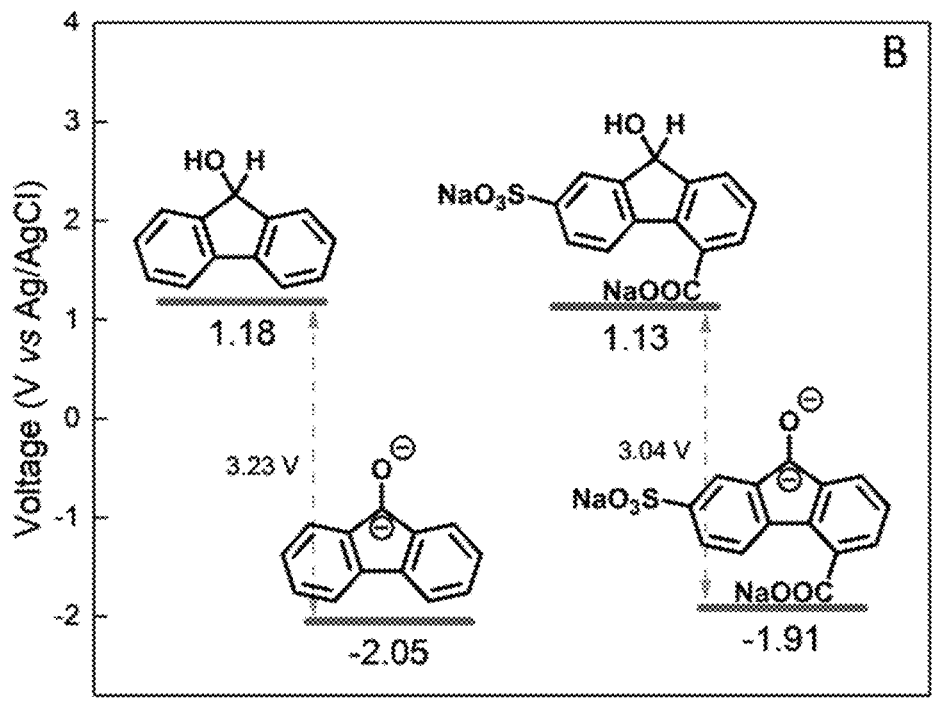
FIG. 8 shows the onset oxidation potential shifts of dianionic fluorenol and fluorenol as determined by DFT calculations.

By gradually introducing water as a proton source in acetonitrile containing 10 mM fluorenone (FL) and 0.5 M NaTFSI, the dianionic species oxidation peak of fluorenone was diminished at glass carbon surface (FIG. 6). The observed behavior raised the question of whether reversible oxidation of fluorenol could be enabled by achieving deprotonation during alcohol equilibrium with water. To provide theoretical support, the DFT calculation for the HOMO/LUMO energy gap and redox potential on dianionic species and fully protonated alcohol species was performed. In FIGS. 7 and 8, the deprotonated anionic species generated around 3V negative shifts on onset oxidation potential, which provides a suitable redox potential for an anolyte candidate.

Figure 9A:
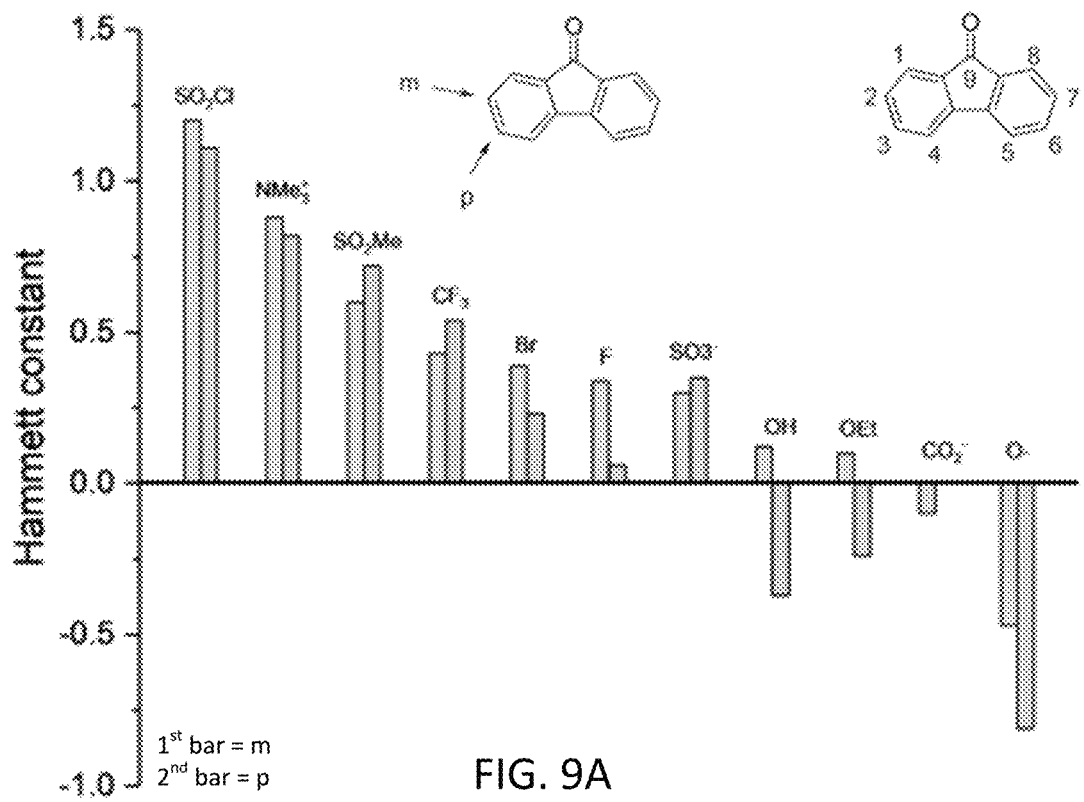
FIGS. 9A and 9B are a bar graph showing Hammett constants for various electron donating and electron withdrawing groups in the meta and para positions of fluorenone (9A) and a bar graph showing DFT calculations of fluorenol hydroxyl proton and benzylic proton pKa shifts with different substitutions (9B).
Figure 9B:
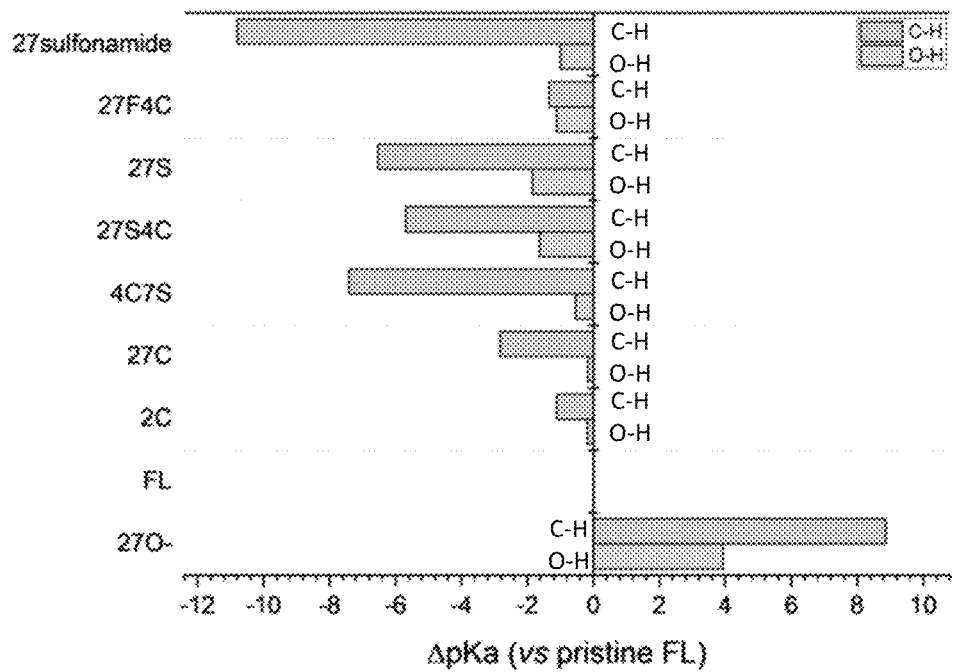
Figure 10:
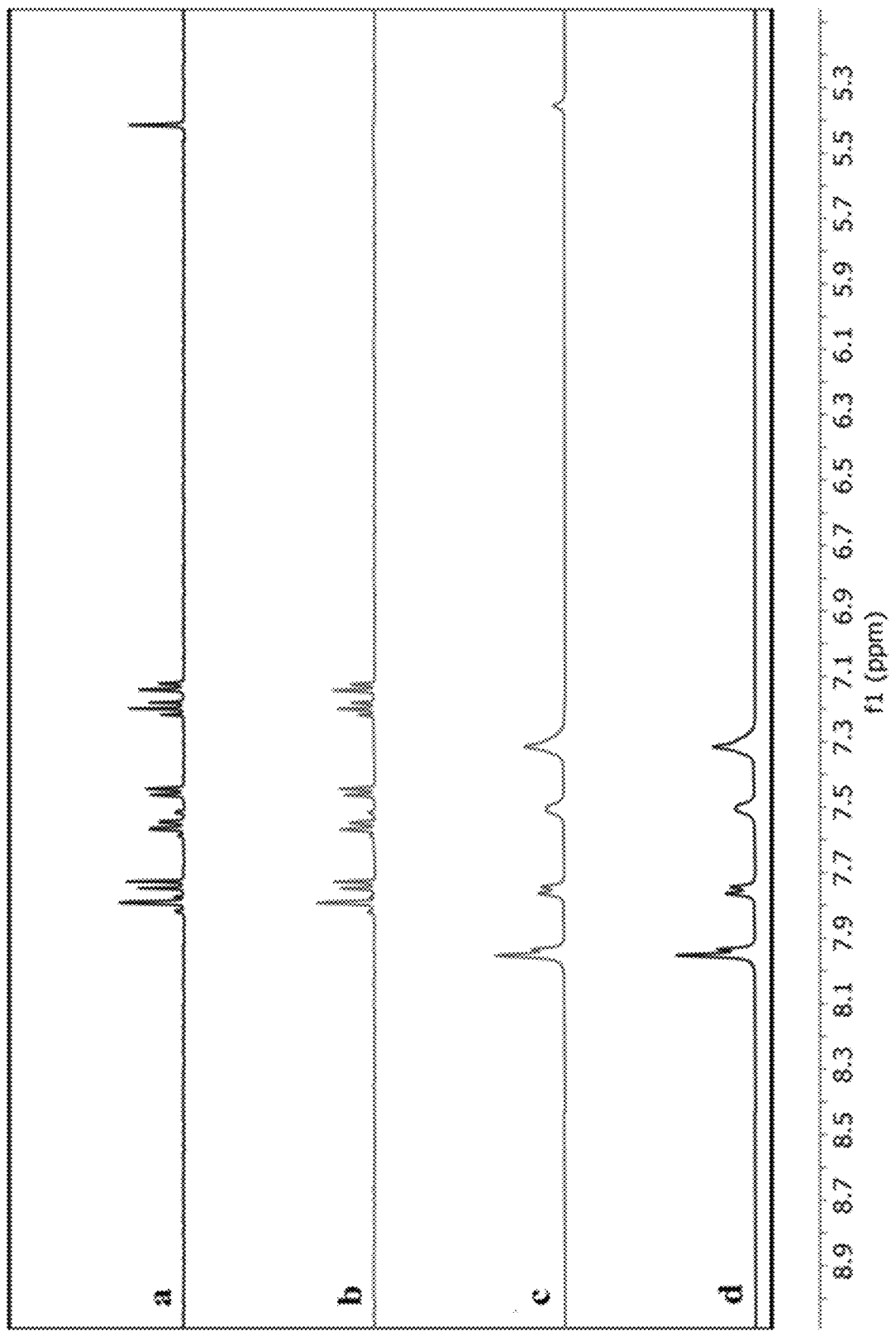
FIG. 10 is a series of NMR spectra collected in basic $D_2O$ showing de-protonation of 4C7SFL-OH, as indicated by H/D exchange of the C—H group in 1 M NaOH aqueous solution (fluorenol substituted with carboxylate at the 4 position and sulfonate at the 7 position).

Hammett constants of various electron withdrawing or donating groups in the meta (2,7) and para (3,6) positions of fluorenone are shown in FIG. 9A. Calculated pKa values of the protons in fluorenol (FL-OH) with different electron withdrawing or donating groups are listed in FIG. 9B where the numbers and letters indicate the substitutions, e.g., 27S4C indicates sulfonate groups at the 2 and 7 positions on the fluorenone and a carboxylate group at the 4 position. Structures of several of the compounds exemplified in FIG. 9 are shown in Table 1 supra. For each compound, the upper bar represents C—H (benzylic proton) and the lower bar represents O—H (hydroxyl proton). FIG. 9 demonstrated that the pKa of the hydroxyl proton shifted to the smaller values with stronger electron withdrawing groups, which represents easier deprotonation. The pKa of the C—H group decreased dramatically. Nuclear magnetic resonance (NMR) proton exchange experiments also supported that such deprotonation could happen in basic aqueous media. Deprotonation was demonstrated using the electrochemical synthesized alcohol 4C7SFL-OH at a concentration of 0.1 M. In $D_2O$, the C—H resonance appeared at 5.43 ppm. With 1 M NaOH in D$_2$O, the intensity of this peak diminished over 3 days, indicating a proton exchange (FIG. 10, traces a/b). Upon increasing material concentration to 1 M, the intensity of this peak diminished within 30 min and diminished over time (FIG. 10, traces c/d). The aromatic resonance shift with similar splitting pattern was attributed to high concentration and high salt environments. The proton peak diminishment was attributed to H/D exchange occurring via C—H deprotonation at different concentration.

Figure 11:
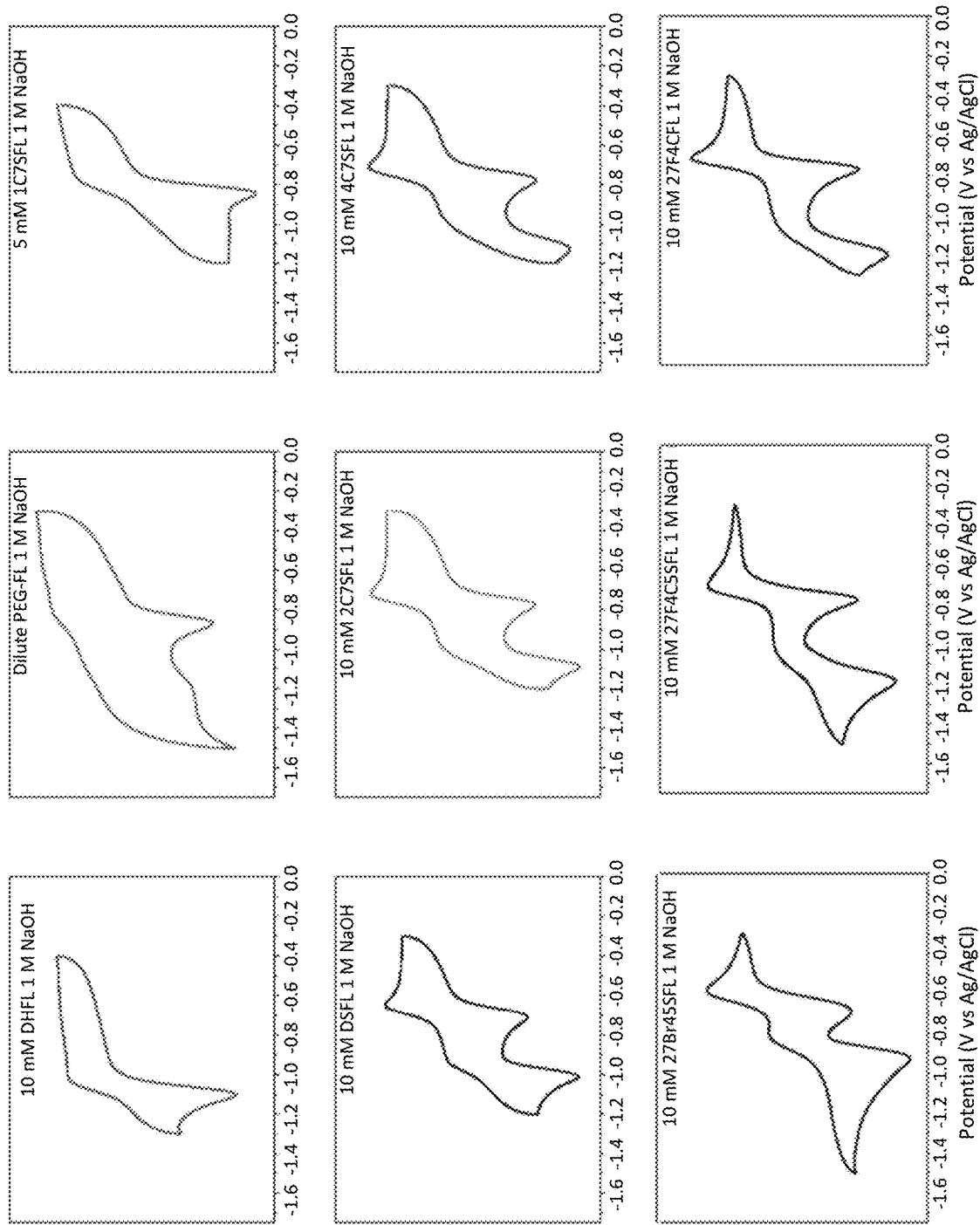
FIG. 11 is a series of cyclic voltammograms of fluorenone derivatives in 1 M NaOH.
Figure 12:
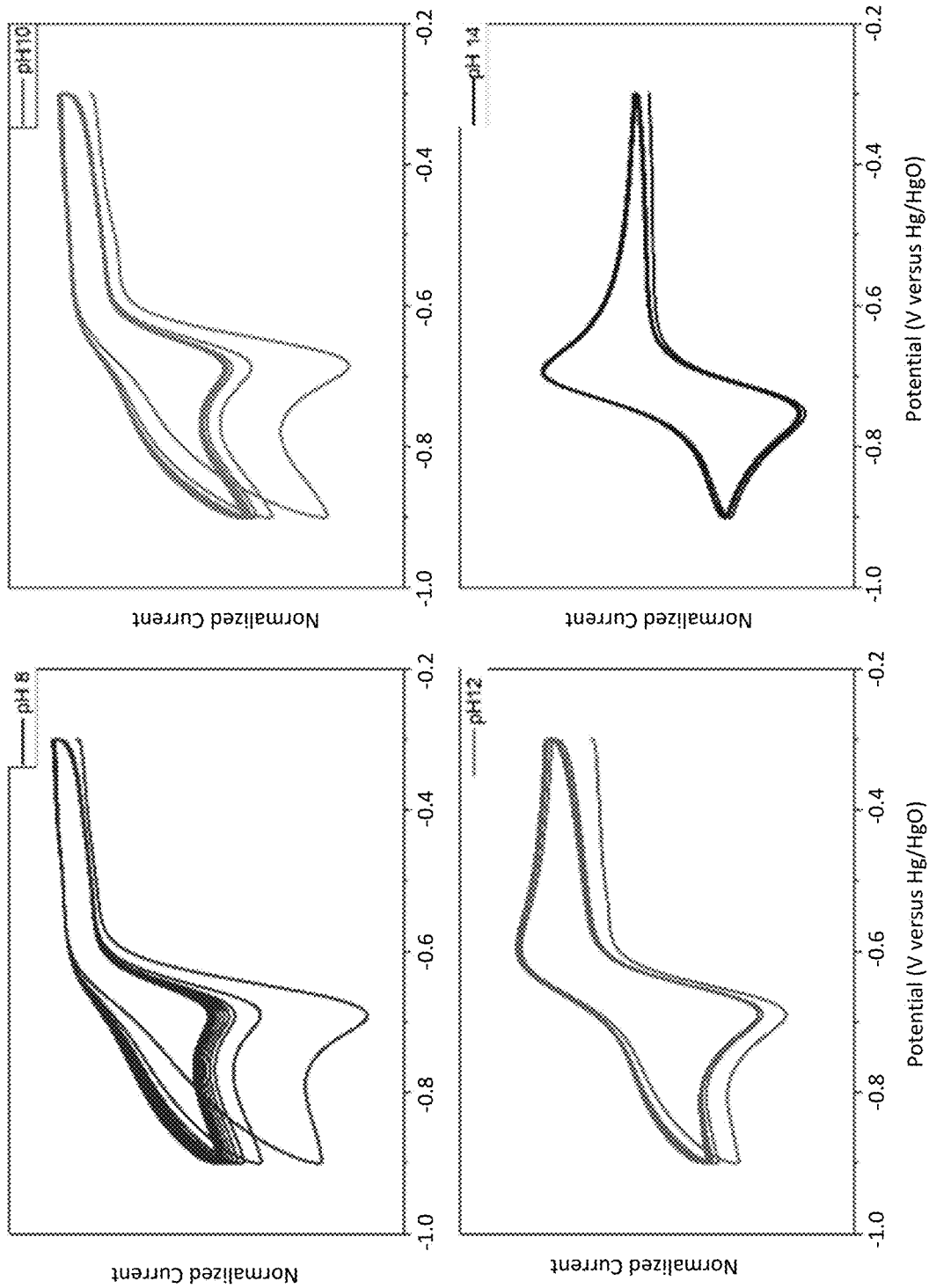
FIG. 12 is a series of cyclic voltammograms showing effects of pH on radical anion stability using DSFL (9-oxo-2,7-sulfo-9H-fluorene).
Figure 13A:
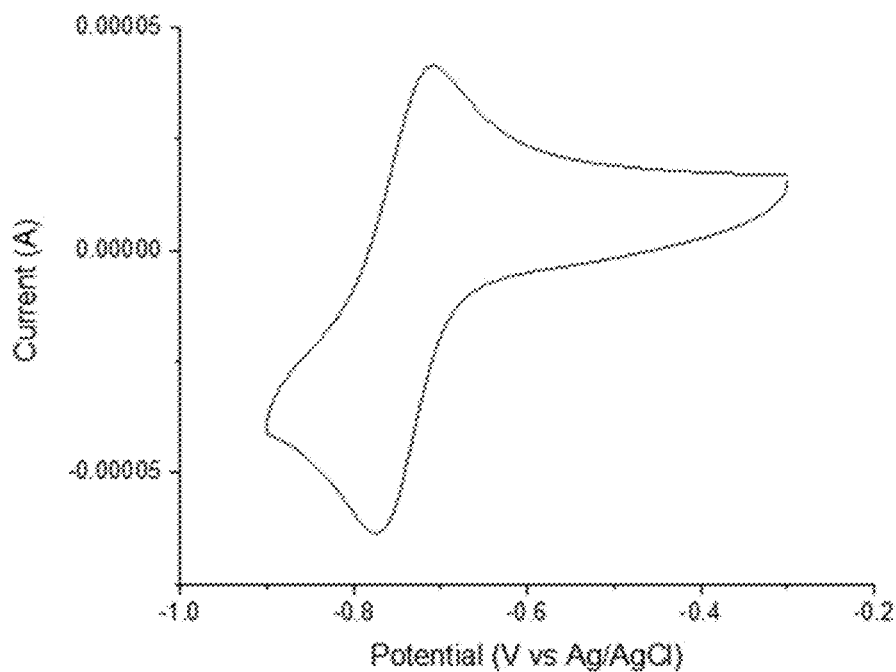
FIGS. 13A and 13B are cyclic voltammograms of 9-oxo-7-sulfo-9H-fluorene-4-carboxylic acid.
Figure 13B:
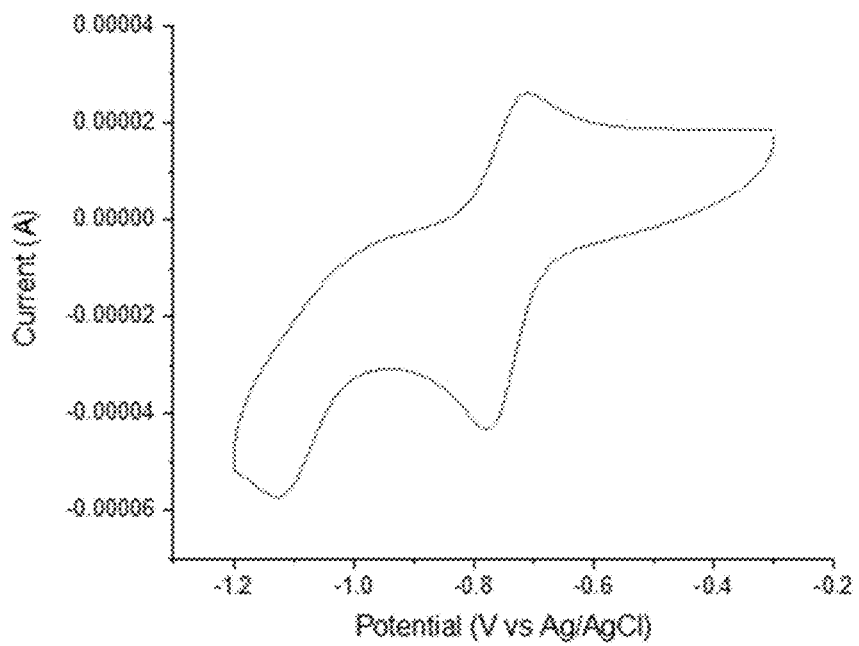

In view of the DFT calculation, it was theorized that functionalization of the FL ring structures with electron withdrawing groups such as —F, -sulfonamide, and —SO$_3$-, among others, would shift the equilibrium constant to increase the concentration of deprotonated FL-OH anion/dianion relative to FL-OH, thereby improving the two-electron redox-reversibility of FLs. As shown in FIG. 11, a series of FLs with various electron withdrawing or donating groups was evaluated to explore the effect of functional groups on the two-electron redox-reversibility of FLs by performing cyclic voltammetry in 1 M NaOH. DHFL (9-oxo-2,7-dihydroxy-9H-fluorene), which contains two —O$^-$ donating groups, displayed one reduction peak of carbonyl to the corresponding intermediate, which was rapidly protonated by water, resulting in an irreversible reaction. Sulfonate functionalized derivatives DSFL and 4C7SFL exhibited two separate one-electron reduction peaks and only one re-oxidation peak by cyclic voltammetry. This electrochemical behavior was consistent with the formation of a stable, reversible radical anion formed upon the first one-electron reduction, and eventual hydrogenation of the ketone upon the second reduction event, which showed minimal re-oxidation at the glassy carbon surface. 27BrDSFL showed some enhancement of hydrogenated alcohol re-oxidation even at glassy carbon surface. Alternatively, the 1C7SFL also showed irreversible reduction, due likely to intramolecular interaction between the generated alcohol group and the carboxylic group. As expected, the CV curves with two pairs of peaks become clear and sharp with adding stronger electron withdrawing groups. The results of pH testing using DSFL as a model molecule also supported the radical anion intermediate stability was highly dependent on aqueous media pH level (FIG. 12). Reversibility was seen only at high pH, which confirmed the hypothesis of deprotonation enabling reversible oxidation.

The solubilities of as-synthesized FLs in basic solution, 2 M NaOH/KOH, was investigated. The FLs with carboxylate (COO$^-$) and sulfonate (SO$_3$-) groups exhibited much higher solubilities than —O$^-$, and PEG groups, and the FLs with asymmetric structures had higher solubilities than symmetric structures (Table 2). For instance, highly symmetric DSFL showed less than 50 mM solubility in both 2 M NaOH solution and 2 M KOH solution; weak symmetric 2C7SFL exhibited the solubilities 1.1 M and 0.7 M in 2 M NaOH solution and 2 M KOH solution, respectively; however, highly asymmetric 4C7SFL revealed the highest solubilities of 1.5 M and 1.3 M in 2 M NaOH solution and 2 M KOH solution, respectively. Considering the two-electron redox reaction, the available electron concentration of 4C7SFL could reach close to 3 M. The solubility of 4C7SFL in 2 M NaOH can deliver a calculated volumetric capacity of 80.4 Ah/L with a complete two-electron transfer. The energy density is almost double that of a conventional vanadium electrolyte.

TABLE 2

| Compound | Solubility (M) | |
| --- | --- | --- |
| | 2M NaOH | 2M KOH |
| DHFL | N/A | N/A |
| DCFL | 0.04 | 0.9 |
| 2CFL | — | 0.8 |
| 4CFL | — | 0.65 |
| 27DSFL | — | — |
| 2C7SFL | 1.1 | 0.7 |
| 4C7SFL | 1.5 | 1.3 |
| 27S4CFL | 0.8 | — |
| PEG-FL | trace | trace |
| 27F4C5SFL | 0.15 | — |
| 27F4CFL | N/A | N/A |
| 27Br4SFL | trace | trace |

Notes:
1) DHFL solubility was 0.6M with 2 eq. NaOH in pure water.
2) 2CFL, 4CFL are literature data provided as a comparison (tested in KOH).
3) DSFL - disodium salt in pure water has solubility to up to 0.24M; the sulfonate exhibits a severe same ion effect leading to lower solubility in NaOH solution.
4) 27F4CFL solution formed clusters and aggregated without agitation; it formed up to a 1.4M transparent homogeneous solution with agitation but yielded copious precipitate after sitting overnight.
5) 27S4CFL in KOH was not tested; it was soluble up to 0.6M in pure of water (with 1 eq. NaOH).
6) 27Br45SFL was tested with a mixture mono- and di-sulfonated compounds in a ratio of around 1:3.
7) For trending, DCFL, DSFL, 2C7SFL, 4C7SFL, and 27S4CFL were good indicators of the asymmetry effect on solubility.

Example 2

Fluorenone Derivative Synthesis

The synthesis was modified based on previously reported synthetic routes (Chang et al., *Adv. Mater.* 2018, 30:1704234). Structures and abbreviations of the derivatives are shown in Table 1 supra. Several derivatives were synthesized from related precursors as shown below. For DSFL, 1C7SFL, 2C7SFL and 27Br4(5)SFL, a work-up procedure was applied following Chang et al. The reactions were conducted on 1-3 g scale. For 4C7SFL, 27S4CFL, 27F4CFL, 27F4C5SFL a work-up procedure is described below.

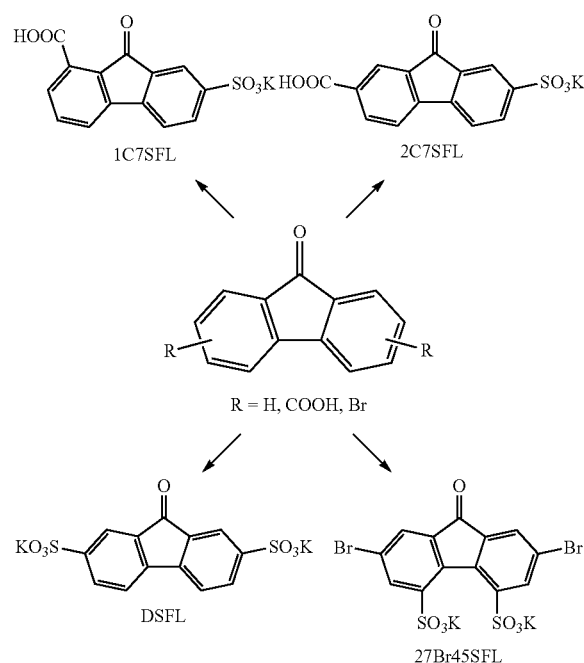

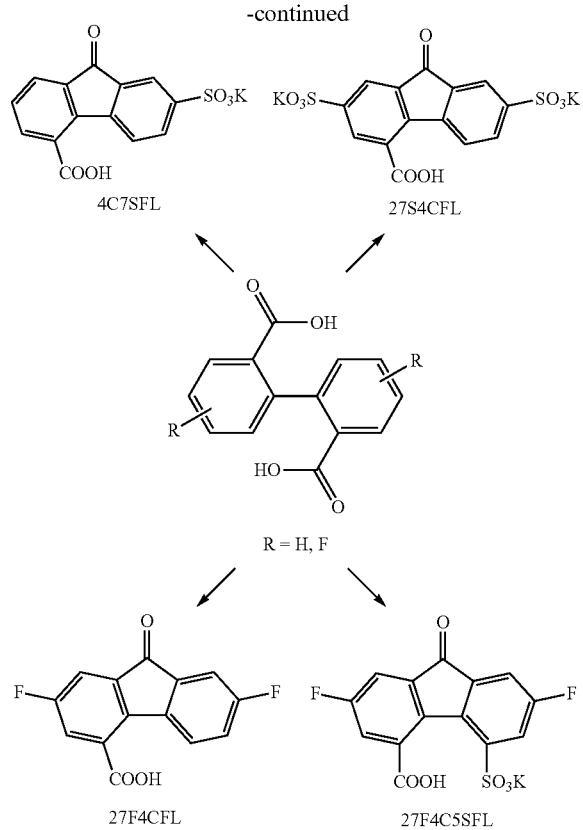

Starting material (33 mol, 8 g) was dissolved in 25 mL (3 mL/g starting material) of fuming sulfuric acid (18-23 wt %). The solution was stirred at 90° C. for 12 h-24 h (with longer reaction times necessary for disulfonated derivatives). The reaction was monitored by NMR until all starting material was reacted to desired product. Then the reaction mixture was worked up following the steps: A) The reaction mixture was cooled to room temperature and poured onto 100 g of ice. KOH (1 equiv) was added into the mixture. Yellow precipitate was vacuum filtered and dried under vacuum overnight. B) Yellow solid obtained was grinded into small pieces/powder, then dissolved with KOH (4 equiv) and minimum amount (around 25-30 mL) of $H_2O$. The solution was filtered, and the filtrate was acidified (pH~2-3) with conc. HCl (37%). Yellow precipitate was vacuum filtered and dried under vacuum overnight. C) Yellow solid obtained was grinded into small pieces/powder, then dissolved with a minimum amount (around 15-20 mL) of dimethyl sulfoxide (DMSO). The solution was filtered, and the filtrate was diluted with acetone. Yellow precipitate was vacuum filtered and dried under vacuum overnight. D) Yellow solid obtained was grinded into small pieces/powder, then stirred in acetone for ~4-5 h. Yellow fine powder was filtered by vacuum filtration and dried under vacuum overnight. The final product was dried in a vacuum oven at 60° C. overnight.

DSFL Yield: 70%. $^1$H NMR (500 MHz, DMSO-$d_6$) δ 7.83 (dd, J=7.6, 1.5 Hz, 2H), 7.77-7.73 (m, 4H). $^{13}$C NMR (126 MHz, DMSO-$d_6$) δ 192.70, 150.21, 143.80, 133.84, 132.71, 121.40, 121.35. ESI-HRMS m/z (M-K)$^{2-}$ calcd 168.98, obsd 168.98.

1C7SFL Yield: 97%. $^1$H NMR (500 MHz, DMSO-$d_6$) δ 7.92 (dd, J=7.5, 0.9 Hz, 1H), 7.85 (dd, J=7.7, 1.5 Hz, 1H), 7.81 (dd, J=7.7, 0.7 Hz, 1H), 7.73 (d, J=1.4 Hz, 1H), 7.67 (t, J=7.6 Hz, 1H), 7.44 (dd, J=7.7, 0.9 Hz, 1H). $^{13}$C NMR (126 MHz, DMSO-$d_6$) δ 194.07, 170.78, 153.33, 146.96, 145.99, 135.61, 135.43, 132.90, 131.30, 131.09, 125.96, 124.25, 124.17, 123.97. ESI-HRMS m/z (M-K)$^-$ calcd 303.00, obsd 303.00.

2C7SFL Yield: 99%. $^1$H NMR (500 MHz, DMSO-$d_6$) δ 8.19 (dd, J=7.7, 1.6 Hz, 1H), 8.04 (d, J=1.6 Hz, 1H), 7.94 (d, J=7.7 Hz, 1H), 7.88 (d, J=1.1 Hz, 2H), 7.78 (t, J=1.1 Hz, 1H). $^{13}$C NMR (126 MHz, DMSO-$d_6$) δ 191.65, 166.26, 150.61, 147.23, 142.75, 133.97, 133.59, 132.46, 131.73, 124.11, 124.00, 121.71, 121.54, 121.07. ESI-HRMS m/z (M-K)$^-$ calcd 303.00, obsd 303.00.

27Br45SFL $^1$H NMR (500 MHz, DMSO-$d_6$) δ 9.26 (s, 1H), 8.07 (d, J=2.0 Hz, 1H), 7.72 (dd, J=3.5, 2.0 Hz, 1H), 7.68 (s, 1H). ESI-HRMS m/z (M-2K)$^{2-}$ calcd 246.89, obsd 246.89, m/z (M-K)$^-$ calcd 532.74, obsd 532.74. Mixture of di-sulfonated and mono-sulfonated product (~3:1) was obtained.

27F4CFL Following the general procedure described above until Step B. In Step C, the obtained solid was dissolved with acetone. The solution was filtered, and the filtrate was diluted with water. Yellow precipitate was vacuum filtered and dried under vacuum overnight. Yield: 45%. $^1$H NMR (500 MHz, DMSO-$d_6$) δ 8.26 (dd, J=8.3, 4.6 Hz, 1H), 7.73 (dd, J=9.5, 2.7 Hz, 1H), 7.67 (dd, J=6.8, 2.7 Hz, 1H), 7.53-7.38 (m, 2H). $^{13}$C NMR (126 MHz, DMSO-$d_6$) δ 190.13, 167.12, 164.22, 163.21, 162.24, 161.22, 138.64, 137.99, 137.02, 130.09, 128.09, 122.33, 115.16, 111.99. ESI-HRMS m/z (M-H)$^-$ calcd 259.02, obsd 259.02.

27F4C5SFL Yield: 35%. $^1$H NMR (500 MHz, DMSO-$d_6$) δ 8.58 (d, J=6.1 Hz, 1H), 7.72-7.61 (m, 2H), 7.41 (d, J=8.0 Hz, 1H). $^{13}$C NMR (126 MHz, DMSO-$d_6$) δ 190.03, 167.19, 163.25, 161.26, 160.85, 158.82, 141.46, 137.86, 136.70, 130.26, 126.67, 122.17, 114.78, 112.63. ESI-HRMS m/z (M-K)$^-$ calcd 338.98, obsd 338.98.

4C7SFL Yield ranged from 55%-80% across different batches. $^1$H NMR (500 MHz, DMSO-$d_6$) δ 8.21 (d, J=8.0 Hz, 1H), 7.96 (d, J=7.8 Hz, 1H), 7.87-7.69 (m, 3H), 7.49 (t, J=7.6 Hz, 1H). $^{13}$C NMR (126 MHz, DMSO-$d_6$) δ 194.91, 171.01, 153.20, 145.60, 144.96, 139.19, 138.13, 136.53, 135.36, 132.56, 131.54, 129.73, 128.42, 123.94. ESI-HRMS m/z (M-K)$^-$ calcd 303.00, obsd 303.00.

27S4CFL Yield: 74%. $^1$H NMR (400 MHz, DMSO-$d_6$) δ 8.27 (d, J=8.1 Hz, 1H), 8.19 (d, J=1.7 Hz, 1H), 7.94-7.72 (m, 3H). $^{13}$C NMR (101 MHz, DMSO-$d_6$) δ 191.81, 167.93, 150.59, 149.75, 142.63, 142.45, 135.59, 134.42, 133.45, 132.73, 128.27, 126.11, 123.75, 121.31. ESI-HRMS m/z (M-2K)$^{2-}$ calcd 190.98, obsd 190.97.

PEG-FL The synthesis was modified based on previously reported synthetic routes (38). 2,7-dihydroxy-9H-fluoren-9-one (DHFL) (1 equiv) was mixed with anhydrous $K_2CO_3$ (4 equiv), NaI (0.15 equiv) and 2-(2-(2-chloroethoxy)ethoxy)ethan-1-ol (3 equiv) in DMF to achieve a 0.4 M DHFL suspension in a round bottom flask. The reaction mixture was refluxed at 135° C. and stirred overnight. Water (2 times of DMF volume) was then added to the reaction mixture, which was subsequently extracted with DCM (2 times of DMF volume) three times. The organic layer was dried over $Na_2SO_4$ and then condensed under vacuum to achieve crude product. Silica gel column chromatography (eluent: 97 v/v % dichloromethane+3 v/v % Methanol) was used to obtain the PEG-FL. Yield: 50%. $^1$H NMR (500 MHz, CDCl$_3$) δ 7.29-7.27 (m, 2H), 7.17 (d, J=2.4 Hz, 2H), 6.98 (dd, J=8.1, 2.5 Hz, 2H), 4.29-4.01 (m, 4H), 3.94-3.81 (m, 4H), 3.79-3.67 (m, 12H), 3.66-3.51 (m, 4H), 1.79 (s, 2H). $^{13}$C NMR (126 MHz, CDCl$_3$) δ 193.62, 159.13, 137.70, 135.92, 121.14, 120.58, 110.33, 72.47, 70.86, 70.37, 69.61, 67.91, 61.78. ESI-HRMS m/z (M-H)⁻ calcd 475.20, obsd 475.20.

4C7SFL-OH The synthesis was modified based on previously reported synthetic route for generic ketone reduction (39), or electrochemically using an H-cell similar to a previous report (40). Procedure for chemical method: To a stirred solution of 4C7SFL (5.8 mmol) in THF (~30 mL) was added NaBH$_4$ (4 equiv) at 0° C. in batches. Then the solution was stirred at room temperature for 24 h. After reaction, the mixture was cooled in iced water bath. To this solution was added a solution of saturated aqueous solution of NH$_4$Cl and then HCl (1 M) slowly. Precipitation was collected by vacuum filtrate, and the solid was dried under vacuum overnight. The product was extracted with DMSO-d$_6$ for NMR analysis. Alternatively, the product was extracted with DMSO. The solution was filtered, and the filtrate was diluted with acetone. White precipitate was vacuum filtered and dried under vacuum overnight. Procedure for electrochemical method: The bulk electrolysis used the same set-up as in a prior report (40). The experiment was conducted in an N$_2$-purged box. The set-up included an H-cell (equipped with a frit or Nafion 211, D=16 mm), and graphite felt strip as electrodes for both negative side and positive side (1 cm by 2 cm under solution surface, 3 mm thickness). 2 M NaOH was used as supporting electrolyte for anolyte side. Flow condition C in Method section was used for catholyte side (except 0.1 M NaOH was used in this case). Data were collected using an Arbin BT-2000 battery tester. The cell was charged at a constant current of 5 mA, with a cutoff limit of 1.8V, or capacity of calculated two-electron capacity, whichever comes first. After the electrolysis, the reaction mixture was transferred into a glass vial with pipette, acidified (pH~2-3) with 1 M H$_3$PO$_4$. Solvent was removed by evaporation under protection of N$_2$. The residue was extracted with DMSO-d$_6$ for NMR analysis. $^1$H NMR (500 MHz, DMSO-d$_6$) δ 8.26 (d, J=8.1 Hz, 1H), 7.76 (s, 1H), 7.50-7.38 (m, 3H), 7.18 (t, J=7.5 Hz, 1H), 5.79 (d, J=7.2 Hz, 1H), 5.34 (d, J=4.4 Hz, 1H). $^{13}$C NMR (126 MHz, DMSO-d$_6$) δ 171.75, 147.98, 146.87, 146.75, 139.60, 136.47, 134.97, 128.17, 126.54, 125.10, 124.19, 123.63, 121.80, 72.90. ESI-HRMS m/z (M-K)-calcd 305.01, obsd 305.01.

Example 3

Preparation and characterization of 9-oxo-7-sulfo-9H-fluorene-4-carboxylic Acid (4C7SFL)

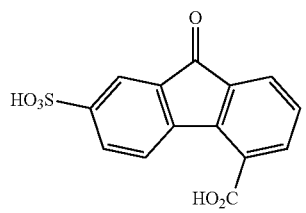 [SMILES: O=C(O)c1cccc2c1-c1ccc(S(=O)(=O)O)cc1C2=O]

9-Oxo-7-sulfo-9H-fluorene-4-carboxylic acid (alternatively referred to as 4C7SFL, 9-oxo-2-sulfo-9H-fluorene-5-carboxylic acid, or 5C2SFL) was synthesized from biphenic acid refluxed with 20% fuming sulfuric acid at 100° C. NMR showed near 100% conversion. With two times of purification, the recovery was 70%.

In alkaline conditions there was redox activity between the fluorenone and fluorenone radical and irreversible reduction from fluorenone to fluorenol at low concentrations of the 4C7SFL (see, e.g., FIG. 1). This type of behavior was also reflected in a battery while using low concentration anolyte material, in which case the battery was only able to discharge at low current density (2 mA/cm$^2$).

Figure 14:
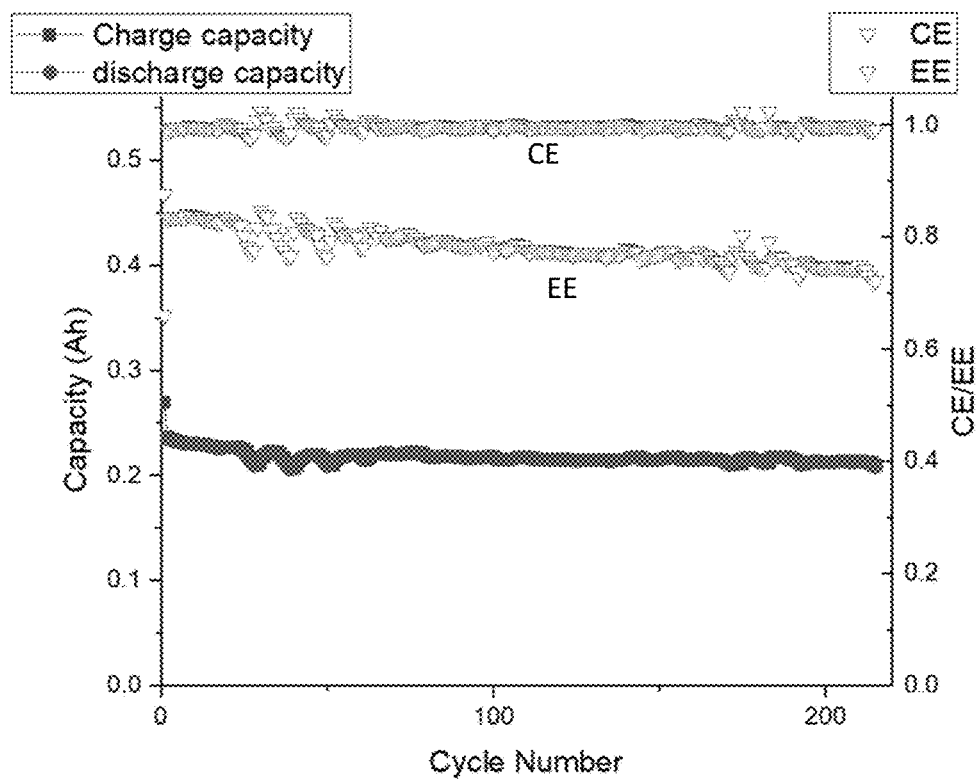
FIG. 14 shows battery performance over more than 200 cycles of an aqueous redox flow battery with an anolyte comprising 9-oxo-7-sulfo-9H-fluorene-4-carboxylic acid.

However, in a high concentration battery demonstration, 6 mL of anolyte solution containing 1M concentration of the 4C7SFL anolyte, was paired with an excess amount of catholyte solution containing 0.3M ferricyanide/0.3M ferrocyanide. An aqueous redox flow battery was assembled with an ELAT/ESA electrode and a Nafion© 212 separator. Conditions: anolyte, 6 mmol anolyte with 1 eq NaOH(s) dissolved with 2 M NaOH solution, total solution volume 6 mL; catholyte, 13.5 mmol ferricyanide/13.5 mmol ferrocyanide dissolved with 2 M NaOH, total solution volume 45 mL; Nafion© 212 membrane (pre-soaked in 2 M NaOH at room temperature overnight); charge rate, 20 mA/cm$^2$; pump flow rate, 60 mL/min. FIGS. 14A and 14B show cyclic voltammograms of 4C7SFL. FIG. 14 shows battery performance of the aqueous redox flow battery using 4C7SFL as the anolyte and ferri/ferrocyanide as the catholyte. The figure shows performance over more than 200 cycles. FIG. 14 shows stable cycling data with near 100% CE and near 80% EE, volumetric capacity of 39.3 Ah/L for the 1M 4C7SFL anolyte, and stable discharge process over 1 V across the time period at 20 mA/cm$^2$.

Figure 15:
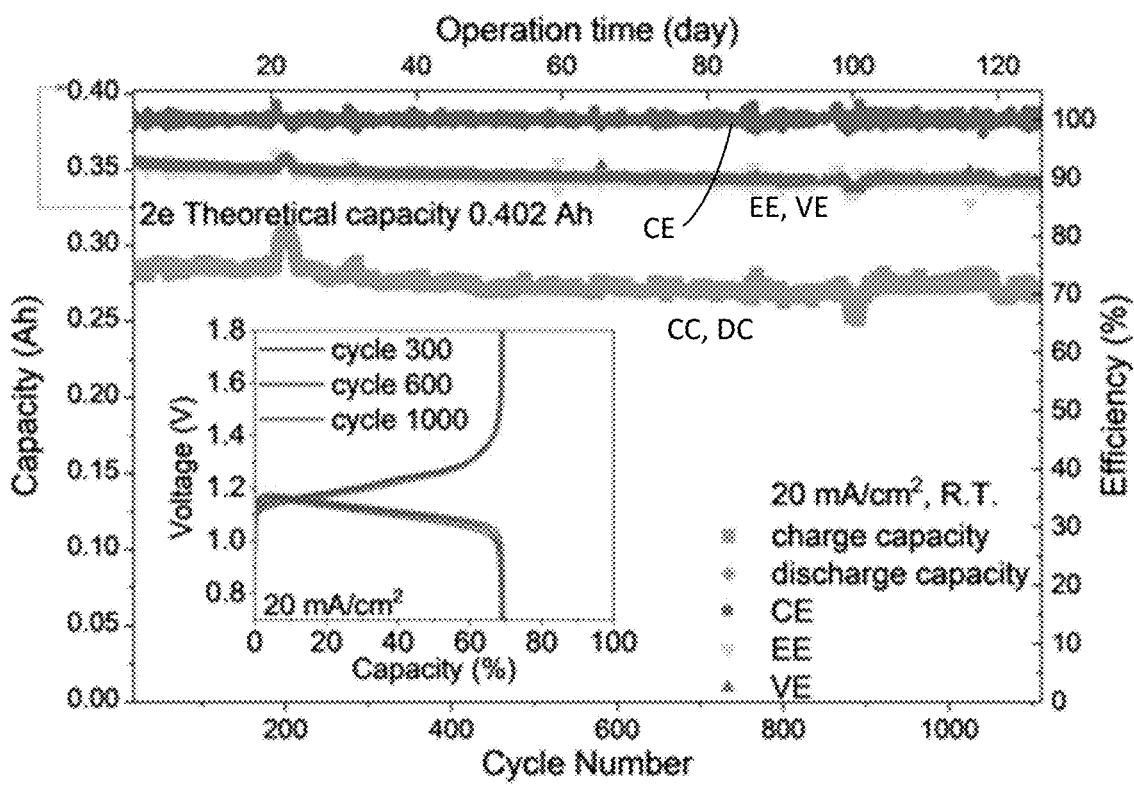
FIG. 15 shows results of an extended battery performance test over 120 days with an anolyte including 1.36 M 9-oxo-7-sulfo-9H-fluorene-4-carboxylic acid (4C7SFL) and a ferro/ferricyanide catholyte at room temperature and 20 mA/cm$^2$; the inset shows the polarization curves at selected cycles.
Figure 16:
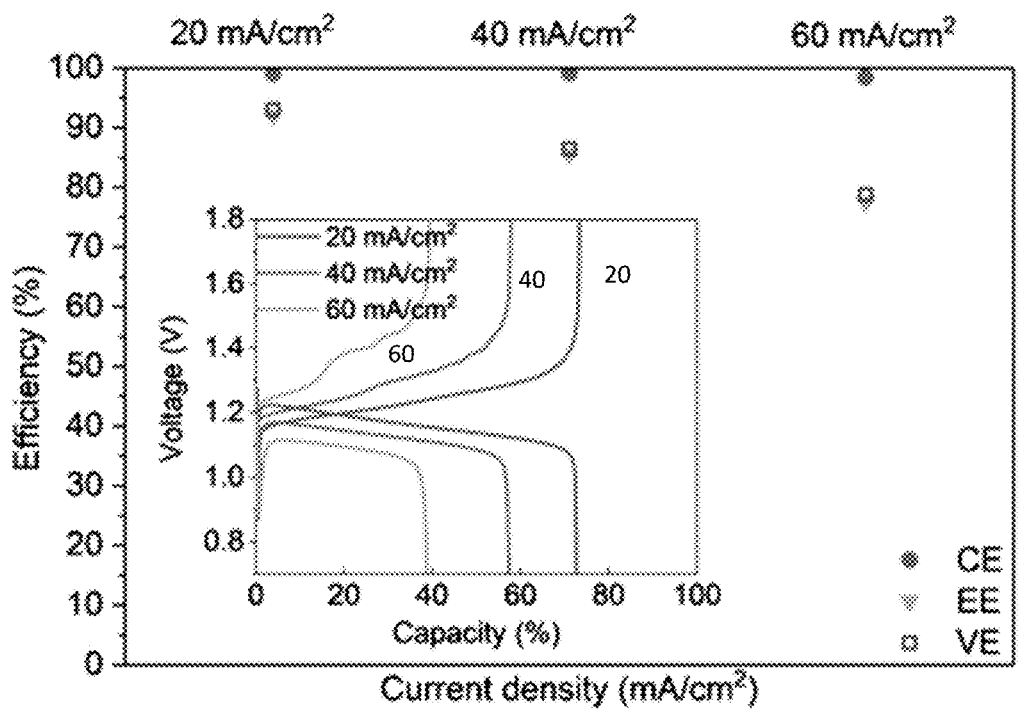
FIG. 16 shows efficiency and polarization curves of the battery of FIG. 15 at different current densities.
Figure 17:
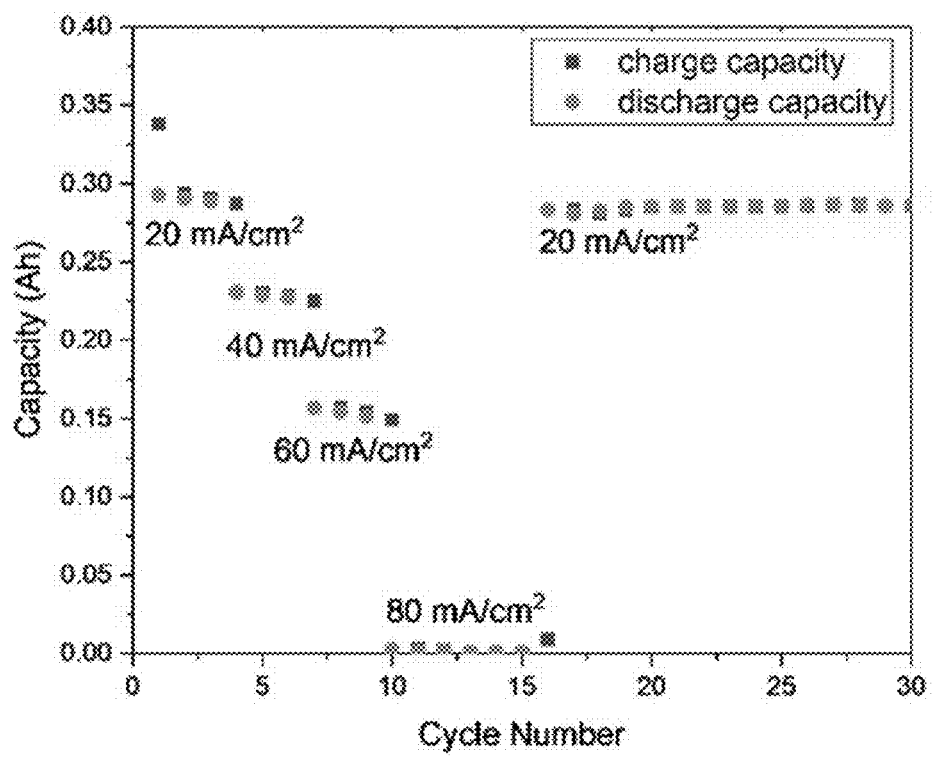
FIG. 17 is a graph of a current density performance test of the battery of FIG. 15 for an initial 30 cycles at room temperature.

A practical battery performance test was conducted with 4C7SFL anolyte and excess ferro/ferricyanide as the catholyte. Excess ferro/ferricyanide was used to avoid catholyte-derived capacity loss and allow long-term cycling of the fluorenone derivative. A flow battery consisting of ferro/ferricyanide catholyte solution and 1.36 M 4C7SFL anolyte solution (equivalent to 2.72 M electron transfer) was subjected to current density testing and extended cycling. The anolyte contained 7.5 mmol (1.36 M) active material combined with 1 equivalent of NaOH, dissolved with 1.1 M NaOH solution (total volume of 5.5 mL) and the catholyte used 22.5 mmol (0.3 M) K$_4$Fe(CN)$_6$ and 22.5 mmol (0.3 M) K$_3$Fe(CN)$_6$ in 75 mL of 1 M NaOH. The total Na+K cation concentration was around 3.1 M on anolyte side and 3.1 M on catholyte side. The results are shown in FIGS. 15-18. The capacity fluctuation observed during operation was attributed to variations in the operating temperature of the glove box. The average Coulombic efficiency (CE) was near 100% while a slight decrease of voltage efficiency (VE) was observed over extended cycling. As a result, the overall energy efficiency (EE) of the cell was approximately 90% for the majority of the cycles. The cell demonstrated >1 V discharge voltage at current densities from 20-60 mA/cm$^2$, though capacity utilization was significantly influenced by current density, consistent with kinetically limited fluorenol oxidation and coupled chemical reaction. Notably, at 20 mA/cm$^2$ current density, only a single charge/discharge plateau was observed, inconsistent with the stepwise reduction observed by CV. This phenomenon is a result of the disparate conditions of the flow cell and the CV, with a high concentration of 1.36 M in the flow cell leading to rapid dismutation of the charged species, producing fluorenol even before charging beyond 25% SOC. On the contrary, at 10 mM concentrations analyzed by CV, this second order dismutation process is slow enough to observe two separate reduction events. The low concentration battery also confirmed a noticeable plateau during charging process. Despite the limited utilization at higher current densities, the cell provided stable cycling at 20 mA/cm$^2$ for 120 days (1111 cycles), as shown in FIG. 15, with >96% reversible capacity delivered over 1 V during discharge throughout the cycling and 50% of discharge capacity point at ~1.10 V. The polarization curves of cycles 300 (day 35), 600 (day 69), and 1000 (day 113) reveal nearly identical operational discharge capacity, with most capacity loss observed during initial cycles. There was ~0.026% capacity fade (number calculated based on data of cycle 17 and cycle 1111, current density test was conducted between cycle 1 and cycle 16), calculating 0.00022%/day and 0.000024%/cycle, projecting 0.08%/year. This number was only a battery capacity fade reflection on the time-scale between continuous same-condition operation across 120 days at galvanic 20 mA/cm$^2$ battery charge/discharge. The observed battery capacity fade could be a result of multiple factors, such as internal resistance change, material cross-over, material degradation, and/or concentration change induced utilization change. The voltage profile and the efficiency data of the flow cell under various current densities are shown in FIG. 16. In the range of 20 to 60 mA cm$^{-2}$, the material utilization percentage (calculation based on two-electron transfer) and VE/EE both decrease with increasing current density; at a current density of 20 mA cm$^{-2}$ the utilization percentage was at 72%, VE at 93%, and EE at 92%, whereas at 60 mA cm$^{-2}$ they were at 38%, 79%, and 78%, respectively. Although the increasing current causes an increase in the polarization, differences in the equilibration rate between protonated and deprotonated species also contributes to the observed performance. Nevertheless, the modified 4C7SFL provides sufficient kinetics for reversible battery charge/discharge at a reasonable rate. A current density test was performed in the initial 15 cycles; detailed initial 30-cycle cycling data is provided in FIG. 17.

Figure 18:
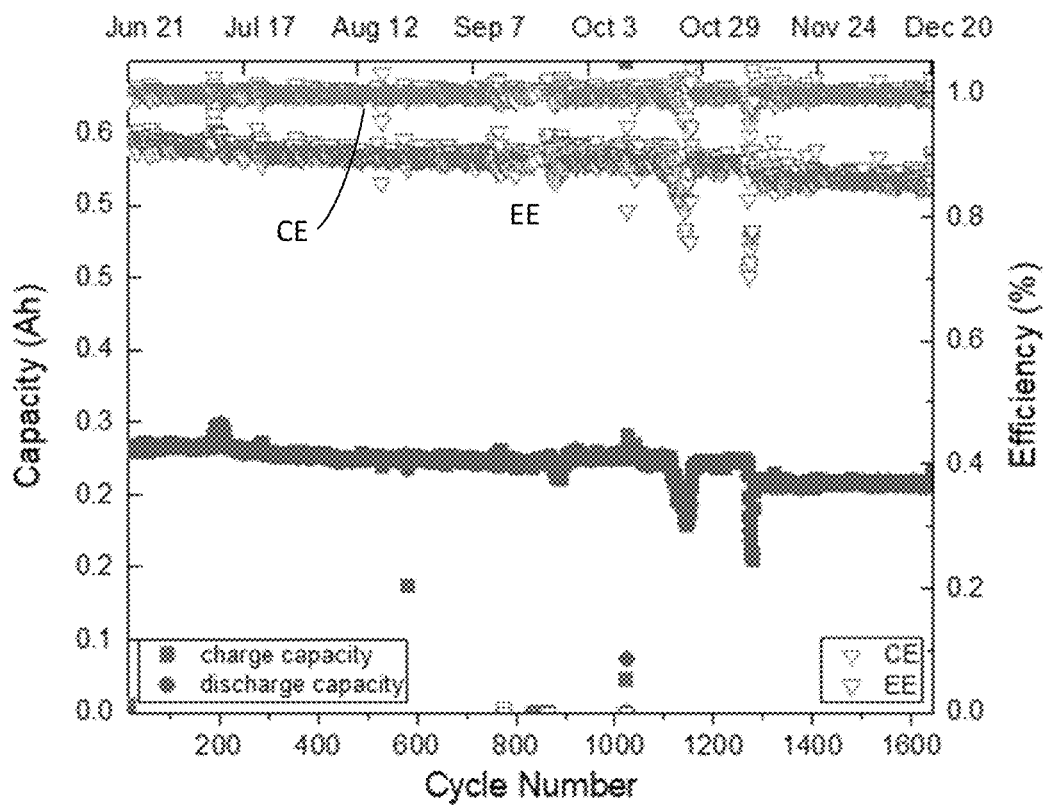
FIG. 18 shows results of an extended battery performance test over six months with an anolyte including 1.36 M 9-oxo-7-sulfo-9H-fluorene-4-carboxylic acid (4C7SFL) and a ferro/ferricyanide catholyte.
Figure 19:
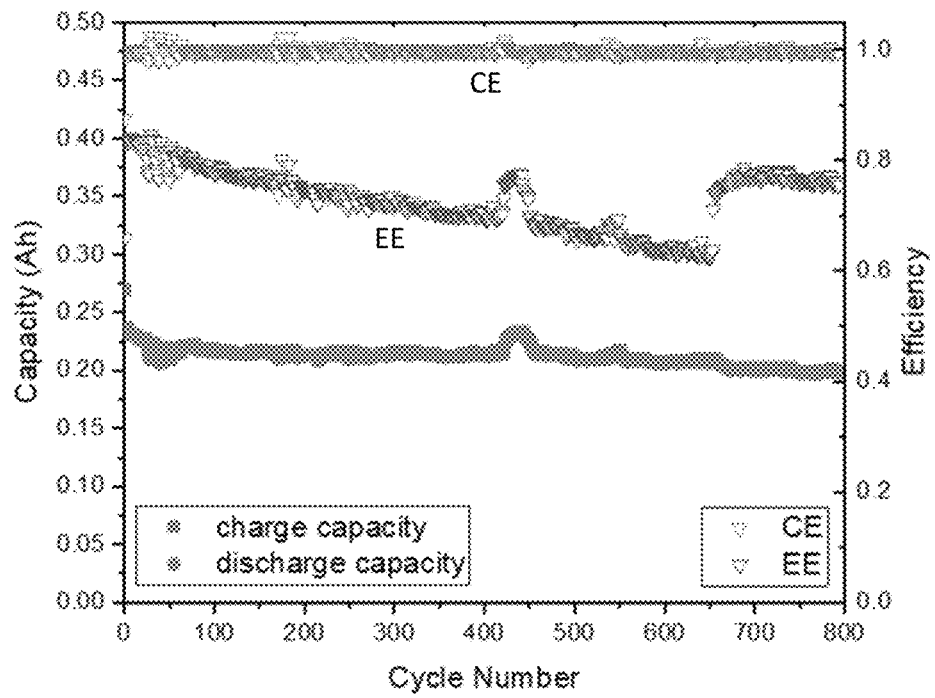
FIG. 19 shows results of an extended battery performance test over three months with an anolyte including 1 M 4C7SFL and a ferro/ferricyanide catholyte.
Figure 20:
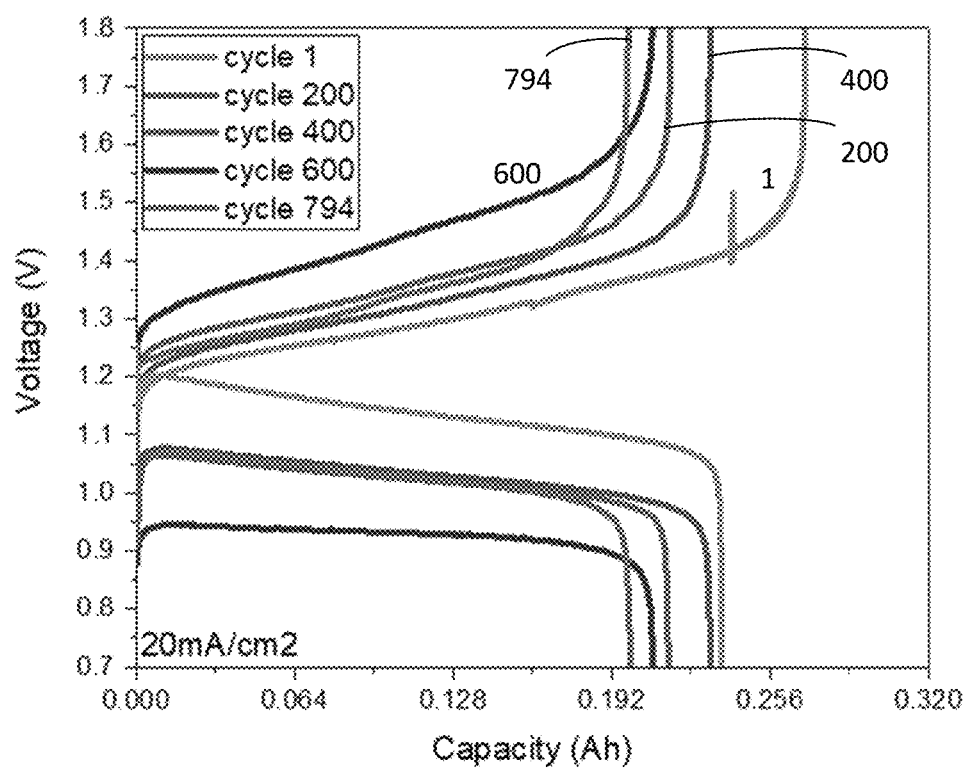
FIG. 20 shows the polarization curves of the battery of FIG. 19 at selected cycles.
Figure 21:
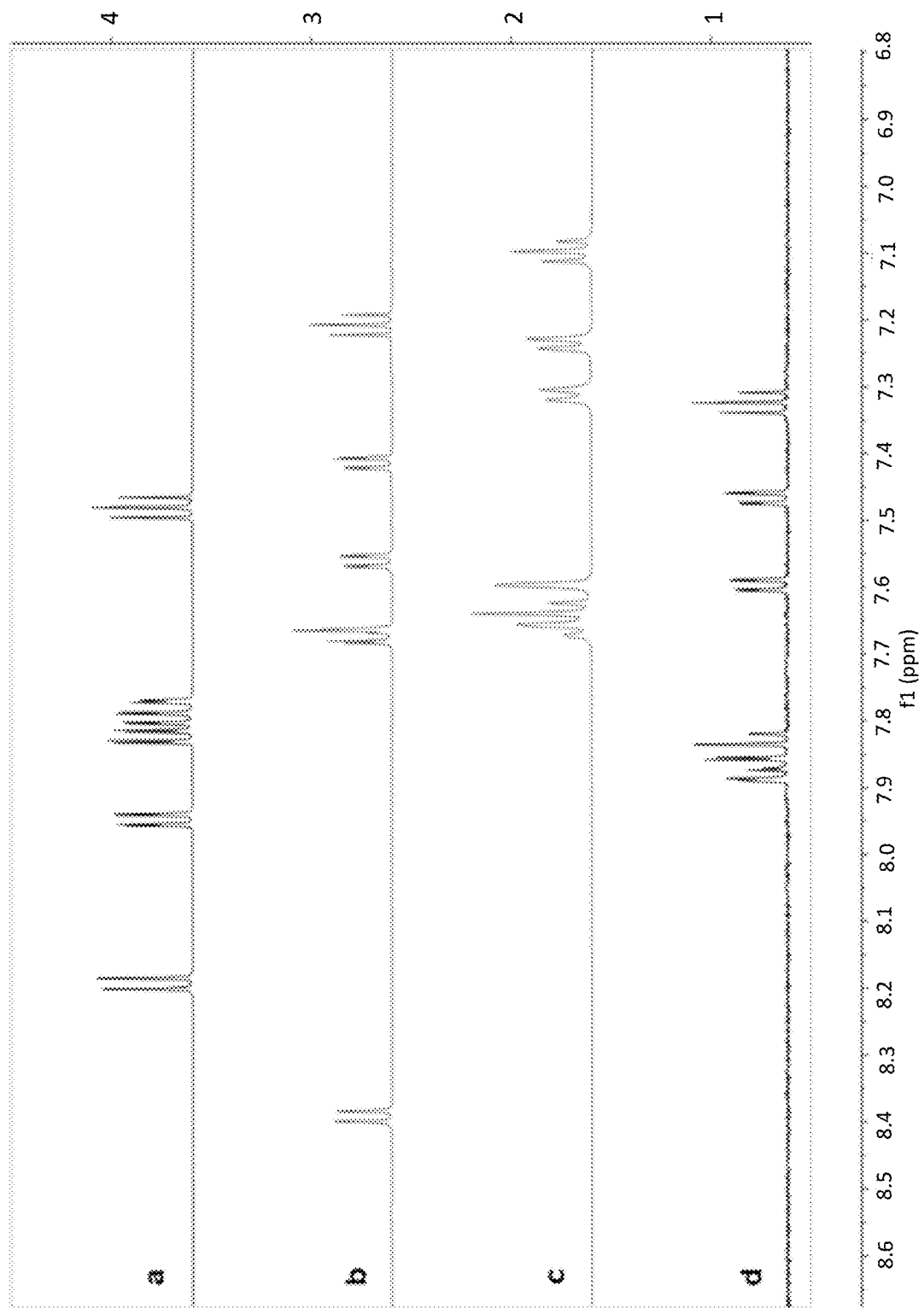
FIG. 21 shows an NMR spectrum of the anolyte of FIG. 19 after three months of cycling.
Figure 22:
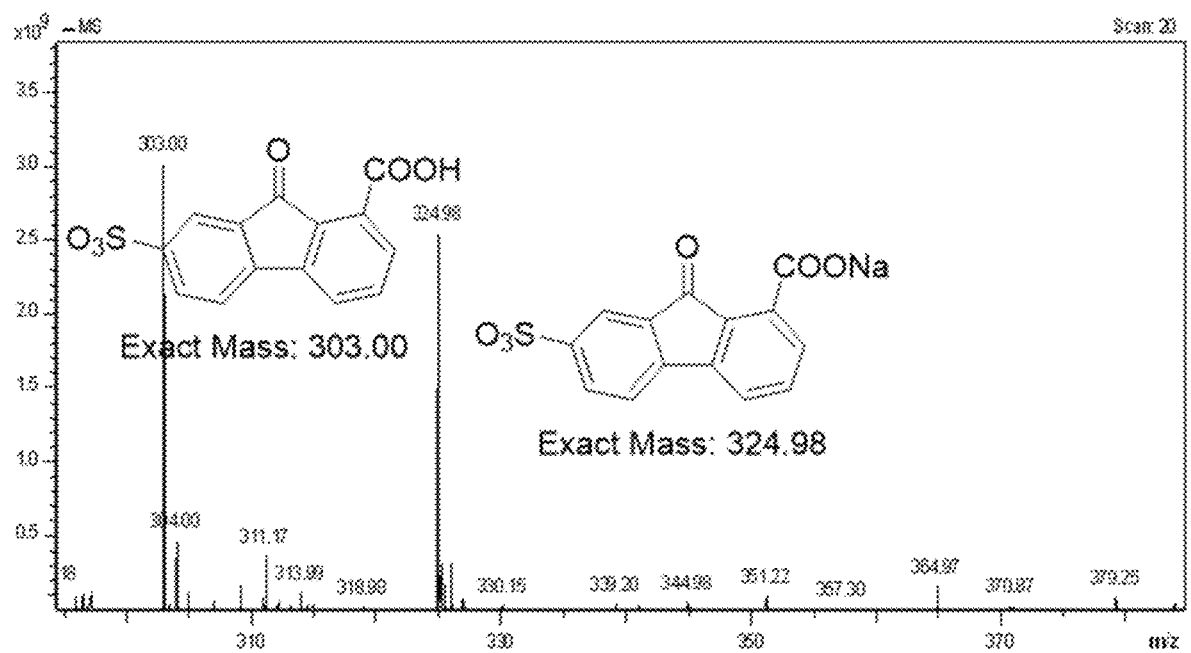
FIG. 22 shows a mass spectrum of the anolyte of FIG. 19 after three months of cycling.

An additional test was conducted for six months (FIG. 18). The post-cycling analysis after 6-month operation revealed small, yet observable new aromatic peaks attributed to de-sulfonation on the fluorenone core structure. The capacity decrease may be induced by the solid precipitation of 4C7SFL on carbon electrode surface/membrane, and loss of sulfonate group which resulted in lower utilization due to equilibrium favoring protonated alcohol over anionic species for discharge. Another 1 M battery operation of 3 months at 20 mA/cm$^2$ was subjected to post-analysis using allow current density discharge method and spectroscopic analysis to examine the material degradation. At about cycle 650, catholyte precipitation was noticed, and replaced with fresh catholyte. The results are shown in FIGS. 19 and 20. No material degradation was detected by NMR or mass-spectroscopy (FIGS. 21 and 22). Notably, for both batteries, at 20 mA/cm$^2$ current density, only a single charge/discharge plateau was observed, for the reasons previously stated.

Figure 23:
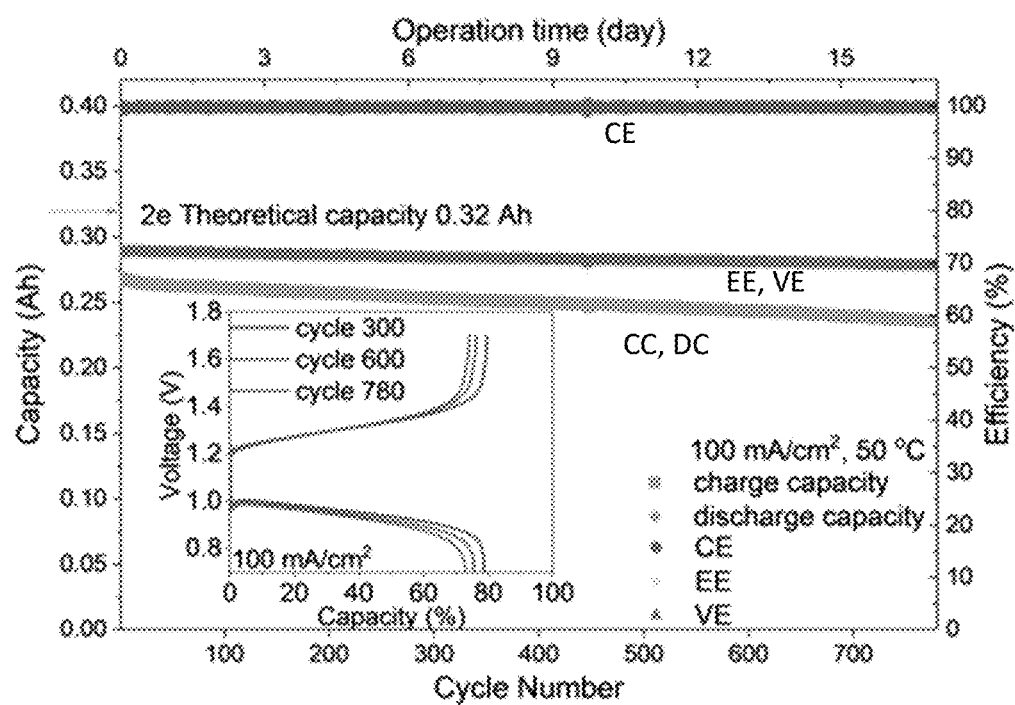
FIG. 23 shows results of an extended battery performance test over 17 days with an anolyte including 1 M 4C7SFL and a ferro/ferricyanide catholyte at 50° C. and 100 mA/cm$^2$ in air; the inset shows the polarization curves at selected cycles.
Figure 24:
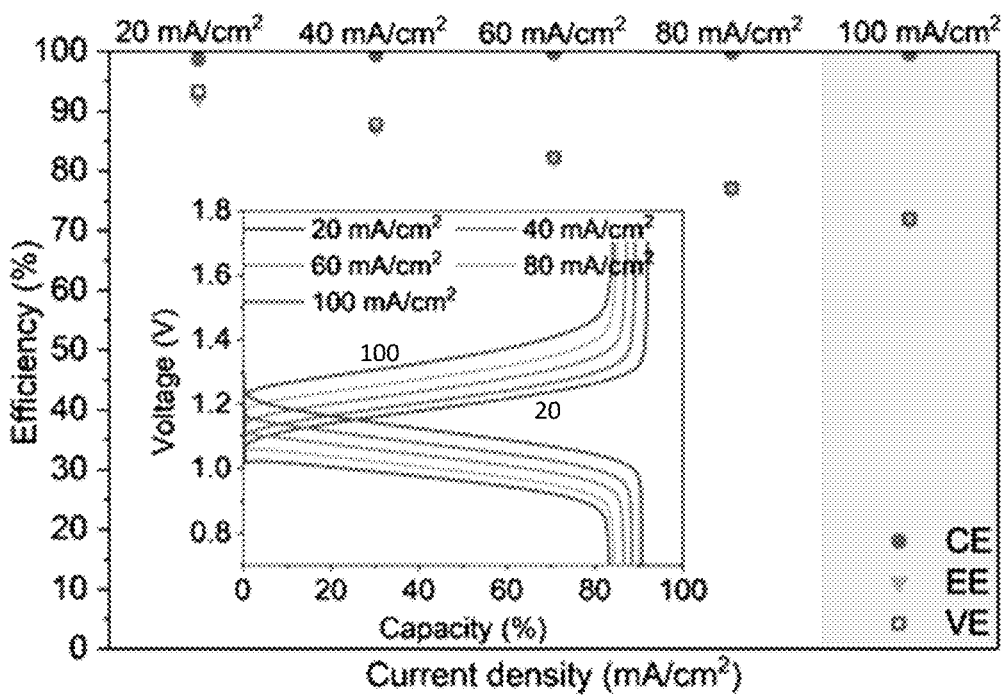
FIG. 24 shows efficiency and polarization curves of the battery of FIG. 23 at different current densities.
Figure 25:
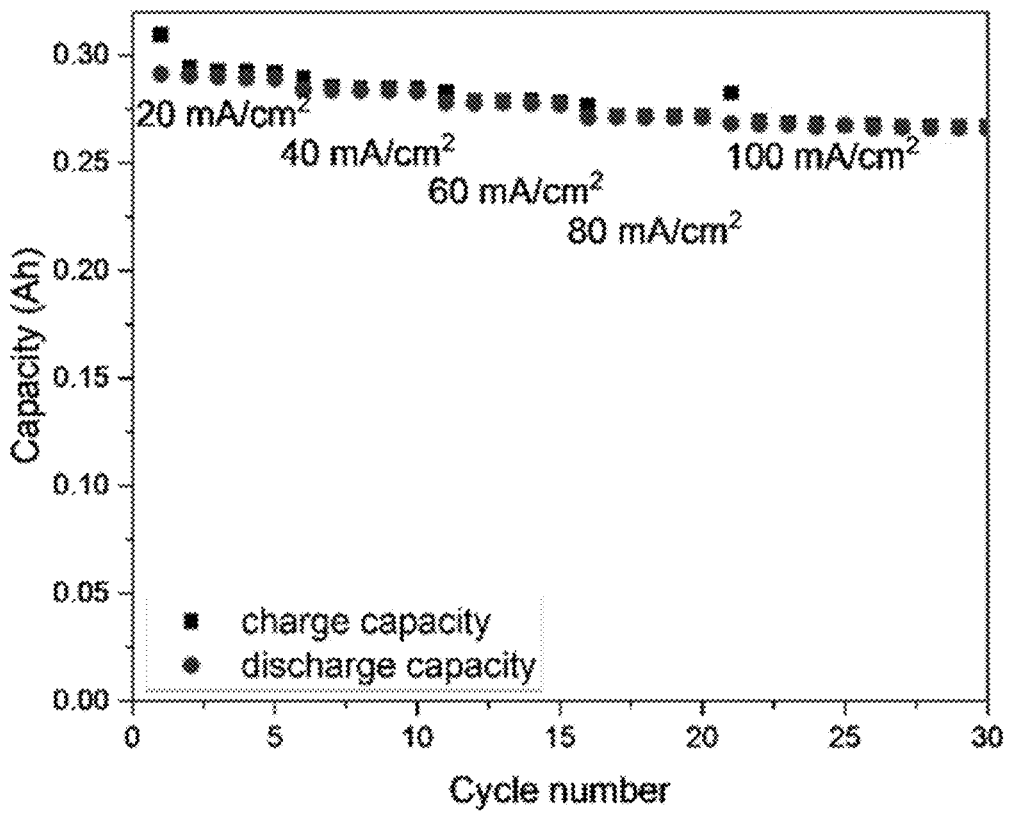
FIG. 25 is a graph of a current density performance test of the battery of FIG. 23 for an initial 30 cycles at 50° C.

In practical applications of RFBs, tolerance to fluctuations in operating temperature arising from ambient input and efficiency losses during operation is critical. For aqueous organic RFBs, although higher temperature may increase the solubility and lower the viscosity to improve the kinetics, it presents a severe threat to the stability of the organic active materials. For the same reason, flow battery tests of organic based electrolyte reported so far are conducted in inert atmosphere protected glove box, which is a hurdle to their practical applications. Another 1 M 4C7SFL/1 equiv NaOH (equivalent to 2 M electron transfer) anolyte was subjected to electrochemical cycling at 50° C. in air (FIGS. 23-24). A current density test was performed in the initial 25 cycles, detailed cycling data for the first 30 cycles is provided in FIG. 25. For the first time, stable cycling of an organic-based redox flow battery operated at an elevated temperature outside of an inert gas protected glove box was achieved throughout more than 700 cycles at 100 mA cm$^{-2}$ with an average CE at 99.8%, VE at 70.8%, and EE at 70.6%. Slight capacity decay was observed as cycling proceeded, with capacity retention of 88% over 780 cycles (99.98% per cycle over 16 days of cycling) at 100 mA cm$^{-2}$ and 50° C. The capacity decay was largely due to the accelerated crossover and enhanced water evaporation at higher temperature, which caused gradual precipitation (observed at both side of electrolytes).

Example 4

Preparation of Potassium
9-oxo-9H-fluorene-2,7-disulfonate (DSFL)

The synthesis was modified based on previously reported synthetic route (Chang et al., *Adv. Mater.* 2018, 30:1704234). 9H-fluoren-9-one (FL) (8 g, 33 mol) was dissolved in 25 mL of fuming sulfuric acid (18-23 wt %). The solution was stirred at 90° C. for 12 h. The reaction was monitored by NMR until all starting material was reacted. Then the solution was cooled to room temperature and poured onto 100 g of ice. Potassium hydroxide (10M solution) was used to adjusted pH to neutral. Precipitate was vacuum filtrated and dried on vacuum overnight. Solid mixture was dissolved in dimethyl sulfoxide (DMSO) and inorganic salt was filtered. Filtrate was diluted with acetone. Precipitate was vacuum filtrated and dried on vacuum overnight. Product was further dried on vacuum overnight at 50° C.

Example 4

Concentration and Substitution Effects on Battery Performance

Figure 26:
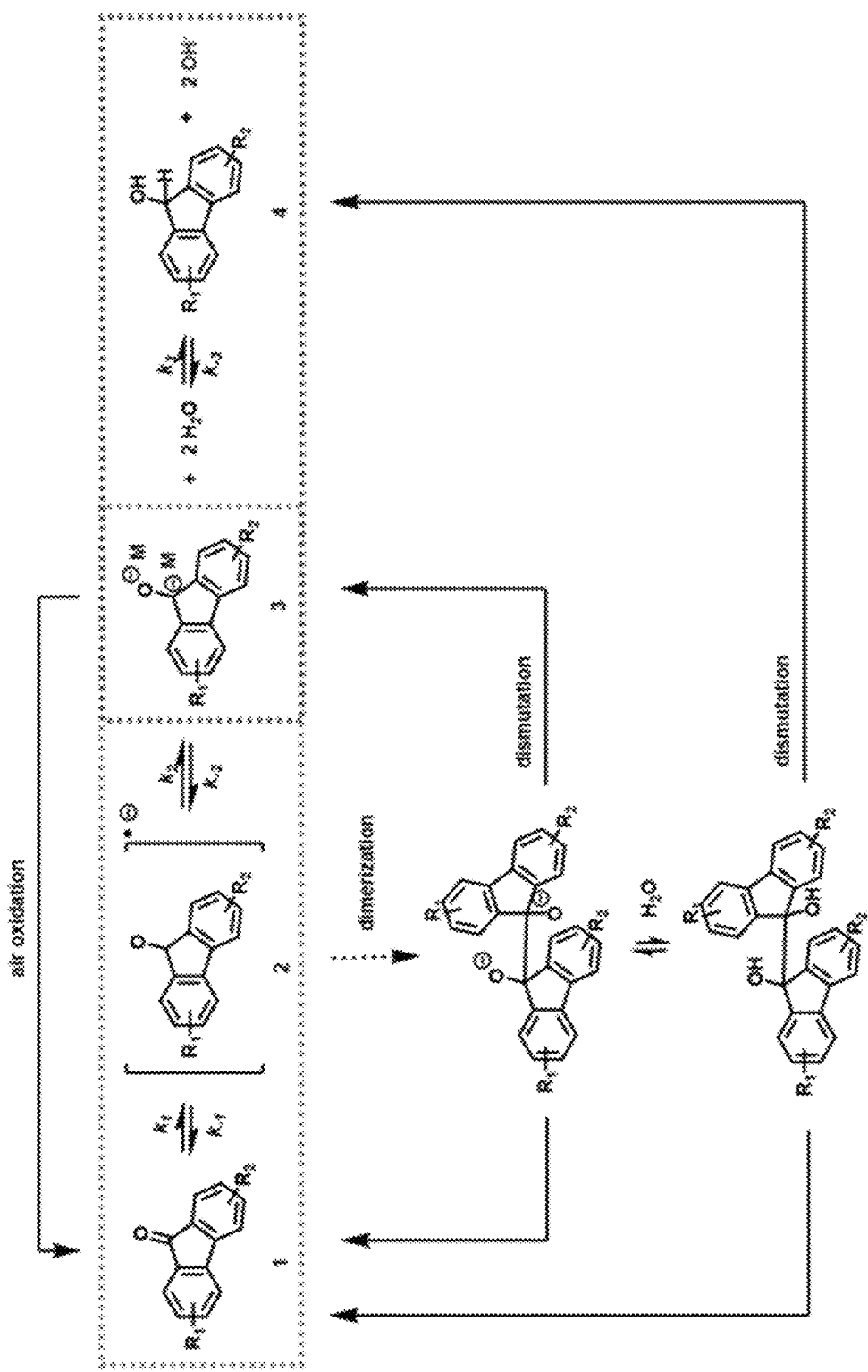
FIG. 26 is a reaction scheme showing a coupled mechanism for redox reversibility of a fluorenone derivative.
Figures 27A, 27B, 27C, 27D, 27E, 27F:
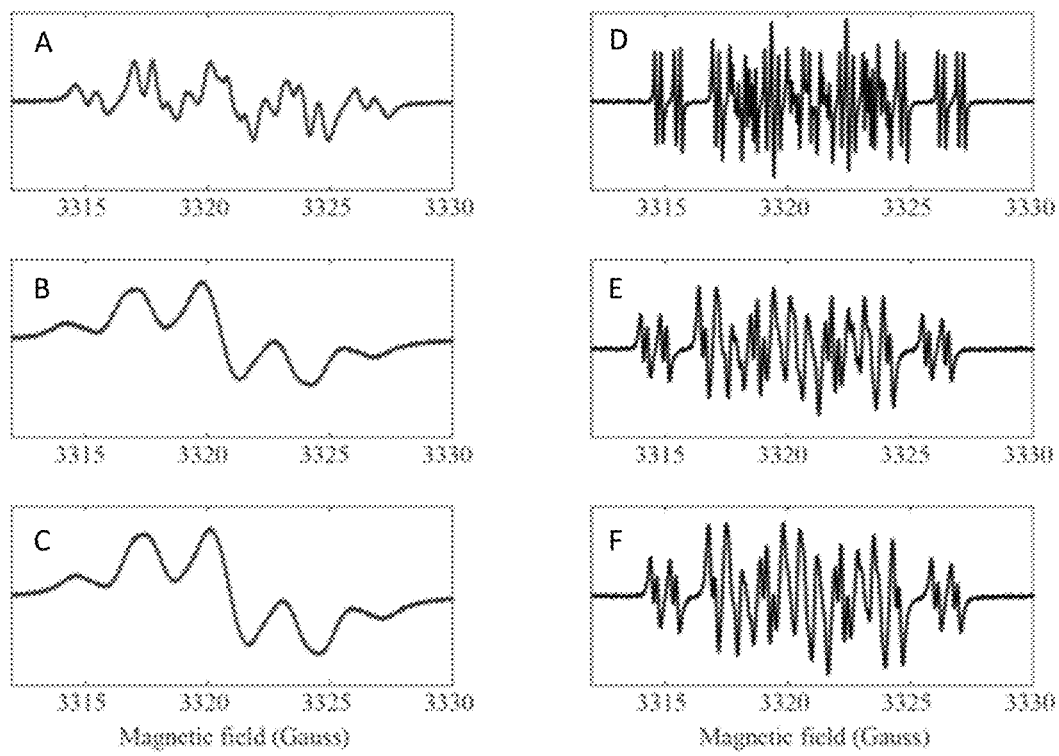
FIGS. 27A-27F show EPR spectra of 4C7SFL at 0.1 M (A, D), 0.5 M (B, E), and 1 M (C, F) charged at 50% SOC (A-C) and voltage limit reached (D-F).
Figure 28:
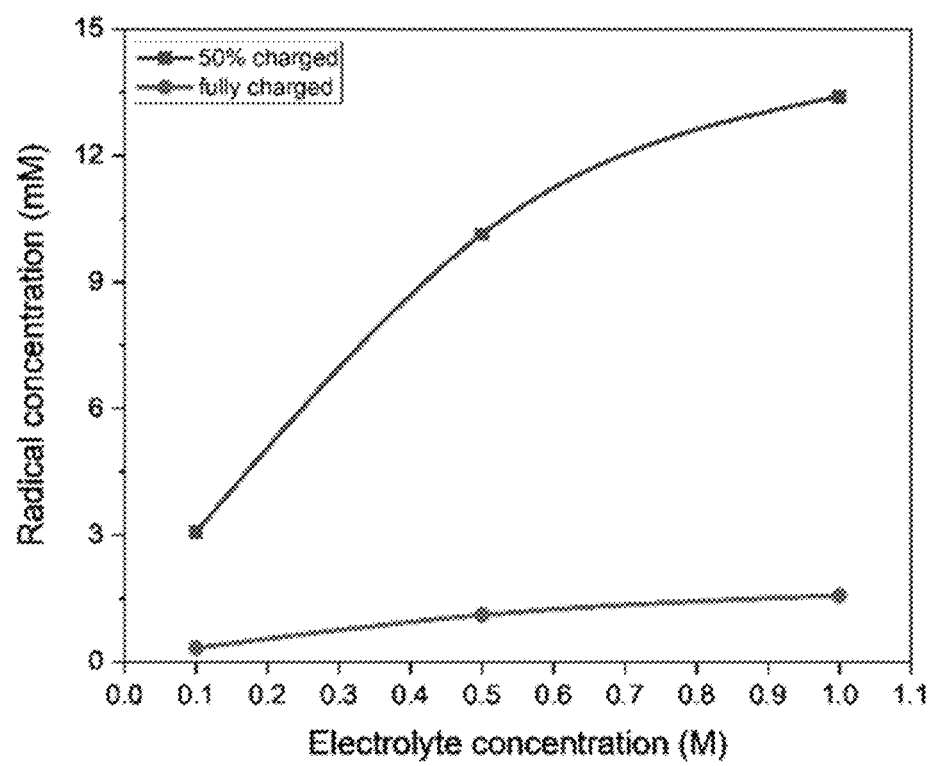
FIG. 28 shows radical concentration calculated from EPR signal of electrolyte solution charged at 50% (squares) and voltage limit reached (circles) vs electrolyte solution concentration.
Figure 29:
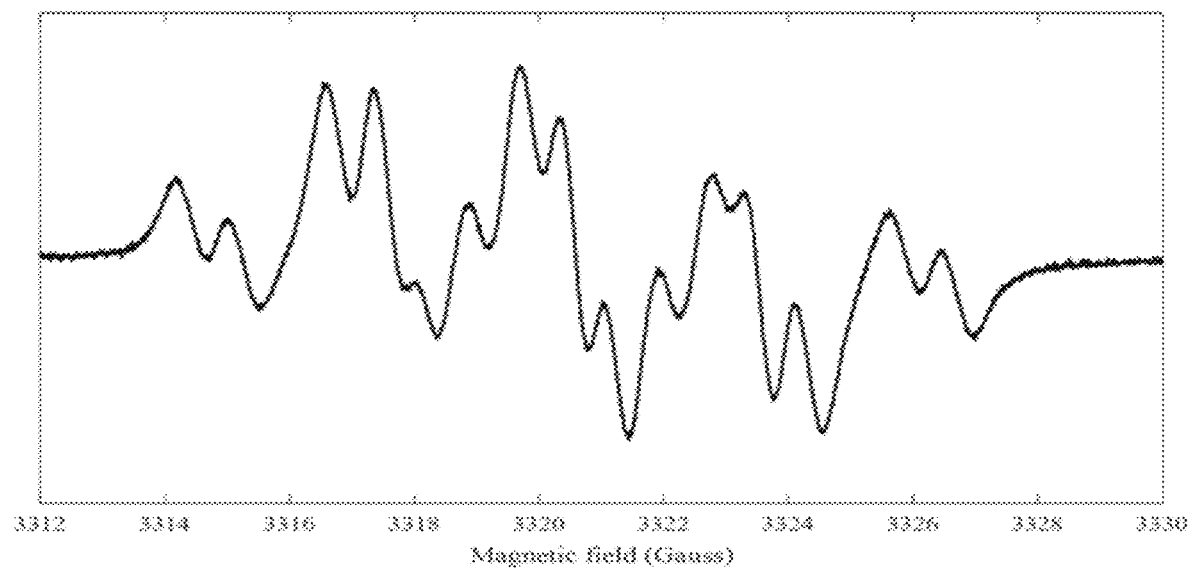
FIG. 29 shows an EPR spectrum of a freshly prepared solution of 50 mM 4C7SFL+50 mM 4C7SFL-OH with 1 M NaOH, corresponding to a radical concentration of 6.5 mM.

Without wishing to be bound by a particular theory of operation, a proposed mechanism based on the obtained data in the foregoing examples and literature is shown in FIG. 26. The formation of fluorenol core structure was confirmed by 2D NMR analysis of the fully reduced anolyte material. HSQC clearly indicated the benzylic proton at 5.3 ppm (shifted within 0.2 ppm in different solvent) and correlation with carbon at 72.9 ppm in DMSO-d6. Both HMBC and COSY showed the fluorenol structural relationship. To gain insight during battery operation, NMR aliquots were taken during the charging process to examine possible intermediates formed during the charging process, which potentially can be numerous and complex. Surprisingly no evidence was found for the presence of pinacol-type dimers at battery conditions with NMR detection, indicating either their existence as short-lived intermediates at battery operating condition, or a direct, bimolecular pathway of compound 2 (FIG. 26) which leads to a dismutation charging mechanism instead of a stepwise charging mechanism. EPR results provided evidence for existence of radical intermediate 2 formation during the process. No over-reduced de-hydroxyl fluorene type products were detected. FIGS. 27A-27F show EPR spectra of 4C7SFL at 0.1 M (A, D), 0.5 M (B, E), and 1 M (C, F) charged at 50% SOC (A-C) and voltage limit reached (D-F). The spectral line width is greater at a higher radical concentration due to a larger solution viscosity and more spin-spin interactions. FIG. 28 shows radical concentration calculated from EPR signal of electrolyte solution charged at 50% (squares) and voltage limit reached (circles) vs electrolyte solution concentration. The EPR concentration test revealed that at 50% SOC, the concentration was not at half of the electrolyte concentration, suggesting a radical chemical reaction during the charging process. This result did not support a step-wise charging mechanism as observed by CV, with two distinct reduction peaks. FIG. 29 shows an EPR spectrum of a freshly prepared solution of 50 mM 4C7SFL+50 mM 4C7SFL-OH with 1 M NaOH, corresponding to a radical concentration of 6.5 mM and indicating that comproportionation of fully charged and fully discharged material can occur under basic conditions to yield ketyl radical. An exemplary scheme of the comproportionation reaction is shown in FIG. 30. Note that a solution with the same composition but stored at room temperature for a month, does not provide any EPR signal, and the solution of 50 mM 4C7SFL+50 mM 4C7SFL-OH without NaOH also has no detectable EPR signal.

Figure 31:
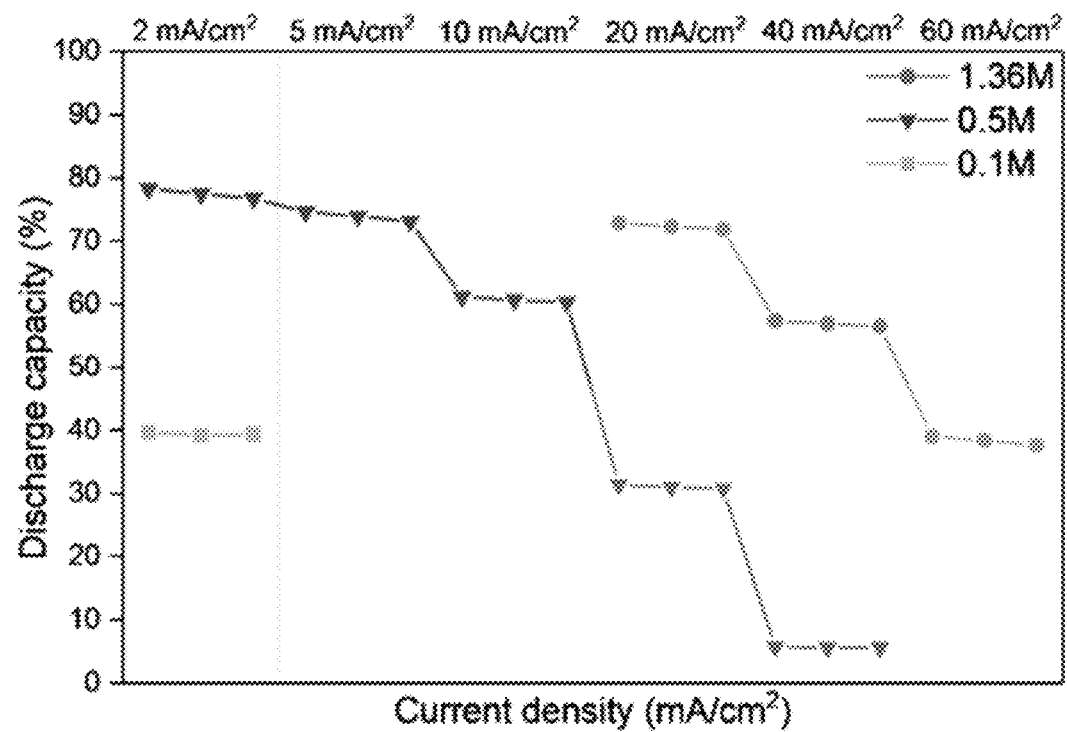
FIG. 31 is a graph showing the effects of anolyte concentration on battery utilization at various current densities; the anolyte comprised 4C7SFL.

Unlike other reported redox systems, the ketone/alcohol system battery capacity utilization was highly concentration dependent (FIG. 31), which supported the coupled chemical reaction mechanism. The deprotonation equilibrium was largely correlated with the ratio among active material, hydroxide and water, thus leading to significant performance differentiation based on concentration. At 0.1 M active material, the battery can only discharge at very low current density to less than 50% utilization. Upon increasing the active material concentration, the ratio of active material to water changed dramatically, enabling the equilibrium favoring anionic species 3 within the discharge time. Because battery discharge is dependent on the availability of deprotonated FL-OH, a decrease of total FL-OH concentration to 0.1 M can result in a resting state concentration of deprotonated FL-OH that cannot sustain a reasonable current density beyond 2 mA cm$^{-2}$. With increased material concentration (and decreased water concentration), a higher concentration of anionic species relative to protonated species can be achieved, improving utilization to 31% at 0.5 M and 70% at 1.36 M when cycled at 20 mA cm$^{-2}$. At 40 mA cm$^{-2}$, capacity utilization increases from less than 10% at 0.5 M, to nearly 60% at 1.36 M.

Figure 32:
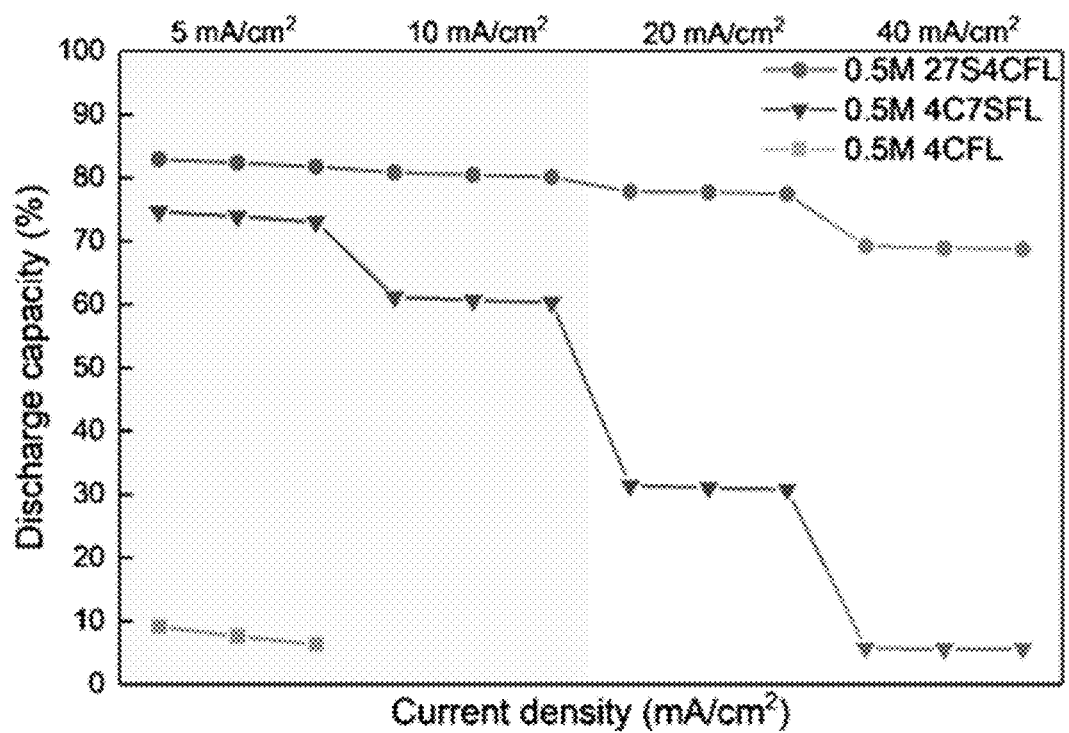
FIG. 32 shows the effects of various substitution patterns on battery utilization at various current densities.

In order to further prove the equilibrium theory and probe the effect of FL-OH pKa on battery performance, a battery performance comparison was demonstrated using same concentration (0.5 M) of 2CFL, 4C7SFL, and 27S4CFL. The results are shown in FIG. 32. With increase in Hammett constant, a smaller pKa was achieved. As a result, a better utilization was achieved. With stronger electron withdrawing groups (EWGs) on the aromatic ring, a higher ratio of anionic species can be achieved within the discharge time, leading to higher utilization. When 4C7SFL and 27S4CFL were cycled at 20 mA cm$^{-2}$, increased discharge capacities of 30% and 80%, respectively, were obtained, highlighting the incredible effect of adding one extra sulfonate group. At 40 mA cm$^{-2}$, 4C7SFL discharge capacity dropped to less than 10%, while 27S4CFL maintained a discharge capacity of nearly 70%. The obvious rate performance differences support that functionalization with stronger EWG groups providing a sufficient amount of deprotonated species for discharge at increased current density. Based on the proposed coupled chemical reaction mechanism, the anolyte side theoretically would generate hydroxide along with charging process. Theoretically during discharge, compound 3 (FIG. 26) would be consumed along with in situ generated hydroxide, and the equilibrium should be able to move back given a suitable discharge rate (matching equilibrium constant) based on Le Chatelier's Principle.

Figure 33:
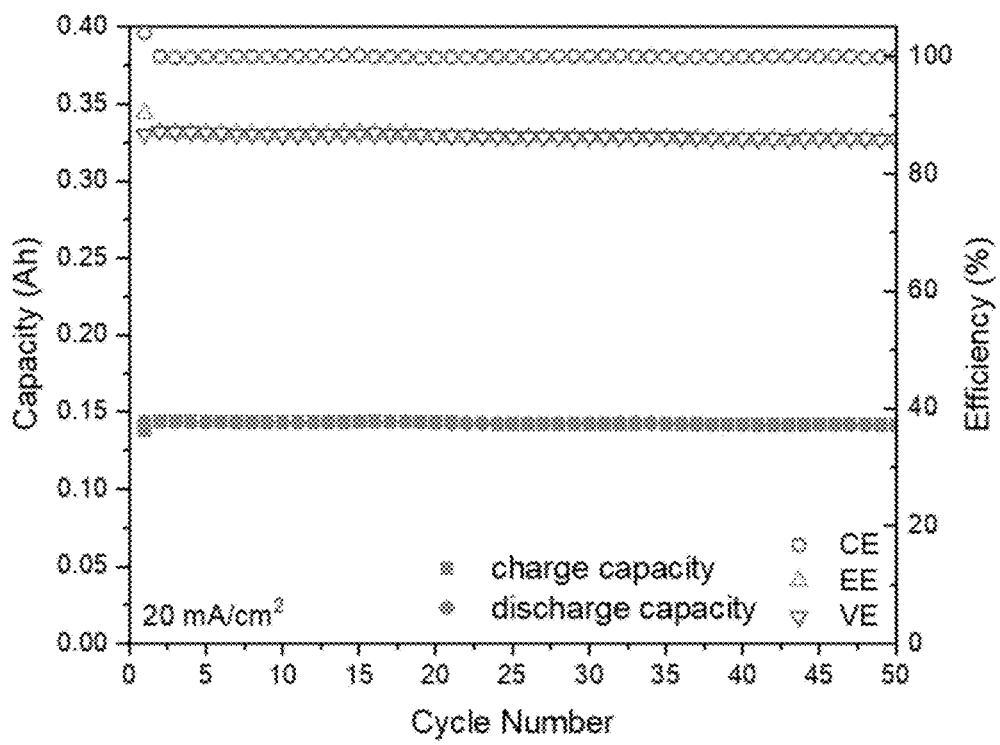
FIG. 33 shows the cycling performance of a battery including an anolyte comprising 0.5 M 9-oxo-2,7-sulfo-9H-fluorene-4-carboxylic acid (27S4CFL) and 0.1 M NaOH; the battery was operated at a current density of 20 mA/cm$^2$.

To test this concept, a battery containing 0.1 M NaOH was assembled. The catholyte was excess ferro/ferricyanide. 27S4CFL (the strongest EWGs among the three compounds of FIG. 32) and 0.1 M NaOH were used to avoid potential dimer formation (radical anion intermediate 2 stability was sensitive to pH level, as discussed before), which potentially would introduce a more complicated mechanism. The result in FIG. 31 clearly indicated a stable operation even without a large amount of added base, supporting the equilibrium and in situ generation of hydroxide. A second plateau was observed during charging near 50% capacity (FIG. 33). A similar phenomenon was observed using 4C7SFL. At higher current density, a second plateau was observed near halfway (FIG. 16). With a higher electron transfer rate, direct electron transfer by electrochemical reduction of 2 outcompeted the dismutation chemical reaction of 2 within the same time scale.

Figure 34:
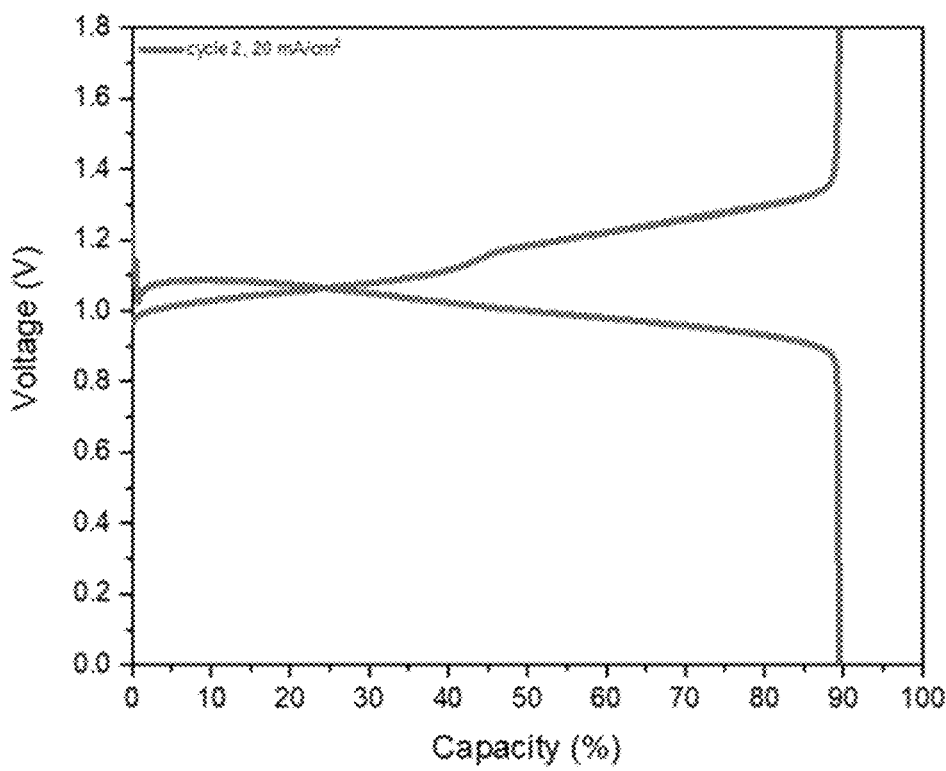
FIG. 34 shows the polarization curve of the battery of FIG. 33.
Figure 35:
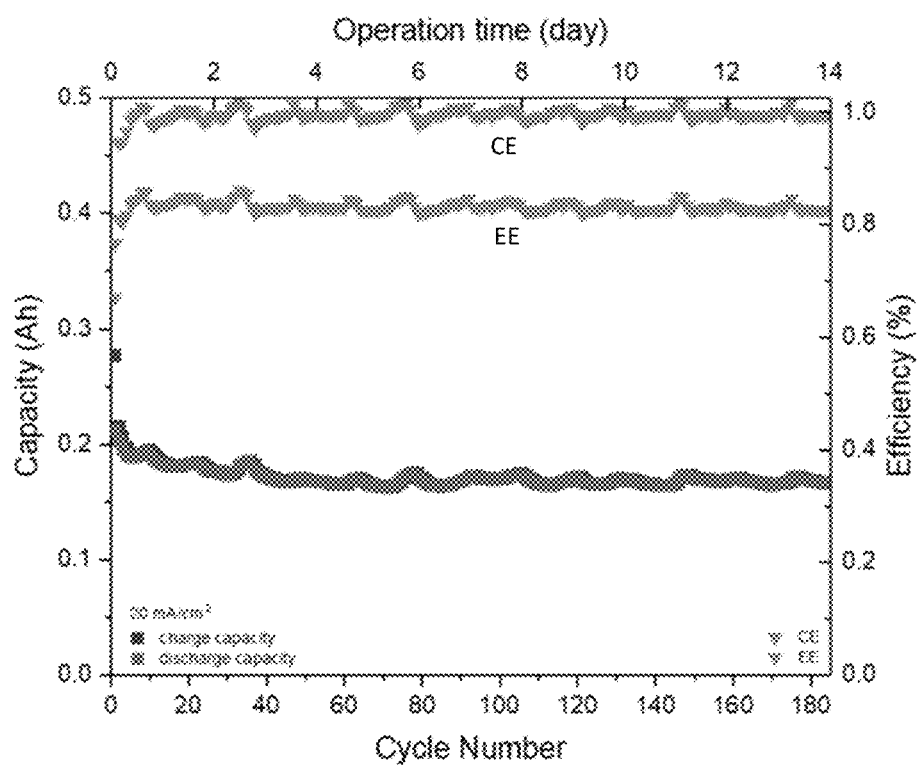
FIG. 35 shows performance of a battery operated without a nitrogen atmosphere at room temperature and a current density of 20 mA/cm$^2$; the battery included an anolyte comprising 1 M 4C7SFL.
Figure 36:
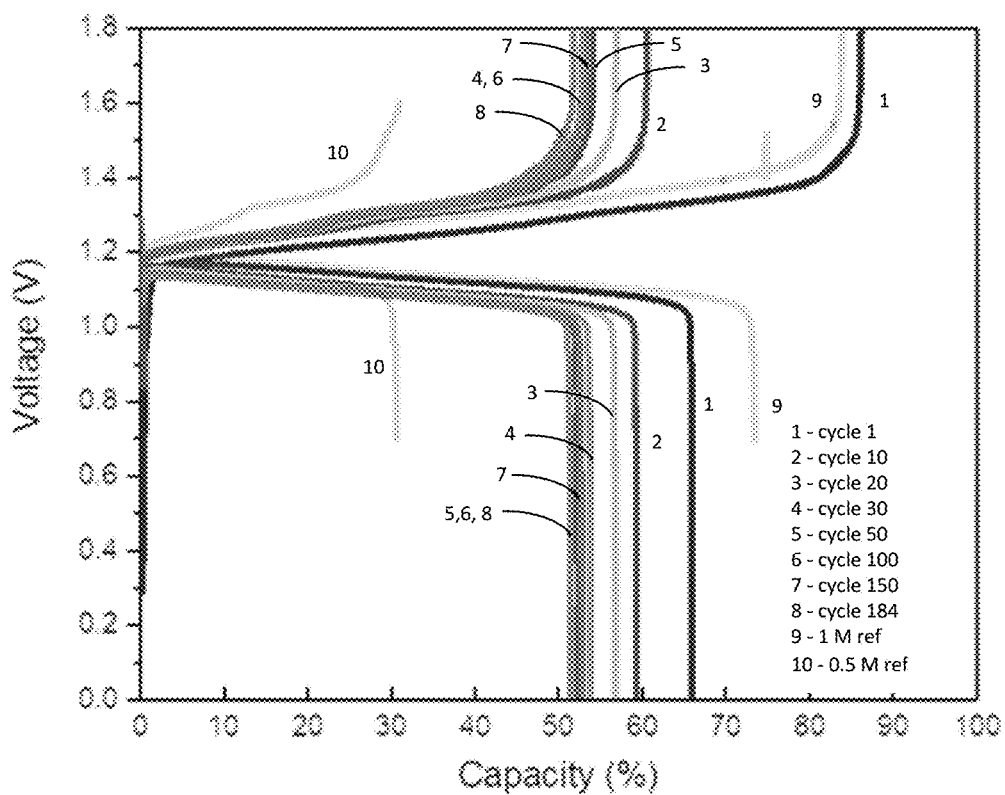
FIG. 36 shows polarization curves of the battery of FIG. 35.
Figure 37:
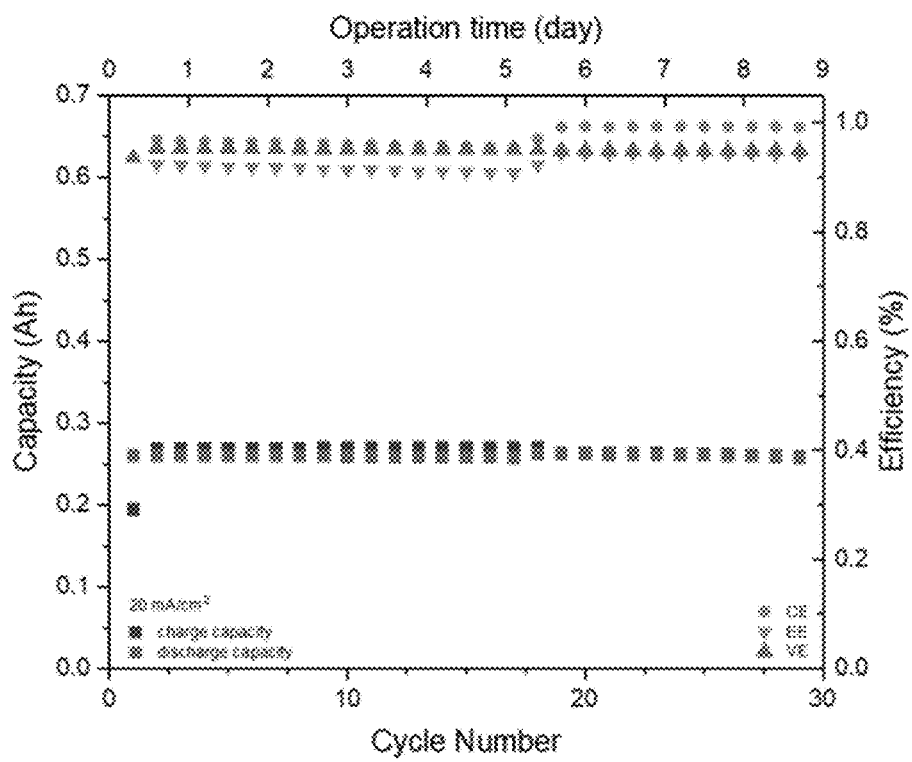
FIG. 37 shows performance of the battery of FIG. 35 operated at 50° C.
Figure 38:
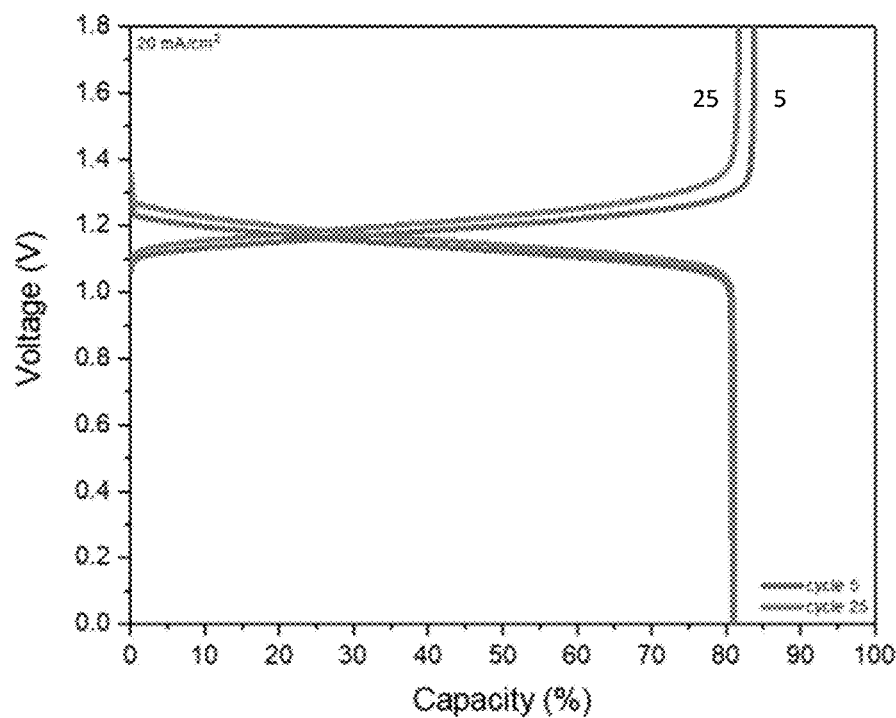
FIG. 38 shows polarization curves of the battery of FIG. 37 at 50° C.
Figure 39:
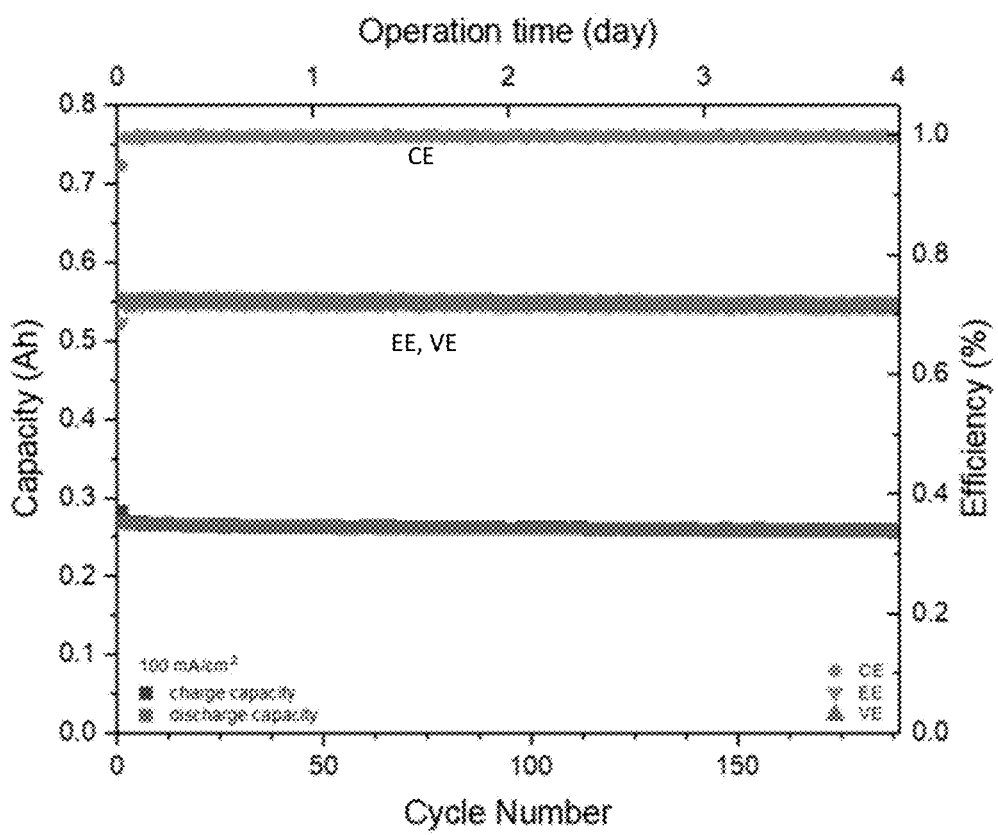
FIG. 39 shows performance of a battery including an anolyte comprising 1 M 4C7SFL and a catholyte comprising 0.9 M ferro/ferricyanide, operated at 50° C. and 20 mA/cm$^2$.
Figure 40:
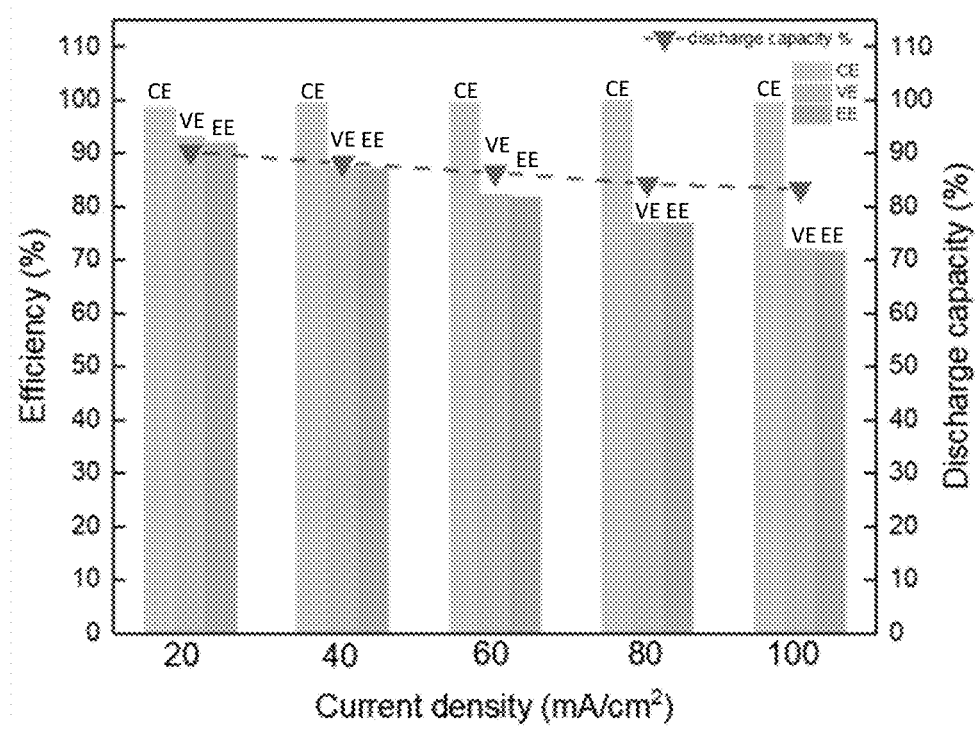
FIG. 40 shows performance of the battery of FIG. 39 at varying current densities.

For the reason that charged anolyte is usually sensitive to 02, flow battery tests of organic based electrolyte reported so far are conducted in inert atmosphere, which is a significant hurdle to their practical applications. We submit another battery test without significant deaerating treatment at reasonable CE and EE (FIGS. 34 and 35). The 1 M battery was assembled without N$_2$ atmosphere, sealed with a stopper and parafilm, and no further deoxygenation was conducted before charging. The battery operated stably at 20 mA/cm$^2$ for 2 weeks. The observed capacity fluctuation was attributed to temperature changes on a daily basis. The battery demonstrated an average coulombic efficiency (CE) close to 100% and energy efficiency (EE) >80%. The first cycle low CE was attributed to charged material consuming existing 02 in the cell system. As expected, the first cycle charging capacity was a little higher than same amount of substance in a battery inside the purge box (without 02 induced discharge influence). However, no irreversible side reactions occurred and long-term cycling occurred analogous to tests conducted in an inert atmosphere purge box. Due to the large active material concentration difference on each side of the battery, water transfer happened along with cycling, resulting in decreased anolyte active material concentration, which led to a utilization decrease to above 50%. After 50 cycles (4 days), a balanced ion strength was established and no further concentration change occurred. The battery was then able to operate at the same capacity for 10 days. Theoretically such an equilibrium should be accelerated by temperature increase, thus leading to higher utilization. To confirm this, the same battery was moved to a 50° C. oven with forced air circulation for testing (FIGS. 37 and 38). Upon the temperature increase, the capacity was instantly increased to >80% of its theoretical, fully supporting that the previous capacity drop was caused by concentration decrease with active material intact. Furthermore, a post NMR analysis on the anolyte material showed a mixture of the ketone and alcohol, with no sign of core structure degradation. In order to examine battery performance with minimal concentration changes (almost inevitable with the imbalanced concentration of anolyte relative to catholyte), a near balanced catholyte (0.9 M) was paired with 1 M anolyte material (limited by catholyte material solubility). Results shown in FIGS. 39 and 40 indicated that, at higher temperature and higher concentration, a faster equilibrium can be achieved within the discharge time window, leading to much higher utilization. At elevated temperature, the battery can still access >80% of its theoretical capacity at 100 mA/cm$^2$.

Example 5

Synthesis and Characterization of 14N2CN3OHFL

14N2CN3OHFL (3-hydroxy-9-oxo-9H-indeno[1,2-b] pyrazine-2-carbonitrile) was synthesized following the procedure shown below and described in EP 1 749 822 A1:

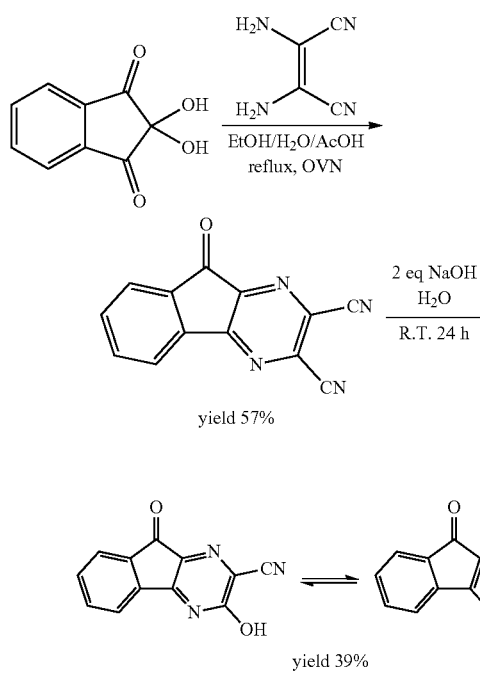

yield 57% yield 39%

Figure 41A:
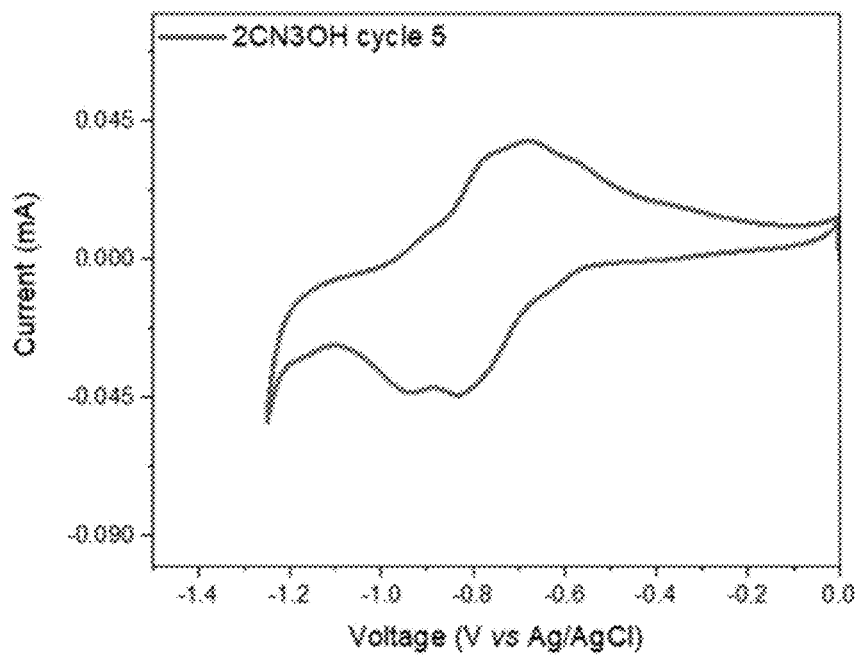
FIGS. 41A and 41B show a cyclic voltammogram (41A) of 0.1 M 3-hydroxy-9-oxo-9H-indeno[1,2-b]pyrazine-2-carbonitrile (14N2CN3OHFL) and first cycle charge/discharge capacity (36B) of a battery including the anolyte at a constant current of 5 mA.
Figure 41B:
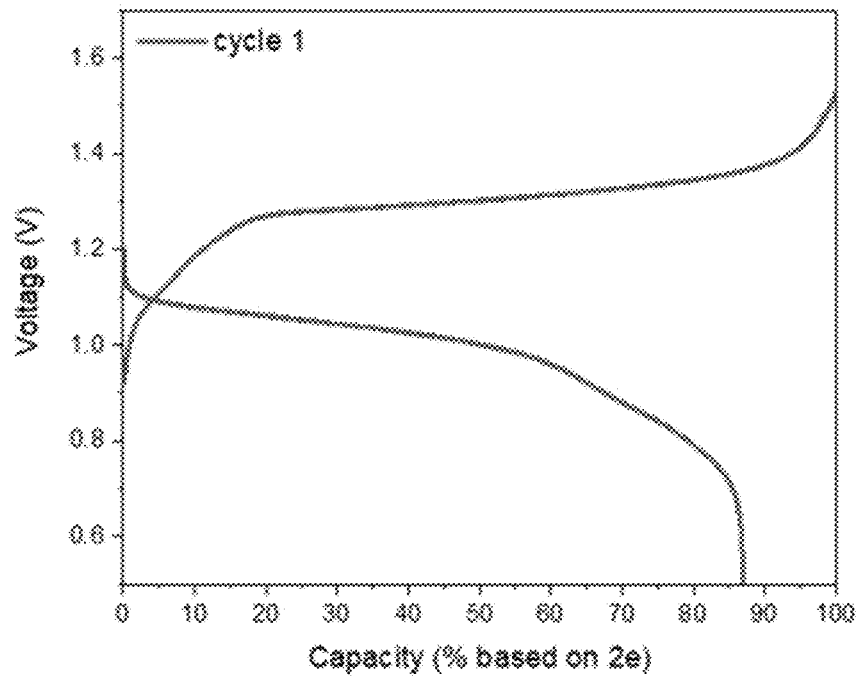

14N2CN3OHFL exhibited a material solubility of 1 M in aqueous 2 M NaOH solution, while maintaining CN as a strong electron withdrawing group. Cyclic voltammetry showed reversible peak at near −0.85 V vs Ag/AgCl in 1 M NaOH solution (FIG. 41A). By pairing with excess potassium ferri/ferrocyanide in H-cell (FIG. 41B), the battery containing of 0.1 M material exhibited a discharge capacity of 87% of its theoretical capacity (based on two-electron transfer calculation), illustrating a potential battery anolyte material utilizing ketone hydrogenation and dehydrogenation based on the N-heterocyclic fluorenone compounds. The H-cell was assembled with 0.6 mmol (0.1 M) of anolyte material with 2 M NaOH in 6 mL solution in anode side. The cathode side contained 1.8 mmol (0.3 M) potassium ferricyanide, 1.8 mmol (0.3 M) potassium ferrocyanide, and 0.1 M NaOH in 6 mL solution. Nafion 211 (D=16 mm, pre-soaked in 2 M NaOH at R.T. OVN) was used as separator. Graphite felt (1×2 cm) under solution surface level, 3 mm thickness) was used as electrode material. The test was conducted on an Arbin Tester, with a constant current of 5 mA.

Figure 42:
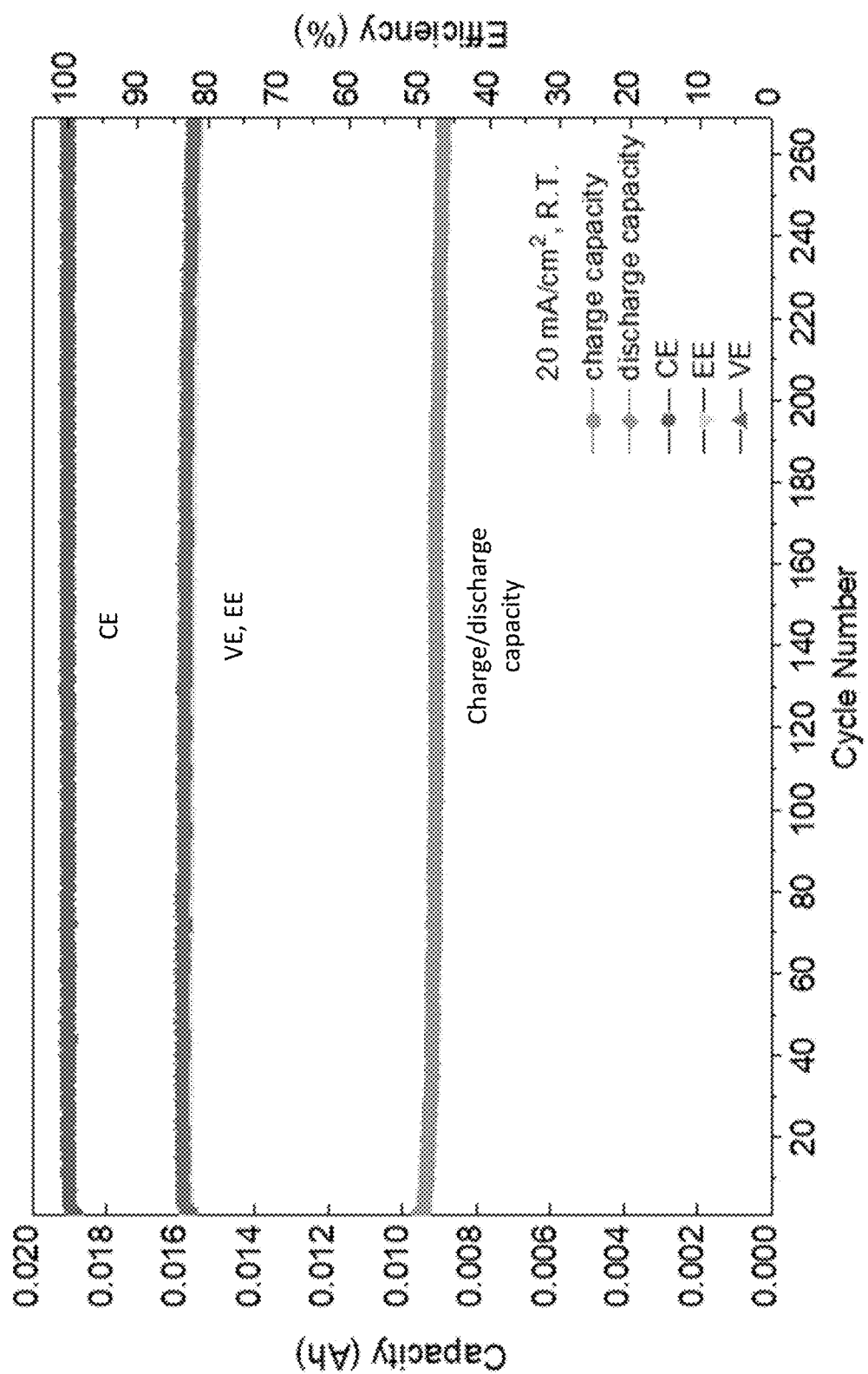
FIG. 42 shows performance of the battery of FIG. 41B operated over 260 cycles at 20 mA/cm$^2$.

By pairing with excess potassium ferri/ferrocyanide in Interdigitated cell, the battery (FIG. 42) containing 0.1 M 14N2CN3OHFL achieved stable charge/discharge at 20 mAcm$^{-2}$, with a Columbic efficiency of near 100%, voltage efficiency of above 80%, and energy efficiency of above 80%. Albeit at low utilization (near 30%) with such low concentration, the demonstrated battery was able to deliver stable discharge at 20 mAcm$^{-2}$ over 250 cycles. The battery was assembled with 0.6 mmol (0.1 M) of anolyte material with 1 equiv. of NaOH in 6 mL 1 M NaOH solution on the anode side. The cathode side contained 2 mmol (0.2 M) potassium ferrocyanide, 0.5 mmol (0.05 M) potassium ferricyanide, and 1 M NaOH in 10 mL solution. Nafion 212 (pre-soaked in 1 M NaOH at R.T. OVN) was used as separator. ELA/Freudenberg H23 (400° C., 4 h) was used as the electrode. The flow rate was 40 mL/min.

Example 6

Characterization of 45NFL

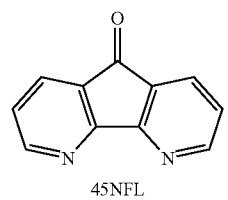 [SMILES: O=C1c2cccnc2-c2ncccc21]

45NFL

Figure 43A:
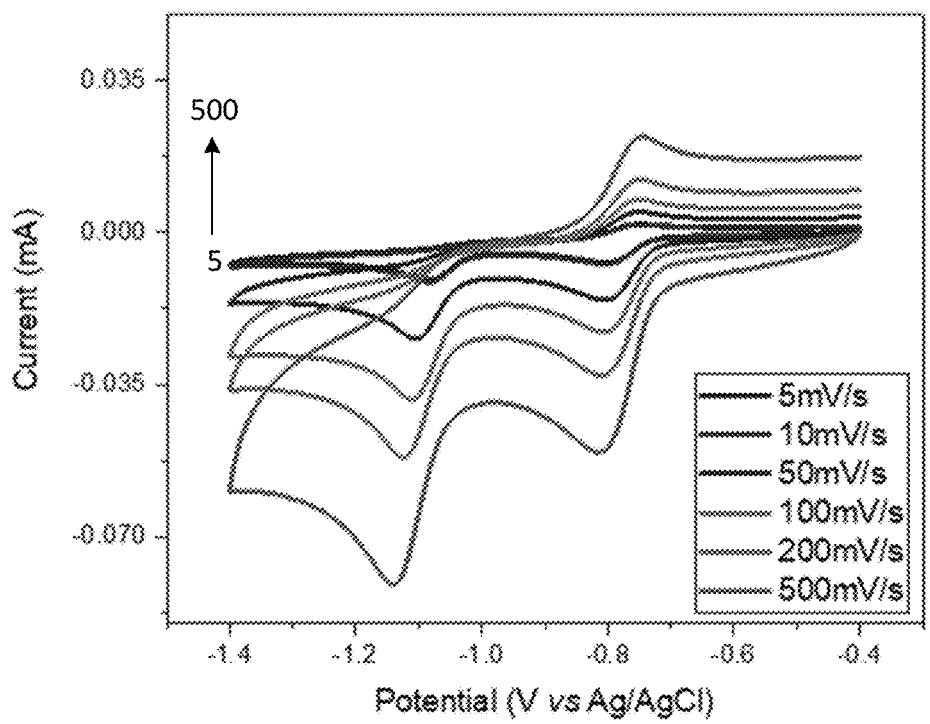
FIGS. 43A-43B show cyclic voltammograms of 4.5-diazafluoren-9-one (45NFL).
Figure 43B:
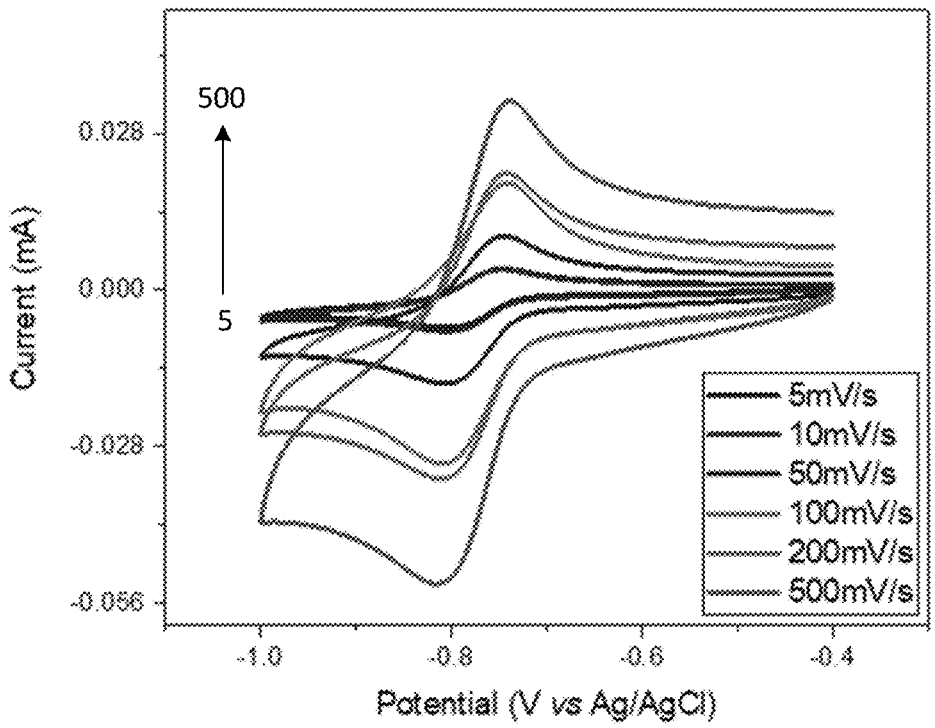

45NFL (4,5-diazafluoren-9-one) exhibits limited solubility due to a lack of functional groups. However, cyclic voltammetry was performed with 0.5 mg 45NFL in 1 M NaOH, with glassy carbon as a working electrode and Ag/AgCl as the reference electrode. The results are shown in FIGS. 43A-43B.

Figure 44:
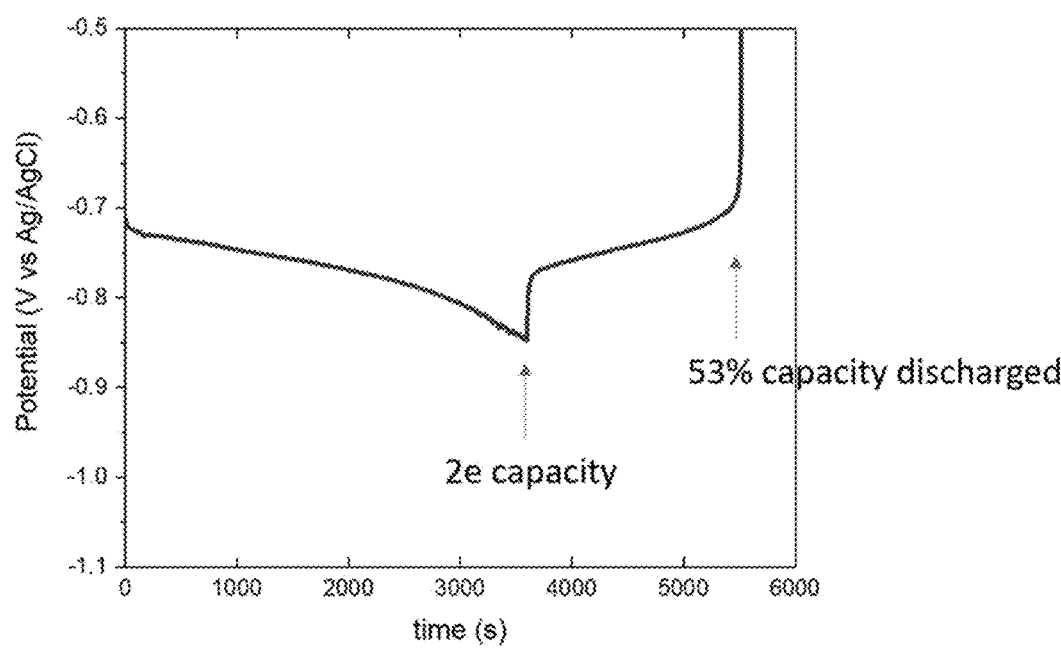
FIG. 44 is a graph of potential versus time for a cell with an anolyte of 5 mL of 10 mM 45 NFL in 1 M NaOH and a catholyte of 6 mL of 0.2 M ferricyanide, 0.05 M ferrocyanide, 1 M NaOH; 1C rate.

A cell including a Nafion™ 211 separator (presoaked in 1 M NaOH at room temperature overnight), a graphite felt electrode (3 mm thick, ~1*1.5 cm in solution) and Ag/AgCl reference electrode was prepared. The anolyte was 5 mL of 10 mM 45 NFL in 1 M NaOH. The catholyte was 6 mL of 0.2 M ferricyanide, 0.05 M ferrocyanide, 1 M NaOH. The cell was cycled at 1C rate. The results are shown in FIG. 44.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An aqueous composition comprising:
   an aqueous anolyte comprising
   (i) a compound or a salt thereof having a structure according to any one of formulas I-III

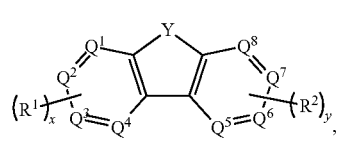

(I)

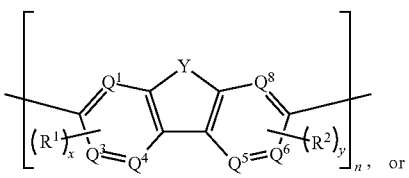

(II)

, or

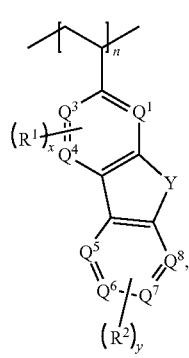

(III)

where Q¹-Q⁴ independently are CH, C(R¹) or N, wherein 0, 1, or 2 of Q¹-Q⁴ are N,
Q⁵-Q⁸ independently are CH, C(R²), or N, wherein 0, 1, or 2 of Q⁵-Q⁸ are N,
Y is C=O or C(H)OH,
each R¹ and R² independently is an electron withdrawing group,
n is an integer >1, and
x and y independently are 0, 1, 2, 3, or 4, where if none of Q¹-Q⁸ is N, then x and y are not 0, and
(a) R¹ and R² are different electron withdrawing groups, or
(b) the compound comprises two different R¹ or two different R² groups, or
(c) both (a) and (b);

(ii) a base; and
(iii) water.

2. The aqueous composition of claim 1, wherein the compound is not 7-nitro-9-oxo-9H-fluorene-2-carboxylic acid, 7-nitro-9-oxo-9H-fluorene-4-carboxylic acid, 5-nitro-9-oxo-9H-fluorene-4-carboxylic acid, 7-amino-9-oxo-9H-fluorene-2-carboxylic acid, 7-amino-9-oxo-9H-fluorene-1-carboxylic acid, or 7-foramido-9-oxo-9H-fluorene-2-carboxylic acid.

3. The aqueous composition of claim 1, wherein each R¹ and R² independently is —SO₃Z, —CO₂Z, —(CH₂)ₘPO₃Z₂, X, —NR'₃⁺, —NO₂, —SO₂R', —CN, —CX₃, —COX, —C(H)O, —C(O)R', —C(O)NH₂, —C(O)NHR', —C(O)NR'₂, N=O, —OR', or —(CH₂CH₂O)ₚR', where
each R' independently is H, substituted or unsubstituted aliphatic, or substituted or unsubstituted heteroaliphatic,
X is halo,
each Z independently is a counterion with a +1 charge;
m is an integer from 0 to 10; and
p is an integer from 1 to 10.

4. The aqueous composition of claim 1, wherein each R¹ and R² independently is —SO₃Z, —CO₂Z, —CF₃, —NO₂, —CN, or —OH.

5. The aqueous composition of claim 1, wherein the compound has a structure according to any one of formulas IA-IC, IIA-IIB, or IIIA-IIIC:

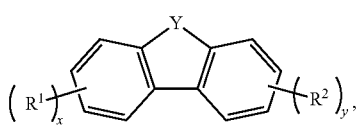
(IA)

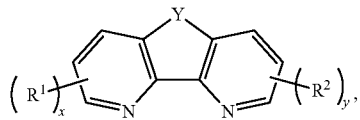
(IB)

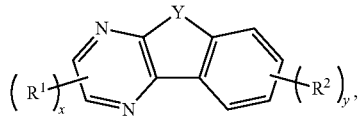
(IC)

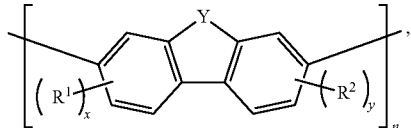
(IIA)

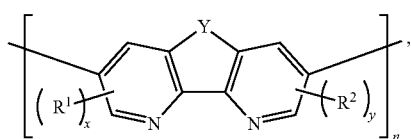
(IIB)

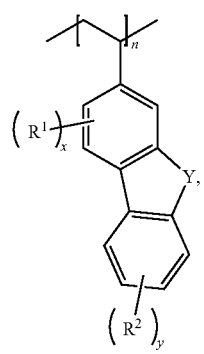
(IIIA)

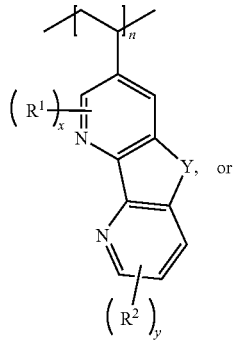
(IIIB)

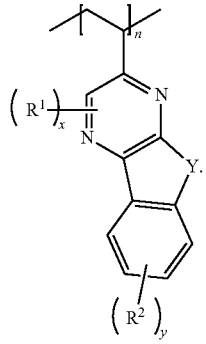
(IIIC)

6. The aqueous composition of claim 5, where the compound has a structure according to any one of formulas IB, IC, IIB, IIIB, or IIIC, and $R^1$ and $R^2$ independently are —CN, —OH, —SO$_3$Z, —COOZ, —(CH$_2$)$_m$PO$_3$Z$_2$, —CF$_3$, —F, —Br, —NO$_2$, or —(CH$_2$CH$_2$O)$_p$R'.

7. The aqueous composition of claim 5 where the compound has a structure according to any one of formulas IA, IIA, or IIIA, and $R^1$ and $R^2$ independently are —SO$_3$Z or —CO$_2$Z.

8. The aqueous composition of claim 7, wherein:
(i) x is 1 or 2, and each $R^1$ independently is —SO$_3$Z or —CO$_2$Z; or
(ii) y is 1, and $R^2$ is —SO$_3$Z; or
(iii) both (i) and (ii).

9. The aqueous composition of claim 5, wherein the compound has a structure according to formula IC or IIIC, where x is 2 and one $R^1$ is —OH.

10. The aqueous composition of claim 1, wherein $R^1$ and $R^2$ are asymmetrically positioned on the compound.

11. The aqueous composition of claim 1, wherein the compound comprises

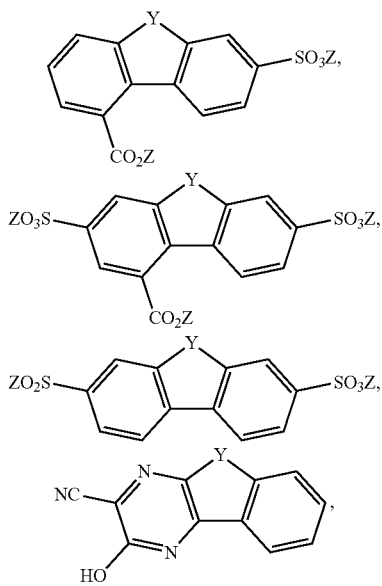

or any combination thereof.

12. The aqueous composition of claim 1, wherein:
(i) the base comprises an alkali metal hydroxide; or
(ii) the compound has a concentration within a range of from 0.5 M to 1.5 M; or
(iii) both (i) and (ii).

13. The aqueous composition of claim 1, consisting essentially of:
the base;
the compound; and
water.

14. An aqueous electrolyte system for a redox flow battery system, comprising:
an aqueous anolyte according to claim 1; and
an aqueous catholyte comprising water and an electrochemically active material.

15. The aqueous electrolyte system of claim 14, wherein the aqueous catholyte comprises:

K$_4$Fe(CN)$_6$, K$_3$Fe(CN)$_6$, or a combination thereof; and water.

16. The aqueous electrolyte system of claim 14, wherein:
the aqueous anolyte comprises an alkali metal hydroxide and

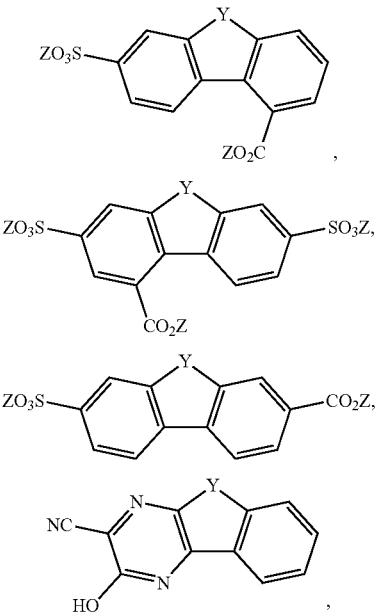

or any combination thereof, where each Z independently is a counterion with a +1 charge; and
the aqueous catholyte comprises an alkali metal hydroxide and K$_4$Fe(CN)$_6$, K$_3$Fe(CN)$_6$, or a combination thereof.

17. A redox flow battery system, comprising:
the aqueous electrolyte system of claim 15; and
a separator.

18. The redox flow battery system of claim 17, further comprising a carbon-based anode and a carbon-based cathode.

19. A compound or a salt thereof having a structure according to:
(i) any one of formulas IA-IIIA

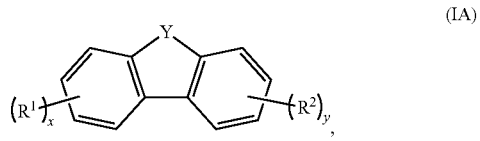

(IA)

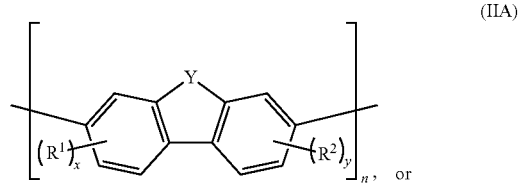

(IIA)

-continued (IIIA)

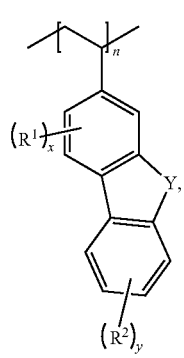

where Y is C=O or C(H)OH, each R¹ independently is SO₃Z or CO₂Z, each R² independently is SO₃Z or CF₃, each Z independently is a counterion with a +1 charge, n is an integer greater than 1, and x and y independently are 1, 2, 3, or 4, wherein (a) R¹ and R² are different electron withdrawing groups, or (b) the compound comprises two different R¹ or two different R² groups, or (c) both (a) and (b); or (ii) formula IC or formula IIIC (IC)

(IIIC)

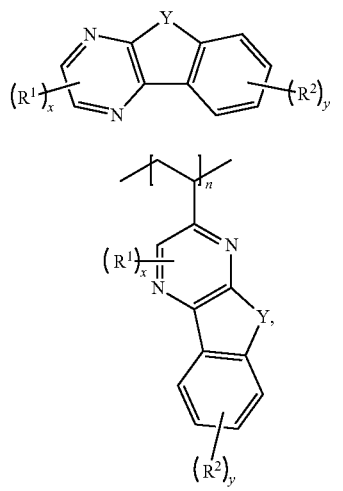

where Y is C=O or C(H)OH, x is 2, y is 0, and each R¹ independently is —CN or —OH.

20. A compound, comprising

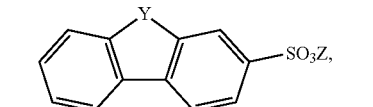

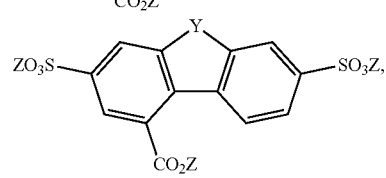

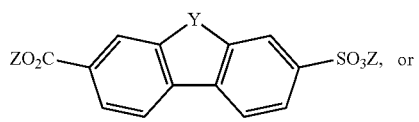

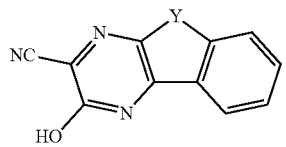

wherein:

Y is C=O or C(H)OH; and each Z independently is a counterion with a +1 charge.

21. A method for producing electrical energy, comprising:

pairing an aqueous solution comprising a compound according to claim 19 or a salt thereof wherein Y is C(H)OH against an oxidizing catholyte mixture in an electrochemical cell, thereby oxidizing the compound to its corresponding ketone where Y is C=O and producing electrical energy.

* * * * *